US011028129B2

(12) United States Patent
Franco

(10) Patent No.: US 11,028,129 B2
(45) Date of Patent: *Jun. 8, 2021

(54) COMPOSITIONS FOR EXPANDING REGULATORY T CELLS (TREG) POPULATIONS, AND TREATING AND AMELIORATING AUTOIMMUNE DISEASES AND CONDITIONS

(71) Applicant: The Regents of the University of California, Oakland, CA (US)

(72) Inventor: Alessandra Franco, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/542,168

(22) Filed: Aug. 15, 2019

(65) Prior Publication Data

US 2020/0109172 A1 Apr. 9, 2020

Related U.S. Application Data

(62) Division of application No. 16/022,306, filed on Jun. 28, 2018, now Pat. No. 10,428,113, which is a division of application No. 15/510,667, filed as application No. PCT/US2015/053044 on Sep. 29, 2015, now Pat. No. 10,035,823.

(60) Provisional application No. 62/066,741, filed on Oct. 21, 2014, provisional application No. 62/057,119, filed on Sep. 29, 2014.

(51) Int. Cl.
*C07K 7/08* (2006.01)
*A61K 39/00* (2006.01)
*A61K 9/127* (2006.01)
*A61K 9/14* (2006.01)
*A61K 38/00* (2006.01)

(52) U.S. Cl.
CPC .............. *C07K 7/08* (2013.01); *A61K 9/127* (2013.01); *A61K 9/14* (2013.01); *A61K 39/0005* (2013.01); *A61K 39/0008* (2013.01); *A61K 38/00* (2013.01); *A61K 2039/545* (2013.01)

(58) Field of Classification Search
CPC ............................. C07K 7/08; A61K 39/0008
See application file for complete search history.

(56) References Cited

U.S. PATENT DOCUMENTS

| | | | |
|---|---|---|---|
| 5,219,996 A | 6/1993 | Bodmer et al. | |
| 6,905,879 B2 | 6/2005 | Qui et al. | |
| 7,884,184 B2 | 2/2011 | De Groot et al. | |
| 7,939,075 B2 | 5/2011 | Dodel et al. | |
| 8,491,903 B2 | 7/2013 | Dodel et al. | |
| 8,586,006 B2 | 11/2013 | Hood et al. | |
| 8,741,293 B2 | 6/2014 | Dodel et al. | |
| 2003/0175845 A1 | 9/2003 | Kalbag et al. | |
| 2005/0112118 A1 | 5/2005 | Cimbora et al. | |
| 2006/0141528 A1 | 6/2006 | Aebersold et al. | |
| 2007/0254300 A1 | 11/2007 | Cimbora et al. | |
| 2009/0018067 A1 | 1/2009 | De Groot et al. | |
| 2010/0279382 A1 | 11/2010 | Aebersold et al. | |
| 2011/0182921 A1 | 7/2011 | De Groot et al. | |
| 2011/0212087 A1 | 9/2011 | Strohl et al. | |
| 2012/0082682 A1* | 4/2012 | Ashman | C07K 16/468 424/158.1 |
| 2012/0087862 A1 | 4/2012 | Hood et al. | |
| 2012/0121591 A1* | 5/2012 | Sullivan | A61P 11/06 424/134.1 |
| 2012/0245857 A1 | 9/2012 | Lee et al. | |
| 2013/0101598 A1* | 4/2013 | Smith | C07K 16/248 424/145.1 |
| 2013/0183293 A1* | 7/2013 | Smith | A61P 43/00 424/133.1 |
| 2013/0183321 A1* | 7/2013 | Smith | A61K 39/3955 424/172.1 |
| 2013/0280280 A1* | 10/2013 | Algate | C07K 16/2803 424/178.1 |

(Continued)

OTHER PUBLICATIONS

Young, Lee, W., "Notification of Transmittal of the International Search Report and the Written Opinion of the International Searching Authority, or the Declaration", Patent Cooperation Treaty No. PCTUS/2015/53044, United States of America as International Searching Authority, International Search Completed Dec. 23, 2015, International Search dated Jan. 21, 2016, 10 pages.

*Primary Examiner* — Amber D Steele
(74) *Attorney, Agent, or Firm* — Greer, Burn, & Crain, Ltd.; Gregory P. Einhorn

(57) ABSTRACT

In alternative embodiments, provided are compositions, including e.g., isolated, synthetic or recombinant peptides or polypeptides, for: expanding regulatory T cells (Treg) populations; or, for treating, ameliorating, preventing or reversing a vascular inflammation, and Kawasaki disease (KD) or a pediatric acute vasculitis of the coronary arteries, including vascular coronary abnormalities and the same or similar types of acute or chronic vascular inflammatory abnormalities, and methods for making and using them. In one embodiment, provided are immunotherapies for promoting expansion of natural, regulatory T cells to establish, or re-establish, vascular homeostasis; or, for treating, reversing, preventing or ameliorating: a disease or condition associated with an autoimmune disease or condition; an immune-mediated vascular disorder; a disease or condition that is currently treated with intravenous immunoglobulin (WIG) therapy; a vascular coronary abnormality; an acute or a chronic vasculitis; an autoimmune inflammatory vasculitis; a T cell mediated pediatric vasculitis; Kawasaki disease (KD) or a pediatric acute vasculitis of the coronary arteries; atherosclerosis; rheumatoid arthritis or Juvenile Idiopathic Arthritis; an autoimmune disease or condition; or, a neoplastic hematological disorder such as a lymphoma (e.g., a T cell lymphoma) or a leukemia.

21 Claims, 24 Drawing Sheets

Specification includes a Sequence Listing.

(56) References Cited

U.S. PATENT DOCUMENTS

2013/0302399 A1* 11/2013 Feldhaus .................. A61P 3/04
424/450
2013/0330324 A1* 12/2013 Elis .................. A61K 39/39558
424/133.1
2013/0336992 A1* 12/2013 Boone ................ C07K 16/2863
424/172.1

* cited by examiner

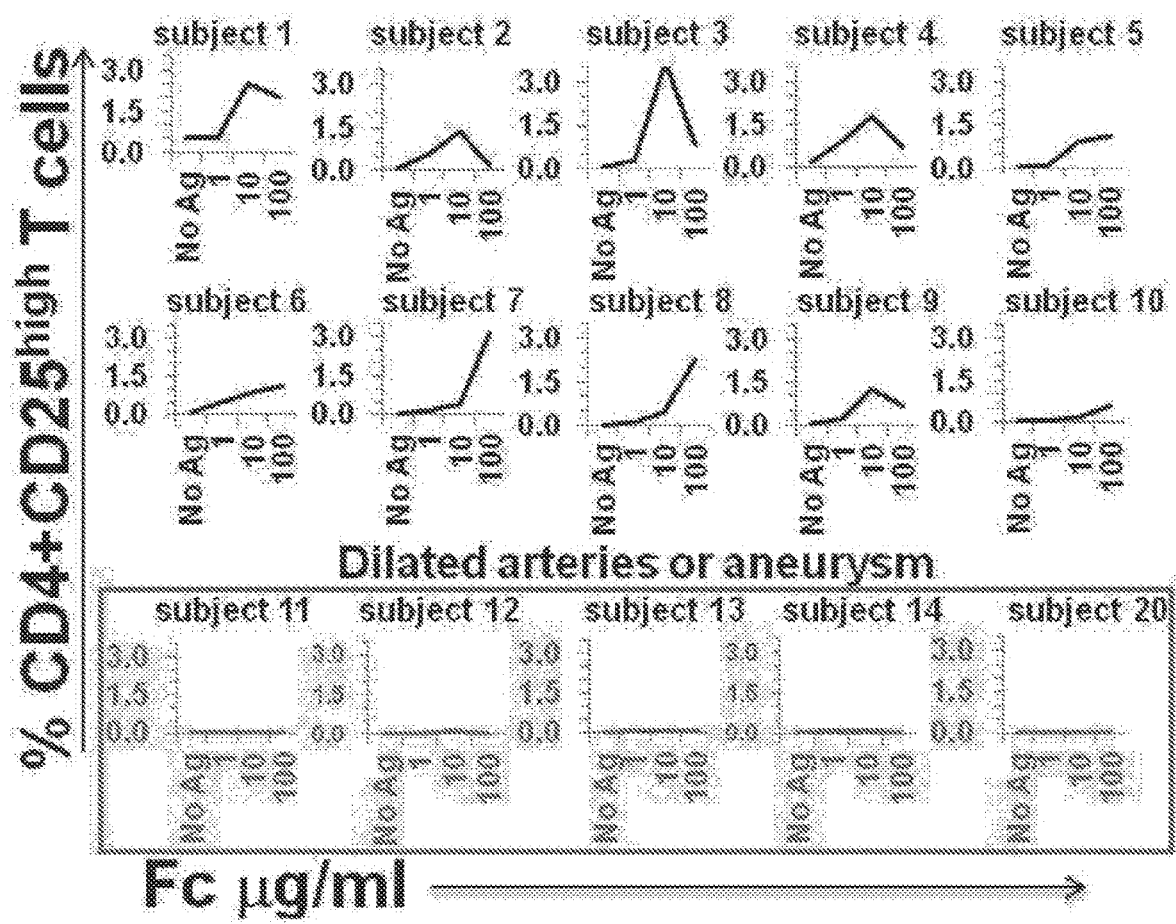

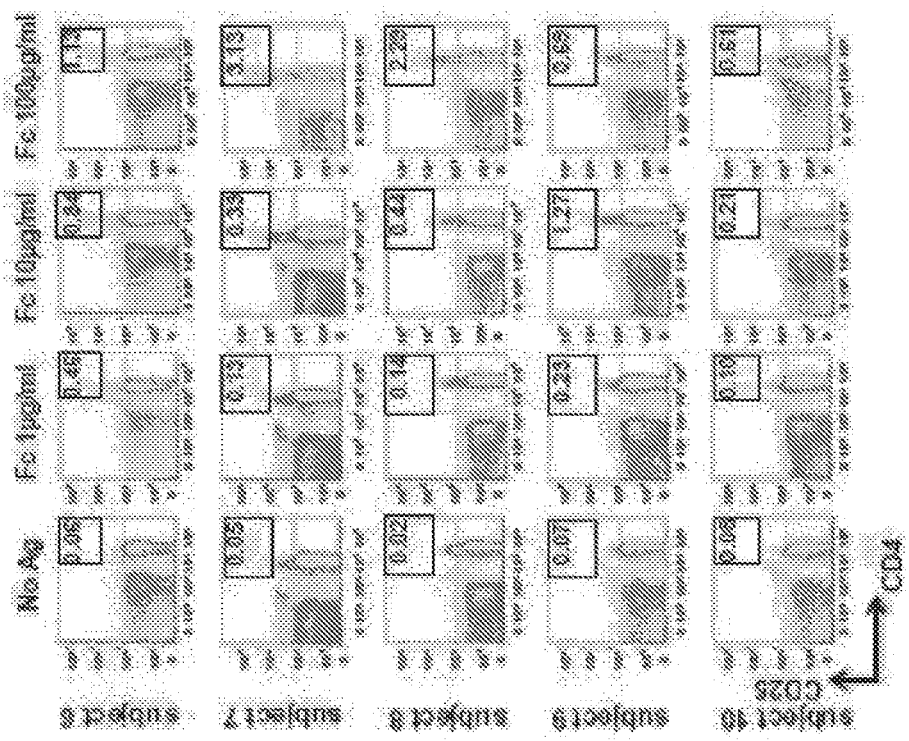
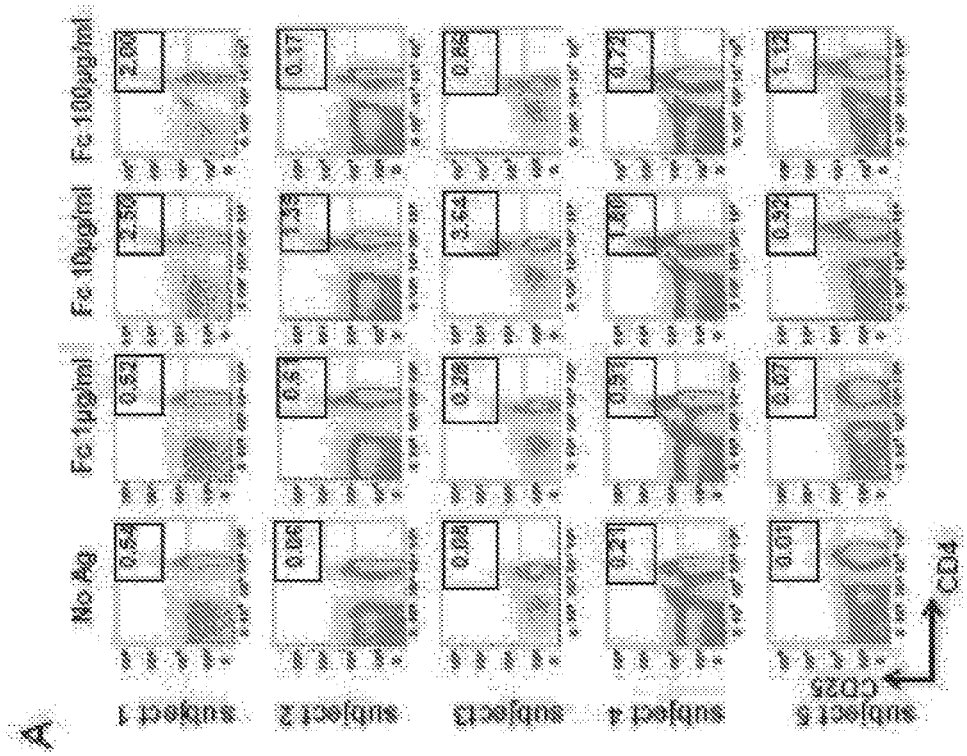
Fig. 10A

Fig. 12

Table 1. Demographic and clinical status of pediatric KD study subjects.

| Subject # | KD # | Age at onset (years) | Illness day at phlebotomy | Sex | Race/ethnicity | Coronary artery Z max* |
|---|---|---|---|---|---|---|
| Sub-acute | | | | | | |
| 1 | 0853 | 6.3 | Day 20 | Female | Hispanic | 1.9 |
| 2 | 5846 | 4.0 | Day 20 | Male | Hispanic | 1.2 |
| 3 | 5586 | 8.3 | Day 19 | Female | White | 2 |
| 4 | 5828 | 1.0 | Day 21 | Male | Hispanic | 2.4 (dilated) |
| 5 | 5877 | 1.5 | Day 21 | Male | Asian | 3.1 (dilated) |
| 6 | 5840 | 4.3 | Day 21 | Female | White | 3.4 (dilated) |
| 7 | 5873 | 0.5 | Day 18 | Female | White/Hispanic/Asian | 1.3 |
| 8 | 5872 | 2.1 | Day 19 | Male | White | 2.3 |
| 9 | 5870 | 2.0 | Day 19 | Male | White | 1.2 |
| 10 | 5820 | 2.3 | Day 19 | Female | Asian | 1 |

| KD subject # | KD # | Age at onset (years) | Interval from illness onset (years) | Sex | Race/ethnicity | Coronary artery Z max* |
|---|---|---|---|---|---|---|
| Convalescent | | | | | | |
| 11 | 5661 | 1.4 | 2.6 | Male | Hispanic | 0.8 |
| 12 | 5706 | 0.65 | 2 | Male | Hispanic/Asian | 1.4 |
| 13 | 5700 | 5.8 | 2 | Female | Hispanic | 1.1 |
| 14 | 5747 | 5.7 | 2 | Male | Asian/White | 1.2 |
| 15 | 5669 | 5.7 | 10 | Male | Hispanic/White | 1.3 |
| 16 | 5725 | 1.4 | 1 | Male | White | 1.5 |

*Z score defined as the internal diameter of the right and left anterior descending coronary arteries expressed as SD units from the mean normalized for body surface area; normal Z score <2.5. Zmax defined as the highest Z score of either coronary artery measured during the first 6 weeks after fever onset.

Fig. 13

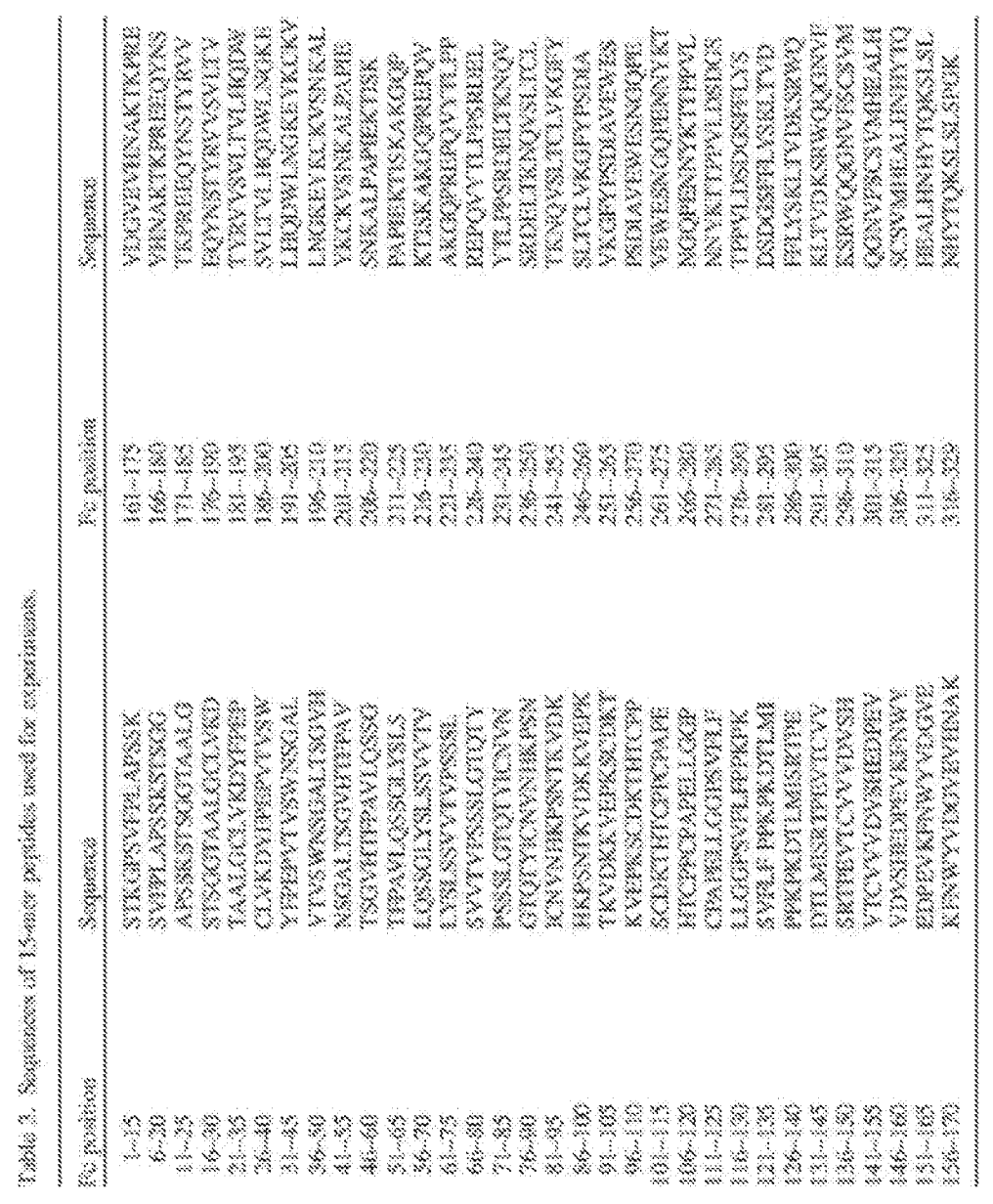

Table 3. Sequences of 15-mer peptides used for experiments.

| Fc positions | Sequence | Fc positions | Sequence |
|---|---|---|---|
| 1-15 | STKGPSVFPLAPSSK | 161-175 | YKTTPPVLDSDGSFFL |
| 6-20 | SVFPLAPSSKSTSGG | 166-180 | VLDSDGSFFLYSKLT |
| 11-25 | APSSKSTSGGTAALG | 171-185 | GSFFLYSKLTVDKSR |
| 16-30 | STSGGTAALGCLVKD | 176-190 | YSKLTVDKSRWQQGN |
| 21-35 | TAALGCLVKDYFPEP | 181-195 | VDKSRWQQGNVFSCS |
| 26-40 | CLVKDYFPEPVTVSW | 186-200 | WQQGNVFSCSVMHE |
| 31-45 | YFPEPVTVSWNSGAL | 191-205 | VFSCSVMHEALHNHY |
| 36-50 | VTVSWNSGALTSGVH | 196-210 | VMHEALHNHYTQKSL |
| 41-55 | NSGALTSGVHTFPAV | 201-215 | LHNHYTQKSLSLSPGK |
| 46-60 | TSGVHTFPAVLQSSG | | |
| 51-65 | TFPAVLQSSGLYSLS | | |
| 56-70 | LQSSGLYSLSSVVTV | | |
| 61-75 | LYSLSSVVTVPSSSL | | |
| 66-80 | SVVTVPSSSLGTQTY | | |
| 71-85 | PSSSLGTQTYICNVN | | |
| 76-90 | GTQTYICNVNHKPSN | | |
| 81-95 | ICNVNHKPSNTKVDK | | |
| 86-100 | HKPSNTKVDKKVEPK | | |
| 91-105 | TKVDKKVEPKSCDKT | | |
| 96-110 | KVEPKSCDKTHTCPP | | |
| 101-115 | SCDKTHTCPPCPAPE | | |
| 106-120 | HTCPPCPAPELLGGP | | |
| 111-125 | CPAPELLGGPSVFLF | | |
| 116-130 | LLGGPSVFLFPPKPK | | |
| 121-135 | SVFLFPPKPKDTLMI | | |
| 126-140 | PPKPKDTLMISRTPE | | |
| 131-145 | DTLMISRTPEVTCVV | | |
| 136-150 | SRTPEVTCVVVDVSH | | |
| 141-155 | VTCVVVDVSHEDPEV | | |
| 146-160 | VDVSHEDPEVKFNWY | | |
| 151-165 | EDPEVKFNWYVDGVE | | |
| 156-170 | KFNWYVDGVEVHNAK | | |

COMPOSITIONS FOR EXPANDING REGULATORY T CELLS (TREG) POPULATIONS, AND TREATING AND AMELIORATING AUTOIMMUNE DISEASES AND CONDITIONS

RELATED APPLICATIONS

This United States Utility Patent Application is a divisional of U.S. patent application Ser. No. 16/022,306, filed Jun. 28, 2018, now U.S. Pat. No. 10,428,113, which is a divisional of U.S. Utility application Ser. No. 15/510,667, filed Mar. 10, 2017, now U.S. Pat. No. 10,035,823, which is a National Stage Entry of PCT/US2015/053044, filed Sep. 29, 2015, now expired, which claims priority to U.S. Provisional Patent Applications 62/066,741, filed Oct. 21, 2014, and 62/057,119, filed Sep. 29, 2014, the contents of which are incorporated herein in their entirety. The aforementioned applications are expressly incorporated herein by reference in their entirety and for all purposes.

STATEMENT AS TO FEDERALLY SPONSORED RESEARCH

This invention was made with government support under HL103536, HL108460, and RR031980 awarded by the National Institutes of Health. The government has certain rights in the invention.

FIELD OF THE INVENTION

This invention generally relates to immunology and medicine. In alternative embodiments, provided are compositions, including e.g., isolated, synthetic or recombinant peptides, for expanding regulatory T cells (Treg) populations and treating, ameliorating, preventing or reversing: an autoimmune disease or condition; an acute or chronic vascular inflammation, including Kawasaki disease (KD), a pediatric acute vasculitis of the coronary arteries or a pediatric acute vasculitis of the coronary arteries, and other vascular coronary abnormalities, including the same or similar types of acute or chronic vascular inflammatory abnormalities, and including an atherosclerosis, and methods for making and using them. In one embodiment, provided are immunotherapies for promoting expansion of natural, regulatory T cells to establish, or re-establish, vascular homeostasis.

BACKGROUND OF INVENTION

Kawasaki disease (KD) is an emerging third world pediatric disease that frequently leaves lasting coronary abnormalities. Current treatment is intravenous (IV) immunoglobulin (Ig) (or IVIG, or MG) infusion, which is expensive and requires hospitalization and often not an option in the third world regions where the disease is prevalent.

IVIG therapy generates a specific population of natural regulatory T cells (nTregs) that recognize the heavy region constant (Fc) of immunoglobulin G. Fe-specific Treg are very relevant to maintain vascular homeostasis and can be found in Kawasaki disease subjects that do not develop arterial abnormalities after IVIG and in a variety of acute pediatric febrile controls but not autoimmune diseases. Normal healthy adults have detectable Fc-specific nTreg in their peripheral blood suggesting that this Treg repertoire is important in controlling vascular homeostasis.

Children that develop coronary arteries abnormalities despite IVIG treatment do not expand Fe-specific nTreg. Characterization of Fc-specific nTreg clones derived from children that did not develop arterial abnormalities after KD suggest that the suppression mechanism of pro-inflammatory T cell responses (by Fc-specific nTreg) occur in the lymph nodes, and Fe-specific nTregs are activated by resident B cells. IgG+ mature B cells can activate Fc-specific nTreg in the absence of soluble Fc fragments. The characterization of immunodominant Fc peptides that bind multiple Human Leukocytes Antigens (HLA) alleles would be a great alternative to IVIG.

SUMMARY OF THE INVENTION

In alternative embodiments, provided are isolated, synthetic or recombinant peptides having a sequence comprising or consisting of:

| | |
|---|---|
| TAALGCLVKDYFPEP | (SEQ ID NO: 1) |
| CLVKDYFPEPVTVSW | (SEQ ID NO: 2) |
| SVFLFPPKPKDTLMI | (SEQ ID NO: 3) |
| PPKPKDTLMISRTPE | (SEQ ID NO: 4) |
| KLTVDKSRWQQGNVF | (SEQ ID NO: 5) |
| KSRWQQGNVFSCSVM | (SEQ ID NO: 6) |
| NGQPENNYKTTPPVL | (SEQ ID NO: 7) |
| NNYKTTPPVLDSDGS | (SEQ ID NO: 8) |
| TFPAVLQSSGLYSLS | (SEQ ID NO: 9) |
| LQSSGLYSLSSVVTV | (SEQ ID NO: 10) |
| LYSLSSVVTVPSSSL | (SEQ ID NO: 11) |
| SVVTVPSSSLGTQTY | (SEQ ID NO: 12) |
| EQYNSTYRVVSVLTV, | (SEQ ID NO: 13) |
| TYRVVSVLTVLHQDW, | (SEQ ID NO: 14) |
| TPPVLDSDGSFFLYS, | (SEQ ID NO: 15) |
| QGNVFSCSVMHEALH, or | (SEQ ID NO: 16) |
| SCSVMHEALHNHYTQ, | (SEQ ID NO: 17) | wherein in alternative embodiments provided are methods and uses for administering at least one, two, three, four, five, six, seven or eight or more or all of the isolated, synthetic or recombinant peptides to an individual, and optionally this administration generates natural regulatory T cells (nTregs)

that can suppress pro-inflammatory T cells and pro-inflammatory T cell responses, and optionally the individual is a human.

In alternative embodiments, the isolated, synthetic or recombinant peptide as provided herein has at least one conservative amino acid substitution and retains its property of generating (ability to generate) natural regulatory T cells (nTregs) that can suppress pro-inflammatory T cells and pro-inflammatory T cell responses when administered to an individual, wherein optionally the at least one conservative amino acid substitution comprises substituting an amino acid with another amino acid of like characteristics; or, a conservative substitution comprises: replacement of an aliphatic amino acid with another aliphatic amino acid; replacement of a Serine with a Threonine or vice versa; replacement of an acidic residue with another acidic residue; replacement of a residue bearing an amide group with another residue bearing an amide group; exchange of a basic residue with another basic residue; or replacement of an aromatic residue with another aromatic residue.

In alternative embodiments, the peptide, or at least one amino acid in the peptide, comprises or consists of a peptidomimetic or a non-natural amino acid residue.

In alternative embodiments, provided herein are isolated, synthetic or recombinant nucleic acids comprising or consisting of a sequence encoding a peptide or polypeptide as provided herein, wherein optionally the nucleic acid further comprises, or is contained within, an expression cassette, a plasmid, an expression vector or a recombinant virus, wherein optionally the nucleic acid, or the expression cassette, plasmid, expression vector or recombinant virus is contained with a cell (optionally a "host cell"), optionally a human cell or a non-human cell, and optionally the cell is transformed with the nucleic acid, or the expression cassette, plasmid, expression vector or recombinant virus. In alternative embodiments, provided herein are host cells transduced, transfected or otherwise engineered to contain within an isolated, synthetic or recombinant peptide or polypeptide as provided herein and/or an isolated, synthetic or recombinant nucleic acid or an expression cassette, plasmid, expression vector or recombinant virus as provided herein.

In alternative embodiments, provided are compositions comprising: one isolated, synthetic or recombinant peptide, or two, three, four, five, six, seven, eight or more or all isolated, synthetic or recombinant peptides as provided herein; or, an isolated, synthetic or recombinant nucleic acid, or an expression cassette, a plasmid, an expression vector or a recombinant virus, or a cell, as provided herein.

In alternative embodiments, provided are pharmaceutical compositions or formulations comprising: one isolated, synthetic or recombinant peptide, or two, three, four or five, six, seven, eight, nine or ten or more isolated, synthetic or recombinant peptides as provided herein; an isolated, synthetic or recombinant nucleic acid, or an expression cassette, a plasmid, an expression vector or a recombinant virus, or a cell, as provided herein; or, a composition as provided herein, and a pharmaceutically acceptable excipient. In alternative embodiments, the pharmaceutical composition or formulation is formulated for administration via a parenteral route comprising or consisting of a subcutaneous, an intravenous (IV), an intradermal, an intramuscular, an intraperitoneal, an intranasal, a transdermal or a buccal route; or the pharmaceutical composition or formulation is formulated for oral or topical administration; or the pharmaceutical composition or formulation is formulated for administration intradermally as a sterile formulation, or as an inhaled powder, or is formulated for administration as a controlled release formulation, a tablet, a pill, a gel, a patch, in an implant or in a spray. In alternative embodiments, the pharmaceutical composition or formulation is formulated as a sterile solution for injection, or as a powder or a lyophilized (freeze-dried) composition. In alternative embodiments, the pharmaceutical composition or formulation is formulated as a liquid, an emulsion, a lyophilized powder, a spray, a cream, a lotion, a controlled release formulation, a tablet, a pill, a gel, a patch, in an implant or in a spray; or is formulated as an aqueous or a non-aqueous isotonic sterile injection solution, or an aqueous or a non-aqueous sterile suspension.

In alternative embodiments, provided are liposomes comprising: an isolated, synthetic or recombinant peptide as provided herein; an isolated, synthetic or recombinant nucleic acid, or an expression cassette, a plasmid, an expression vector or a recombinant virus, or a cell, as provided herein; a composition as provided herein; a pharmaceutical or formulation as provided herein; or, any combination thereof.

In alternative embodiments, provided are nanoparticles comprising: an isolated, synthetic or recombinant peptide as provided herein; an isolated, synthetic or recombinant nucleic acid, or an expression cassette, a plasmid, an expression vector or a recombinant virus, or a cell, as provided herein; a composition as provided herein; a pharmaceutical or formulation as provided herein; a liposome as provided herein; or, any combination thereof.

In alternative embodiments, provided are therapeutic combinations comprising two, three, four, five, six, seven, eight or more or all of the isolated, synthetic or recombinant peptides as provided herein; an isolated, synthetic or recombinant nucleic acid, or an expression cassette, a plasmid, an expression vector or a recombinant virus, or a cell, as provided herein; a composition as provided herein; a pharmaceutical or formulation as provided herein; a liposome as provided herein; or, nanoparticles as provided herein, wherein optionally the therapeutic combination is used for:

(a) immune-regulation by expanding natural regulatory T cells (nTregs) or nTreg suppression of pro-inflammatory T cells and/or pro-inflammatory T cell responses; or (b) the treatment, prevention or amelioration of:
a disease or condition associated with an immune-mediated vascular disorder;
a disease or condition that is currently treated with intravenous immunoglobulin (IVIG) therapy;
a disease or condition ameliorated by immune regulation comprising suppression of pro-inflammatory T cells and/or suppression of pro-inflammatory T cell responses;
sa vascular coronary abnormality;
an autoimmune inflammatory vasculitis;
an acute or a chronic vasculitis (or vascular inflammation);
a T cell mediated pediatric vasculitis;
Kawasaki disease (KD) or a pediatric acute vasculitis of the coronary arteries;
an atherosclerosis;
rheumatoid arthritis;
Juvenile Idiopathic Arthritis;
an autoimmune disease or condition; or
a neoplastic hematological disorder, a leukemia or a lymphoma, such as a T cell lymphoma.

In alternative embodiments, provided are vaccines comprising: an isolated, synthetic or recombinant peptide as provided herein; an isolated, synthetic or recombinant nucleic acid, or an expression cassette, a plasmid, an expression vector or a recombinant virus, or a cell, as provided herein; a composition as provided herein; a pharmaceutical or formulation as provided herein; a liposome as provided herein, a nanoparticle as provided herein; a therapeutic combination as provided herein; or, any combination thereof, for the manufacture of a medicament or a vaccine, wherein optionally the vaccine is administered with an adjuvant or an incomplete adjuvant.

In alternative embodiments, provided are Uses of: an isolated, synthetic or recombinant peptide as provided herein; an isolated, synthetic or recombinant nucleic acid, or an expression cassette, a plasmid, an expression vector or a recombinant virus, or a cell, as provided herein; a composition as provided herein; a pharmaceutical or formulation as provided herein; a liposome as provided herein, a nanoparticle as provided herein; a therapeutic combination as provided herein; a vaccine as provided herein; or, any combination thereof, for the manufacture of a medicament or a vaccine.

In alternative embodiments, provided are uses of: an isolated, synthetic or recombinant peptide as provided herein; an isolated, synthetic or recombinant nucleic acid, or an expression cassette, a plasmid, an expression vector or a recombinant virus, or a cell, as provided herein; a composition as provided herein; a pharmaceutical or formulation as provided herein; a liposome as provided herein, a nanoparticle as provided herein; a therapeutic combination as provided herein; a vaccine as provided herein; or, any combination thereof, for the manufacture of a medicament or a vaccine for:

(a) immune-regulation by expanding natural regulatory T cells (nTregs) or nTreg suppression of pro-inflammatory T cells and/or pro-inflammatory T cell responses; or (b) the treatment, prevention or amelioration of:
a disease or condition associated with an immune-mediated vascular disorder;
a disease or condition that is currently treated with intravenous immunoglobulin (IVIG) therapy;
a disease or condition ameliorated by immune regulation comprising suppression of pro-inflammatory T cells and/or suppression of pro-inflammatory T cell responses;
sa vascular coronary abnormality;
an autoimmune inflammatory vasculitis;
an acute or a chronic vasculitis (or vascular inflammation);
a T cell mediated pediatric vasculitis;
Kawasaki disease (KD) or a pediatric acute vasculitis of the coronary arteries;
an atherosclerosis;
rheumatoid arthritis,
Juvenile Idiopathic Arthritis,
an autoimmune disease or condition; or
a neoplastic hematological disorder, a leukemia or a lymphoma, such as a T cell lymphoma.

In alternative embodiments, provided are methods for:
(a) effecting immune-regulation or immune homeostasis by expanding natural regulatory T cells (nTregs) or causing or promoting nTreg suppression (partial or complete) of pro-inflammatory T cells and/or pro-inflammatory T cell responses; or (b) the treatment, prevention or amelioration of:
a disease or condition associated with an immune-mediated vascular disorder;
a disease or condition that is currently treated with intravenous immunoglobulin (IVIG) therapy;
a disease or condition ameliorated by immune regulation comprising suppression of pro-inflammatory T cells and/or suppression of pro-inflammatory T cell responses;
a vascular coronary abnormality;
an acute or a chronic vasculitis (or vascular inflammation);
an autoimmune inflammatory vasculitis;
a T cell mediated pediatric vasculitis;
Kawasaki disease (KD) or a pediatric acute vasculitis of the coronary arteries;
an atherosclerosis;
rheumatoid arthritis,
Juvenile Idiopathic Arthritis,
an autoimmune disease or condition; or
a neoplastic hematological disorder, a leukemia or a lymphoma, such as a T cell lymphoma;
comprising:
administering to an individual in need thereof an effective amount of: an isolated, synthetic or recombinant peptide as provided herein; an isolated, synthetic or recombinant nucleic acid, or an expression cassette, a plasmid, an expression vector or a recombinant virus, or a cell, as provided herein; a composition as provided herein; a pharmaceutical or formulation as provided herein; a liposome as provided herein, a nanoparticle as provided herein; a therapeutic combination as provided herein; a vaccine as provided herein; or, any combination thereof, to an individual in need thereof,
thereby:
effecting immune-regulation or immune homeostasis by expanding natural regulatory T cells (nTregs) or causing or promoting nTreg suppression of pro-inflammatory T cells and/or pro-inflammatory T cell responses; or
treating, preventing or ameliorating:
a disease or condition associated with an immune-mediated vascular disorder;
a disease or condition that is currently treated with intravenous immunoglobulin (IVIG) therapy;
a disease or condition ameliorated by immune regulation comprising suppression of pro-inflammatory T cells and/or suppression of pro-inflammatory T cell responses;
a vascular coronary abnormality;
an acute or a chronic vasculitis (or vascular inflammation);
an autoimmune inflammatory vasculitis;
a T cell mediated pediatric vasculitis;
Kawasaki disease (KD) a pediatric acute vasculitis of the coronary arteries;
an atherosclerosis;
rheumatoid arthritis,
Juvenile Idiopathic Arthritis,
an autoimmune disease or condition; or
a neoplastic hematological disorder, a leukemia or a lymphoma, such as a T cell lymphoma.

In alternative embodiments of methods as provided herein, an isolated, synthetic or recombinant peptide or polypeptide as provided herein; an isolated, synthetic or recombinant nucleic acid, or an expression cassette, a plasmid, an expression vector or a recombinant virus, or a cell, as provided herein; a composition as provided herein; a pharmaceutical or formulation as provided herein; a liposome as provided herein, a nanoparticle as provided herein;

a therapeutic combination as provided herein; a vaccine as provided herein; or, any combination thereof, is administered:
via an enteral or a parenteral route, or orally, or systemically or topically;
via a parenteral route comprising a subcutaneous, an intravenous (IV), an intradermal, an intramuscular, an intraperitoneal, an intranasal, a transdermal or a buccal route;
intradermally as a sterile formulation;
as a controlled release formulation, a tablet, a pill, a gel, a patch, in an implant or in a spray, as an inhaled powder; or
with a non-specific immuno-stimulator, wherein optionally the non-specific immuno-stimulator comprises or consists of a granulocyte-macrophage colony-stimulating factor polypeptide; or sargramostim, or LEUKINE™ (Bayer, Leverkusen, Germany).

In alternative embodiments of methods as provided herein, an isolated, synthetic or recombinant peptide or polypeptide as provided herein; an isolated, synthetic or recombinant nucleic acid, or an expression cassette, a plasmid, an expression vector or a recombinant virus, or a cell, as provided herein; a composition as provided herein; a pharmaceutical or formulation as provided herein; a liposome as provided herein, a nanoparticle as provided herein; a therapeutic combination as provided herein; a vaccine as provided herein; or, any combination thereof, is administered:
parenterally by one bolus injection, or by two, three or four or more bolus injections, or by gradual perfusion over time;
at intervals of 1 week, 2 weeks, 4 weeks (or one month), 6 weeks, 8 weeks (or two months) or one year; or
at a daily dose of peptide in a range of about 10 nanograms to 10 milligrams, or about 1 microgram to 10 milligrams.

In alternative embodiments of methods as provided herein,
an isolated, synthetic or recombinant peptide as provided herein; an isolated, synthetic or recombinant nucleic acid, or an expression cassette, a plasmid, an expression vector or a recombinant virus, or a cell, as provided herein; a composition as provided herein; a pharmaceutical or formulation as provided herein; a liposome as provided herein, a nanoparticle as provided herein; a therapeutic combination as provided herein; a vaccine as provided herein; or, any combination thereof, is administered:
as a prophylactic or preventative measure to an individual having a personal history of, or to an individual having a detected genotype or phenotype indicating a predisposition to:
a disease or condition associated with an immune-mediated vascular disorder;
a disease or condition that is currently treated with intravenous immunoglobulin (IVIG) therapy;
a disease or condition ameliorated by immune regulation comprising suppression of pro-inflammatory T cells and/or suppression of pro-inflammatory T cell responses;
a vascular coronary abnormality;
an acute or a chronic vasculitis (or vascular inflammation);
an autoimmune inflammatory vasculitis;
a T cell mediated pediatric vasculitis;
Kawasaki disease (KD) or a pediatric acute vasculitis of the coronary arteries;
an atherosclerosis;
rheumatoid arthritis,
Juvenile Idiopathic Arthritis,
an autoimmune disease or condition; or
a neoplastic hematological disorder, a leukemia or a lymphoma, such as a T cell lymphoma.

The details of one or more embodiments as provided herein are set forth in the description below. Other features, objects, and advantages exemplary embodiments as provided herein will be apparent from the description and from the claims.

All publications, patents, patent applications, GenBank sequences and ATCC deposits, cited herein are hereby expressly incorporated by reference for all purposes.

The embodiments of the description described herein are not intended to be exhaustive or to limit the disclosure to the precise forms disclosed in the following drawings or detailed description. Rather, the embodiments are chosen and described so that others skilled in the art can appreciate and understand the principles and practices of the description.

BRIEF DESCRIPTION OF THE DRAWINGS

The drawings set forth herein are illustrative of embodiments of the invention and are not meant to limit the scope of the invention as encompassed by the claims.

FIG. 1B graphically illustrates a representative enumeration of a cell sorting scan of CD4+ $CD25^{high}$ T cells in response to the whole Fc and peptide pool 121-135; 126-140 in PBMC cultures from a CAA+KD subject with aneurysms; as described in detail in Example 1, below.

FIG. 3A and FIG. 3B graphically illustrates percent CD4+$CD25^{high}$ Treg cell expansion to scalar doses of Fc (as µg/ml) as analyzed by flow cytometry in PBMC cultures derived from 15 sub-acute KD subjects, with normal arteries and 5 with dilated arteries or aneurysm previously studied for lymphokine production, PBMC were cultured for 4 days with 0 (no antigen), 1, 10, or 100<g/ml of purified Fc fragments; FIG. 3B (which is FIG. 2B, in Example 2) graphically illustrates a summary of the Treg response in 15 sub-acute KD subjects described in FIG. 3A as the percent increase Fc-specific Treg in Sub-acute KD subjects after IVIG, and normal coronary arteries, as described in detail in Example 2, below.

FIG. 7A: Left graphic illustration: Production of IL-10, IL-4 and TGFβ measured by ELISA 48 hours after stimulation with autologous, irradiated B cells pulsed with 20 μg/ml Fc fragments; FIG. 7A Right graphic illustration: qRT-PCR analysis of cell lysates from the same three Treg clones; and, FIG. 7B illustrates phenotype of a representative Treg clone characterized as CD4+ CD25$^{high}$, intracellular FOXP3$^{high}$, CD45RA$^{low}$, IL-7r$^{low}$, IL15r−, CCR6−, CCR7$^{high}$ and CCR4−, as described in detail in Example 2, below.

FIG. 8A: Live, but not paraformaldehyde-fixed, autologous EBV-transformed IgG+ B cells stimulate Treg clones to secrete IL-10 and IL-4 in the absence of exogenous Fc; FIG. 8B: only autologous, but not allogeneic IgG+ B cells activate a Fc-specific Treg clone, as described in detail in Example 2, below.

FIG. 10A and FIG. 10B graphically illustrate cell sorting data showing Treg response to purified Fc and F(ab)2 fragments in sub-acute KD subjects: FIG. 10A: CD4+ CD25$^{high}$ Treg expansion in PBMC cultures from sub-acute KD subjects with normal arteries after IVIG therapy in response to scalar doses of Fc; and, FIG. 10B: lack of CD4+CD25$^{high}$ Treg expansion in response to F(ab)2 fragments in 4 patients within the same cohort, as described in detail in Example 2, below.

FIG. 12 illustrates Table 1 of Example 3, which summarizes the demographic and clinical status of pediatric KD study subjects, as described in detail in Example 3, below.

FIG. 13 illustrates Table 3 of Example 3, which summarizes the total 64 peptides, each 15 amino acids in length, with a 10 amino acid-overlap for each peptide, spanning the whole Fc molecule, that were used to define the fine specificity of Fc-specific nTreg; the table illustrates the amino acid sequences of the 15-mer overlapping peptides, as described in detail in Example 3, below, where ** indicates an exemplary peptide sequence as provided herein, and:

Figure 1A:
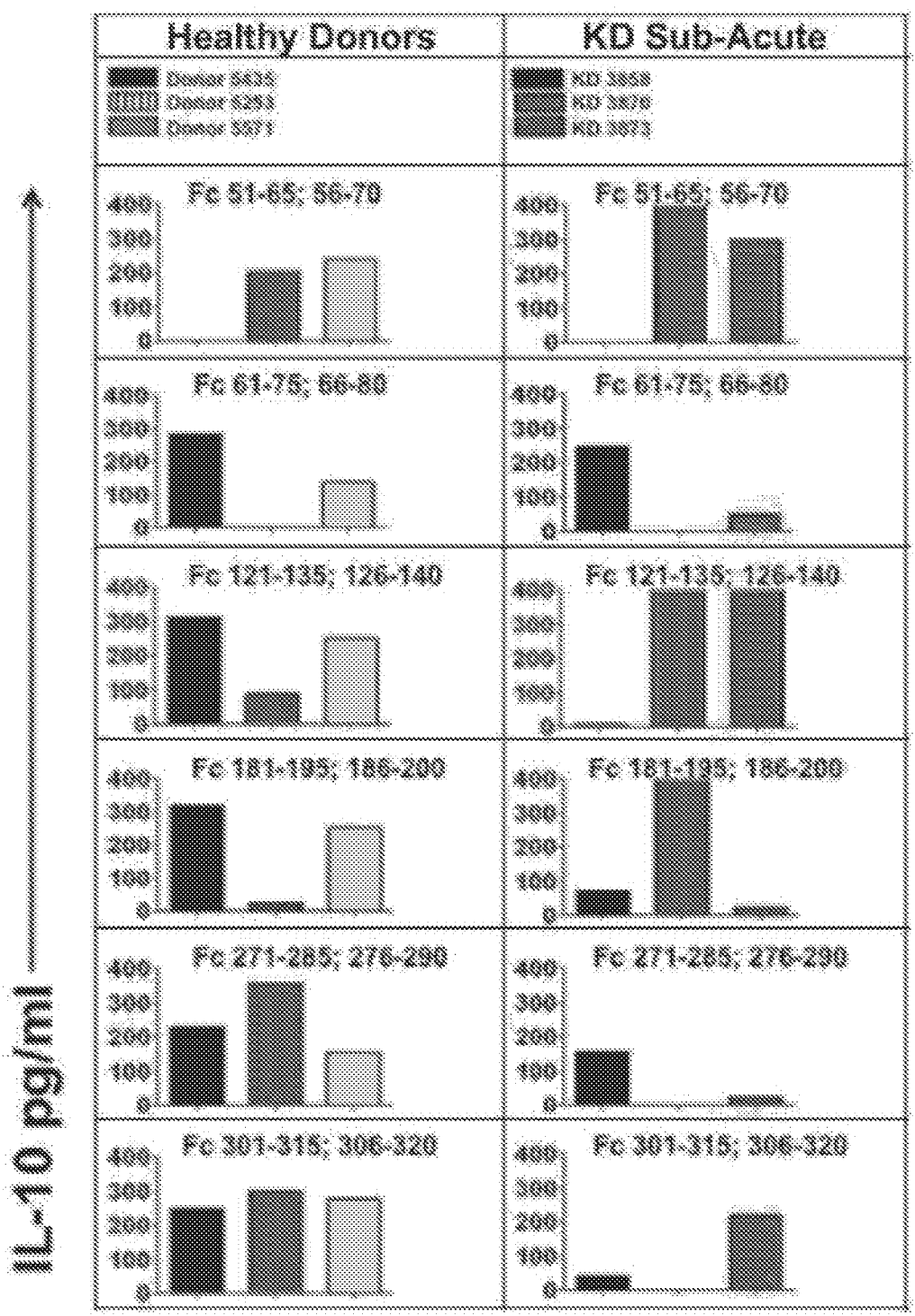
FIG. 1A and FIG. 1B graphically illustrates: IL-10 secretion by peptide-specific Treg; Treg lines from the KD patient with coronary artery aneurysm (CAA) are shown as KD 3873, right-hand-most graphic column in "KD Sub-Acute" side of the figure.

Fc position 1-15 (SEQ ID NO: 18)
STKGPSVFPLAPSSK

Fc position 6-20 (SEQ ID NO: 19)
SVFPLAPSSKSTSGG

Fc position 11-25 (SEQ ID NO: 20)
APSSKSTSGGTAALG

Fc position 16-30 (SEQ ID NO: 21)
STSGGTAALGCLVKD

** Fc position 21-35 (SEQ ID NO: 1)
TAALGCLVKDYFPEP

** Fc position 26-40 (SEQ ID NO: 2)
CLVKDYFPEPVTVSW

Fc position 31-45 (SEQ ID NO: 22)
YFPEPVTVSWNSGAL

Fc position 36-50 (SEQ ID NO: 23)
VTVSWNSGALTSGVH

Fc position 41-55 (SEQ ID NO: 24)
NSGALTSGVHTFPAV

Fc position 46-60 (SEQ ID NO: 25)
TSGVHTFPAVLQSSG

** Fc position 51-65 (SEQ ID NO: 9)
TFPAVLQSSGLYSLS

** Fc position 56-70 (SEQ ID NO: 10)
LQSSGLYSLSSVVTV

** Fc position 61-75 (SEQ ID NO: 11)
LYSLSSVVTVPSSSL

** Fc position 66-80 (SEQ ID NO: 12)
SVVTVPSSSLGTQTY

Fc position 71-85 (SEQ ID NO: 26)
PSSSLGTQTYICNVN

-continued

Fc position 76-90
(SEQ ID NO: 27)
GTQTYICNVNHKPSN

Fc position 81-95
(SEQ ID NO: 28)
ICNVNHKPSNTKVDK

Fc position 86-100
(SEQ ID NO: 29)
HKPSNTKVDKKVEPK

Fc position 91-105
(SEQ ID NO: 30)
TKVDKKVEPKSCDKT

Fc position 96-110
(SEQ ID NO: 31)
KVEPKSCDKTHTCPP

Fc position 101-115
(SEQ ID NO: 32)
SCDKTHTCPPCPAPE

Fc position 106-120
(SEQ ID NO: 33)
HTCPPCPAPELLGGP

Fc position 111-125
(SEQ ID NO: 34)
CPAPELLGGPSVFLF

Fc position 116-130
(SEQ ID NO: 35)
LLGGPSVFLFPPKPK

** Fc position 126-140
(SEQ ID NO: 4)
PPKPKDTLMISRTPE

Fc position 131-145
(SEQ ID NO: 36)
DTLMISRTPEVTCVV

Fc position 136-150
(SEQ ID NO: 37)
SRTPEVTCVVVDVSH

Fc position 141-155
(SEQ ID NO: 38)
VTCVVVDVSHEDPEV

Fc position 146-160
(SEQ ID NO: 39)
VDVSHEDPEVKFNWY

Fc position 151-165
(SEQ ID NO: 40)
EDPEVKFNWYVDGVE

Fc position 156-170
(SEQ ID NO: 41)
KFNWYVDGVEVHNAK

Fc position 161-175
(SEQ ID NO: 42)
VDGVEVHNAKTKPRE

Fc position 166-180
(SEQ ID NO: 43)
VHNAKTKPREEQYNS

Fc position 171-185
(SEQ ID NO: 44)
TKPREEQYNSTYRVV

** Fc position 176-190
(SEQ ID NO: 13)
EQYNSTYRVVSVLTV

-continued

** Fc position 181-195
(SEQ ID NO: 14)
TYRVVSVLTVLHQDW

Fc position 186-200
(SEQ ID NO: 45)
SVLTVLHQDWLNGKE

Fc position 191-205
(SEQ ID NO: 46)
LHQDWLNGKEYKCKV

Fc position 196-210
(SEQ ID NO: 47)
LNGKEYKCKVSNKAL

Fc position 206-220
(SEQ ID NO: 48)
SNKALPAPIEKTISK

Fc position 211-225
(SEQ ID NO: 49)
PAPIEKTISKAKGQP

Fc position 216-230
(SEQ ID NO: 50)
KTISKAKGQPREPQV

Fc position 221-235
(SEQ ID NO: 51)
AKGQPREPQVYTLPP

Fc position 226-240
(SEQ ID NO: 52)
REPQVYTLPPSRDEL

Fc position 231-245
(SEQ ID NO: 53)
YTLPPSRDELTKNQV

Fc position 236-250
(SEQ ID NO: 54)
SRDELTKNQVSLTCL

Fc position 241-255
(SEQ ID NO: 55)
TKNQVSLTCLVKGFY

Fc position 246-260
(SEQ ID NO: 56)
SLTCLVKGFYPSDIA

Fc position 251-265
(SEQ ID NO: 57)
VKGFYPSDIAVEWES

Fc position 256-270
(SEQ ID NO: 58)
PSDIAVEWESNGQPE

Fc position 261-275
(SEQ ID NO: 59)
VEWESNGQPENNYKT

** Fc position 266-280
(SEQ ID NO: 7)
NGQPENNYKTTPPVL

** Fc position 271-285
(SEQ ID NO: 8)
NNYKTTPPVLDSDGS

** Fc position 276-290
(SEQ ID NO: 15)
TPPVLDSDGSFFLYS

Fc position 281-295
(SEQ ID NO: 60)
DSDGSFFLYSKLTVD

```
-continued
Fc position 286-300
                              (SEQ ID NO: 61)
FFLYSKLTVDKSRWQ

** Fc position 291-305
                              (SEQ ID NO: 5)
KLTVDKSRWQQGNVF

** Fc position 296-310
                              (SEQ ID NO: 6)
KSRWQQGNVFSCSVM

** Fc position 301-315
                              (SEQ ID NO: 16)
QGNVFSCSVMHEALH

** Fc position 306-320
                              (SEQ ID NO: 17)
SCSVMHEALHNHYTQ Fc position 311-325
                              (SEQ ID NO: 62)
HEALHNHYTQKSLSL Fc position 316-329
                              (SEQ ID NO: 63)
NHYTQKSLSLSPGK
```

Figure 14:
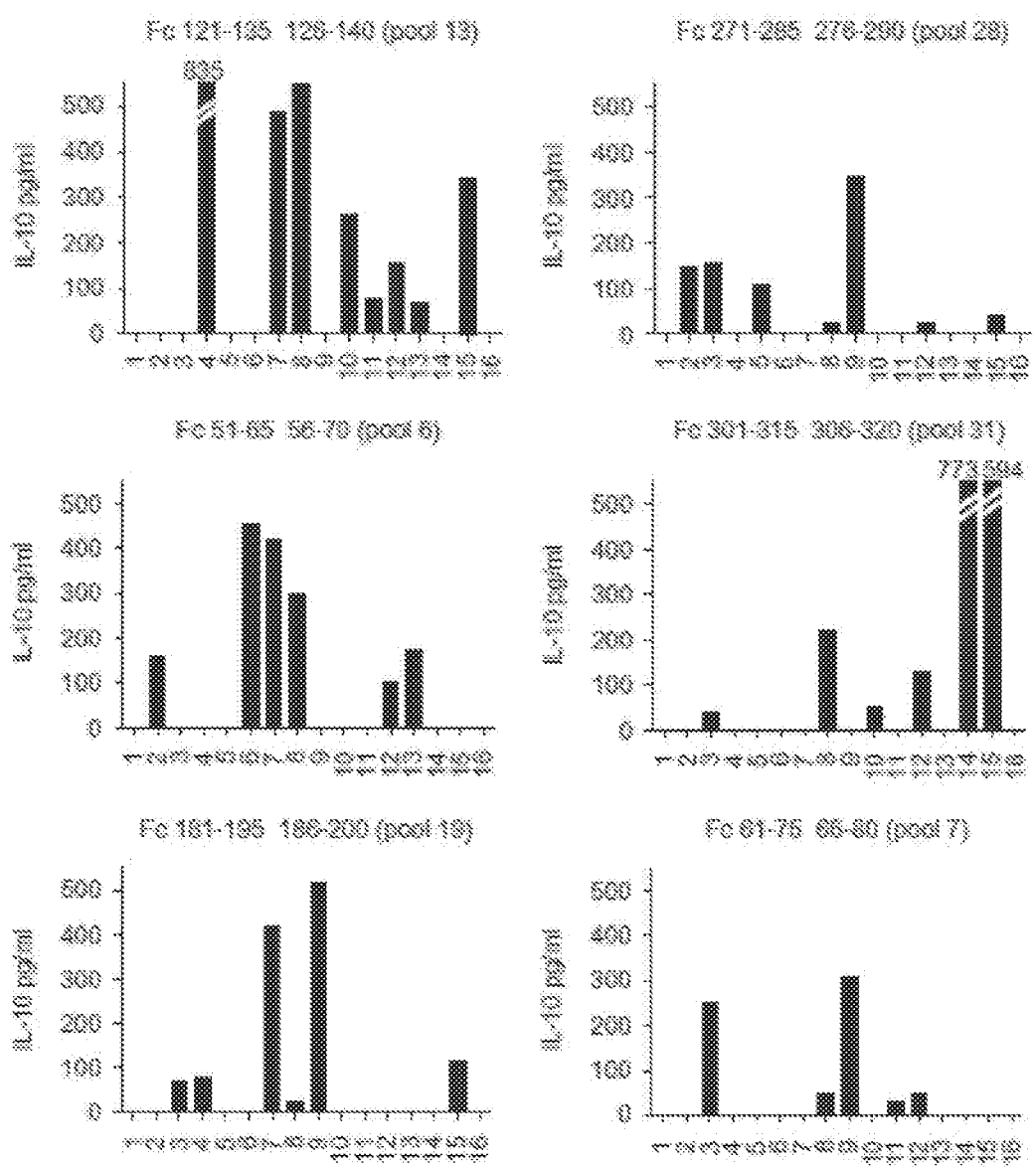

FIG. 14, or FIG. 1 of Example 3, graphically illustrates data showing nTreg fine specificities in sub-acute and convalescent KD subjects, where 2×10⁵ PBMC/well derived from 10 sub-acute and 6 convalescent KD subjects were cultured with pools of two Fc peptides (Table 3, see FIG. 13) for 4 days in the absence of exogenous lymphokines and IL-10 secretion (in pg/ml) in response to peptide stimulation was measured in culture supernatants by ELISA on day 4, as described in detail in Example 3, below.

Figure 2:
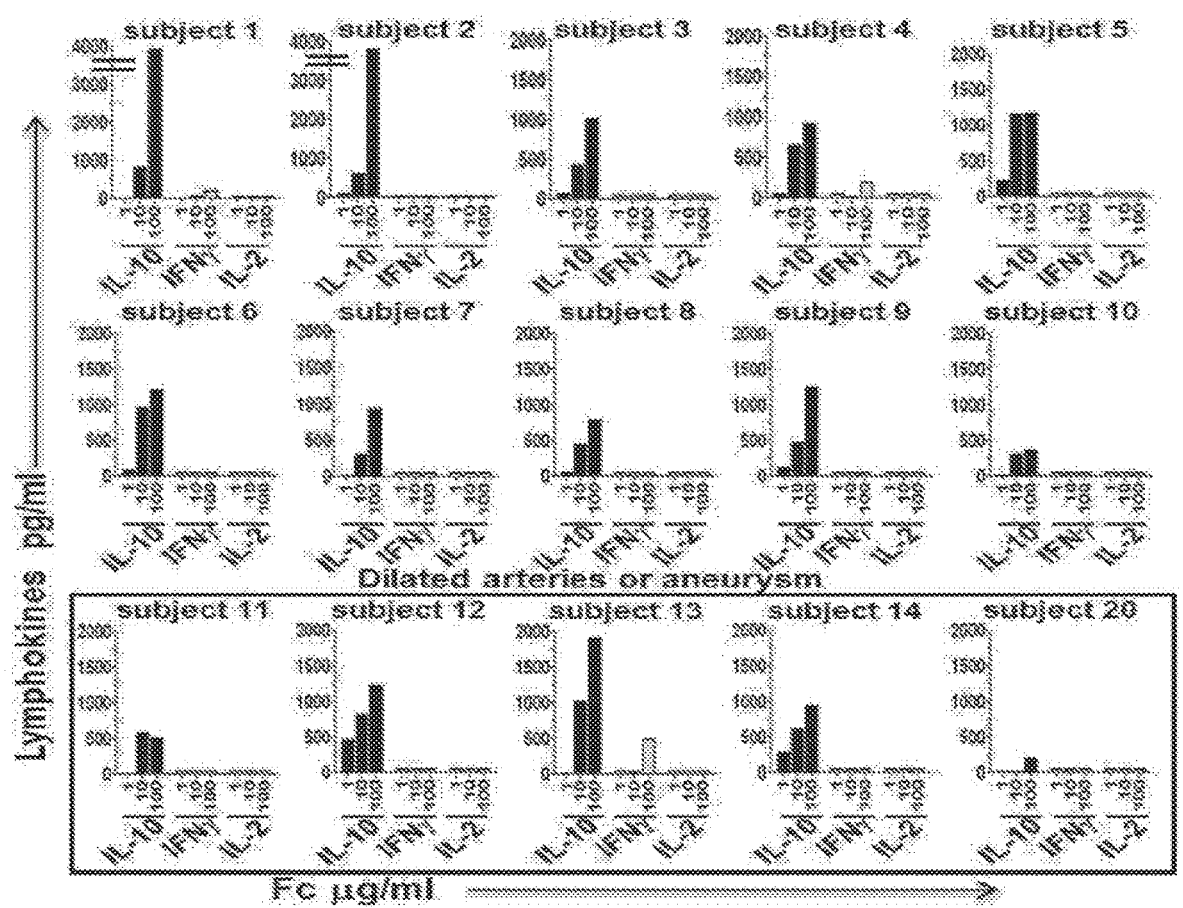
FIG. 2 graphically illustrates data of ELISA assays of supernatants harvested and tested for IL-10, IFN-gamma and IL-2 secretion from: PBMC derived from sub-acute KD subjects which secrete IL-10, but not IFN-gamma or IL-2 in response to scalar doses of Fc, PBMC from 15 KD subjects (10 with normal arteries after IVIG therapy and 5 with dilated arteries or aneurysm after IVIG therapy) cultured with scalar doses of purified Fc fragments for 4 days in the absence of exogenous lymphokines, as described in detail in Example 2, below.
Figure 15:
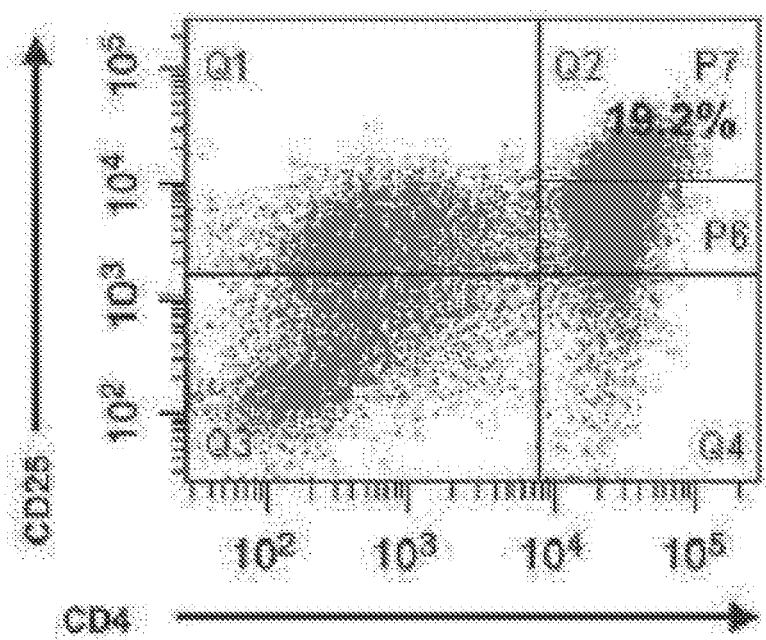

FIG. 15, or FIG. 2 of Example 3, graphically illustrates cell sorting data showing the response of nTreg to peptide pool 13; enumeration of CD4+CD25$^{high}$ T cells from KD subject #10 in response to Fc 121-135 and 126-140 (pool 13) is illustrated, and the most immunogenic sequences in this cohort of patients (P7, upper right), as described in detail in Example 3, below.

Figure 3B:
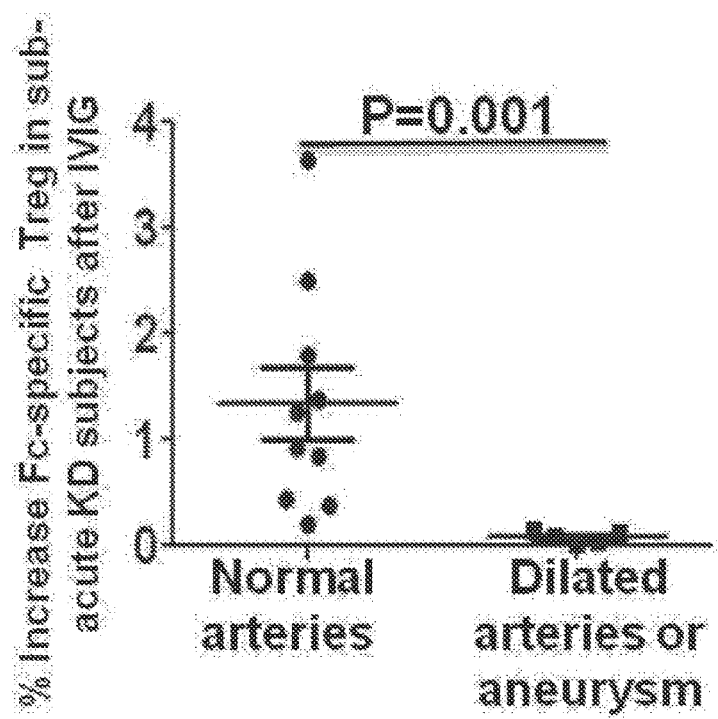
Figure 16:
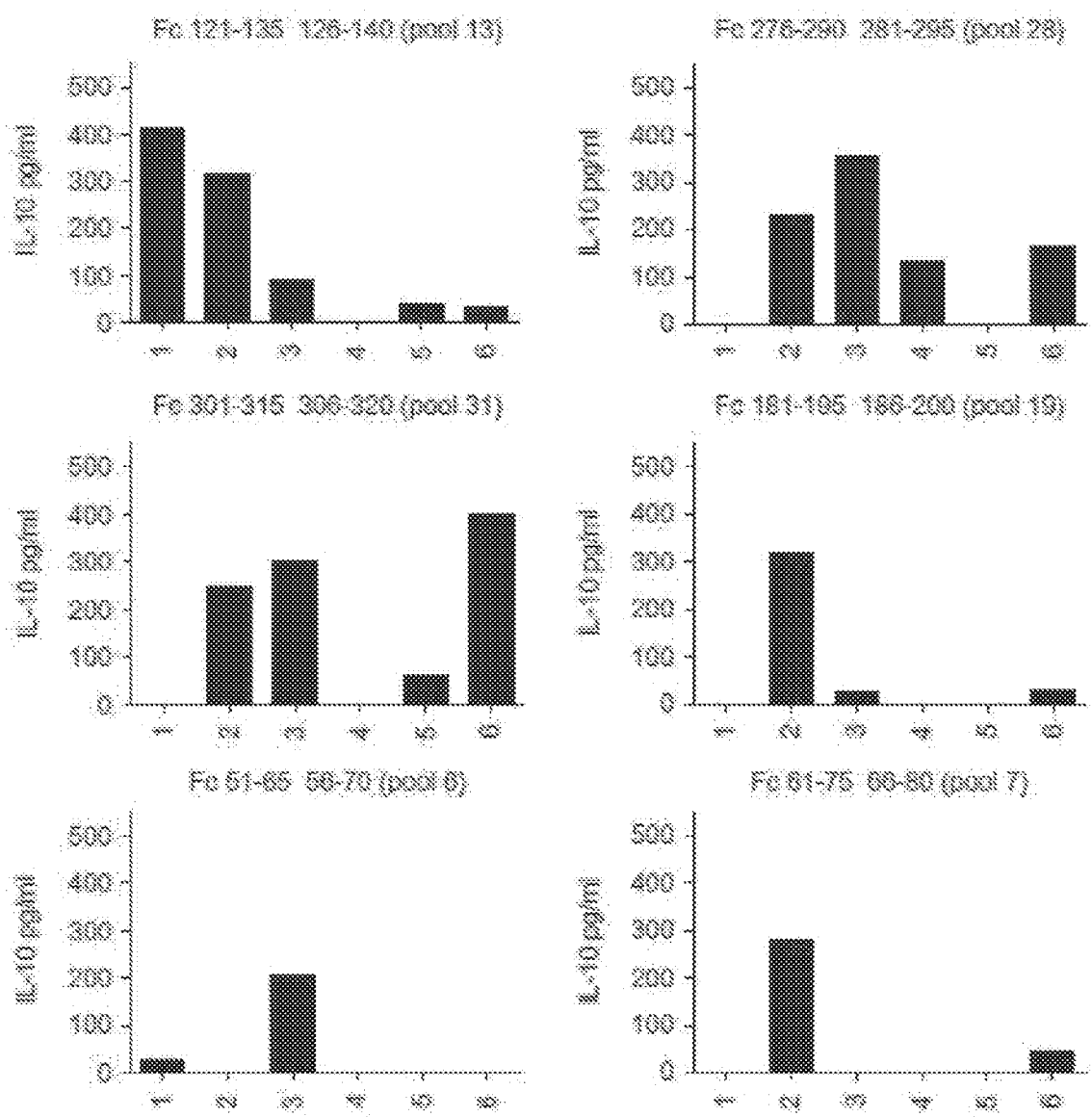

FIG. 16, or FIG. 3 of Example 3, graphically illustrates data showing that IL-10 secretion in PBMC cultures from healthy adult donors in response to peptide pools: 2×10⁵ PBMC/well derived from six healthy adult donors were cultured with pools of two Fc peptides (Table 3, see FIG. 13) for 4 days in the absence of exogenous lymphokines, and IL-10 secretion by nTreg in response to peptide stimulation served as a read out in these experiments and was measured in culture supernatants by ELISA on day 4, as described in detail in Example 3, below.

Figure 4:
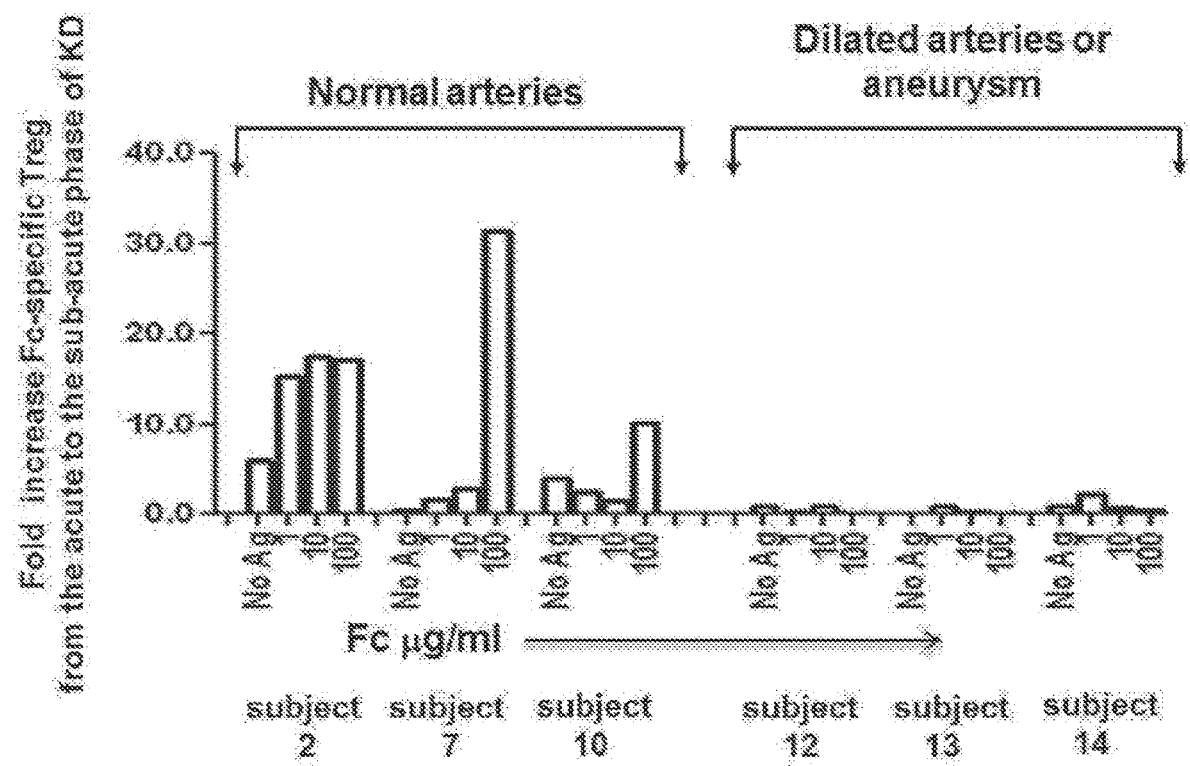
FIG. 4 graphically illustrates data showing the differential expansion of Fc-specific Treg from the acute to the sub-acute phase of KD depending upon clinical outcome, where the fold-increase of the Fc-specific Treg repertoire from the acute to sub-acute phase in 6 KD subjects was studied: three subjects with normal coronary arteries after IVIG therapy, three subjects with dilated arteries or aneurysm despite IVIG therapy, as described in detail in Example 2, below.
Figure 17A:
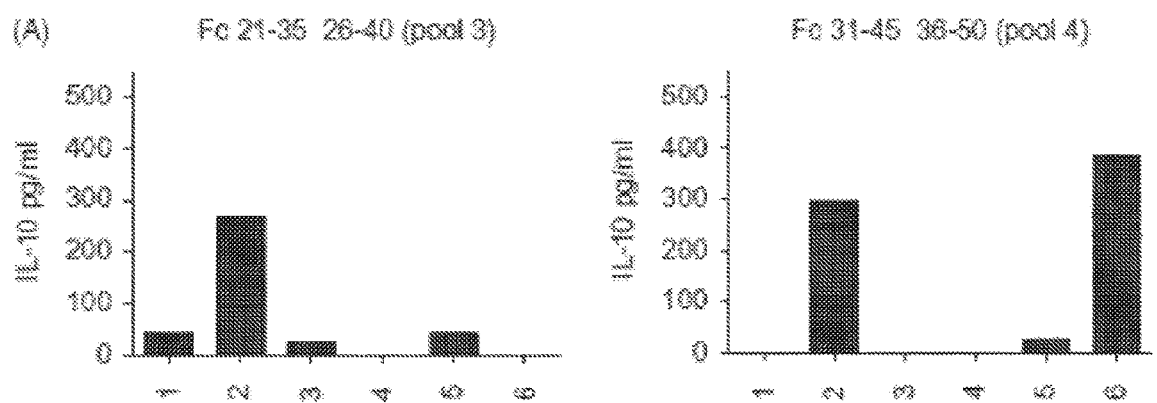
Figure 17B:
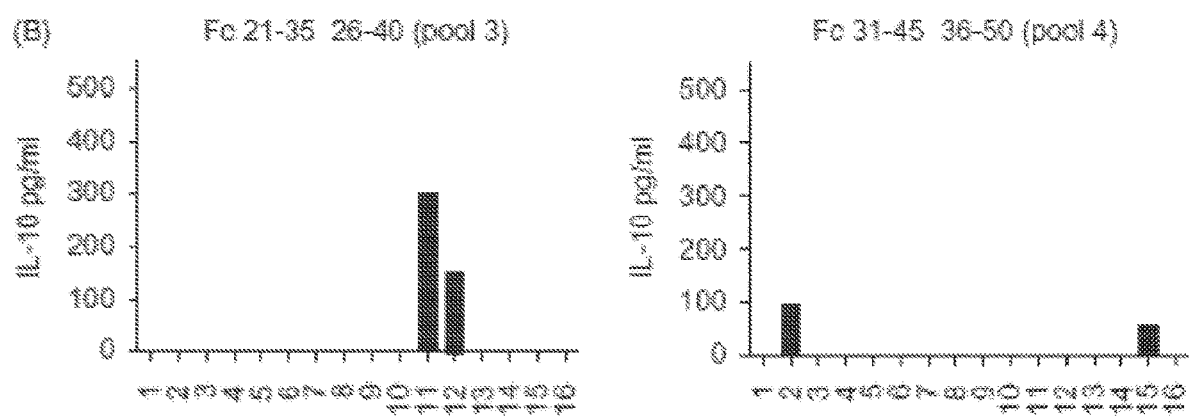

FIG. 17A and FIG. 17B, or FIG. 4 of Example 3, graphically illustrate data showing that pools 3 and 4 are more immunogenic in healthy donors than in KD patients: FIG. 17A: IL-10 secretion in response to amino acid residues 21-35 and 26-40 (pool 3) and 31-45 and 36-50 (pool 4) in healthy donors; FIG. 17B: nTreg responses to pools 3 and 4 in KD patients: only 2 of 12 KD subjects responded to these peptide pools, as described in detail in Example 3, below.

Figure 5:
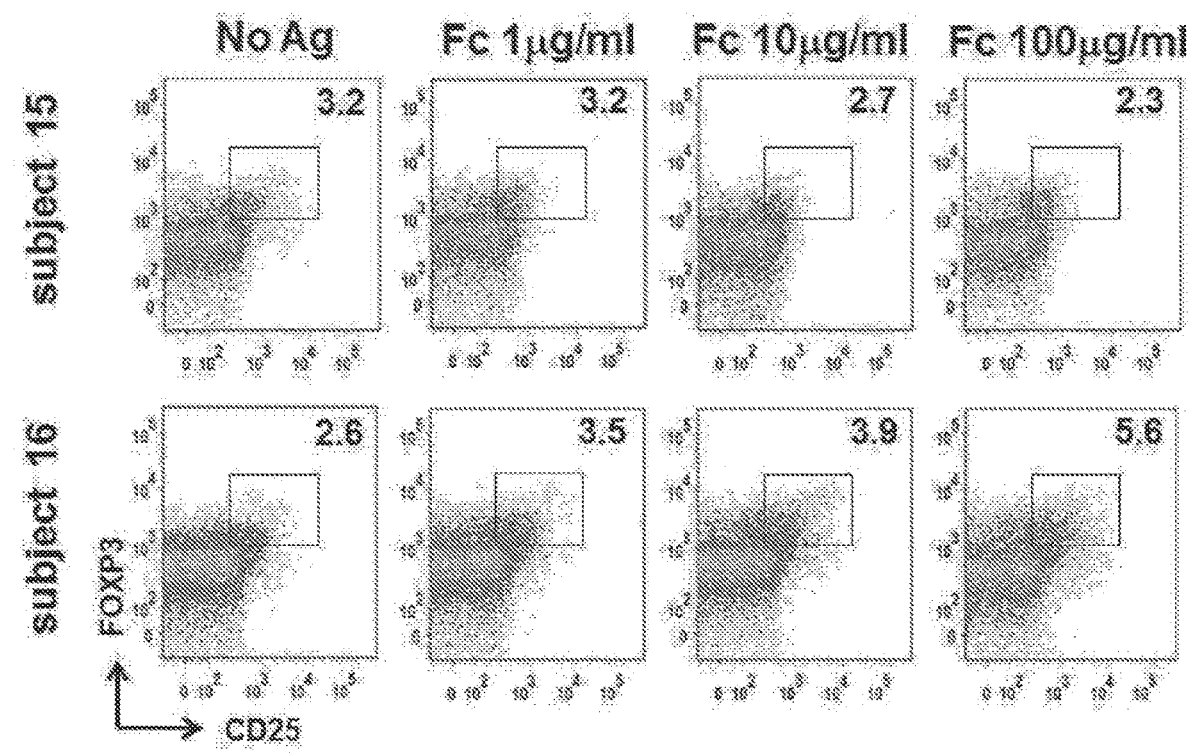
FIG. 5 graphically illustrates cell sorting data showing FOXP3+ T cells expansion in response to Fc: intracellular staining for FOXP3$^{high}$ expression in CD4+ T cells was assessed in Fc-stimulated PBMC cultures from two subacute patients after IVIG therapy, where "Subject 15" had dilated coronary arteries by echocardiogram; and "Subject 16" had normal coronary arteries and showed expansion of the Treg population in response to 100<g/ml Fc, as described in detail in Example 2, below.
Figure 18A:
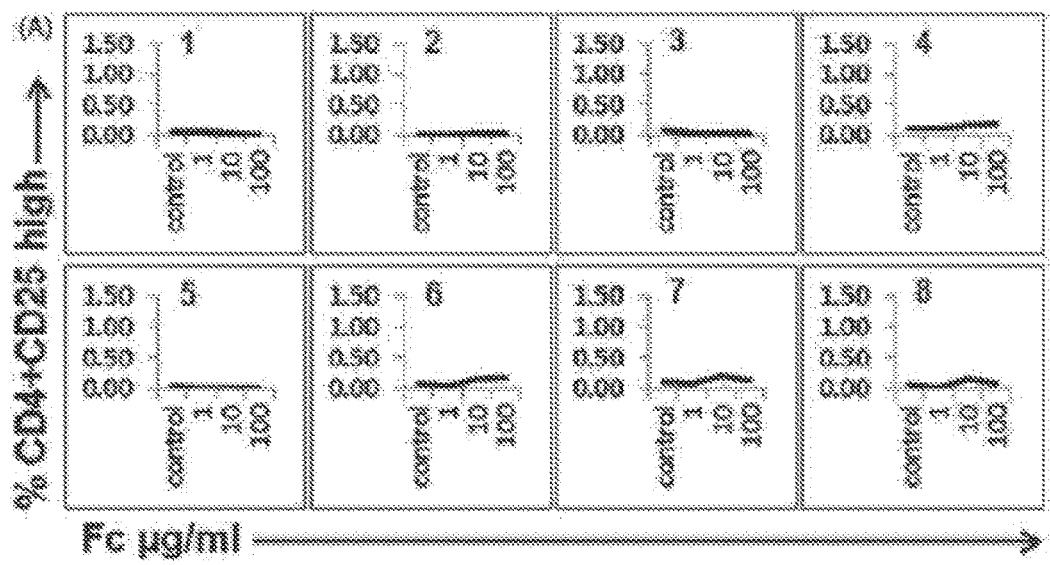
Figure 18B:
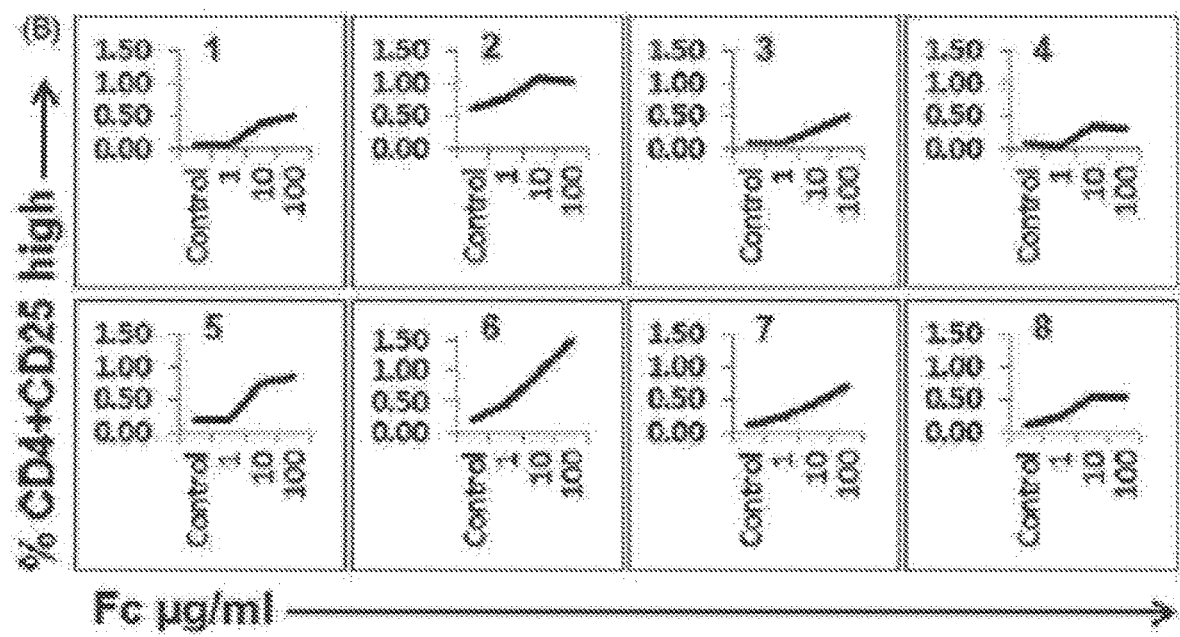

FIG. 18A and FIG. 18B, or FIG. 5 of Example 3, graphically illustrate data showing CD4+CD25$^{high}$ nTreg expansion in response to scalar doses of Fc; PBMC were cultured for 4 days with 0, 1, 10, or 100 µg/ml purified Fc fragments: FIG. 18A: Fc-specific nTreg response in adult subjects who had KD in childhood; FIG. 18B: Fc-specific nTreg response in healthy adult controls, as described in detail in Example 3, below.

Figure 6:
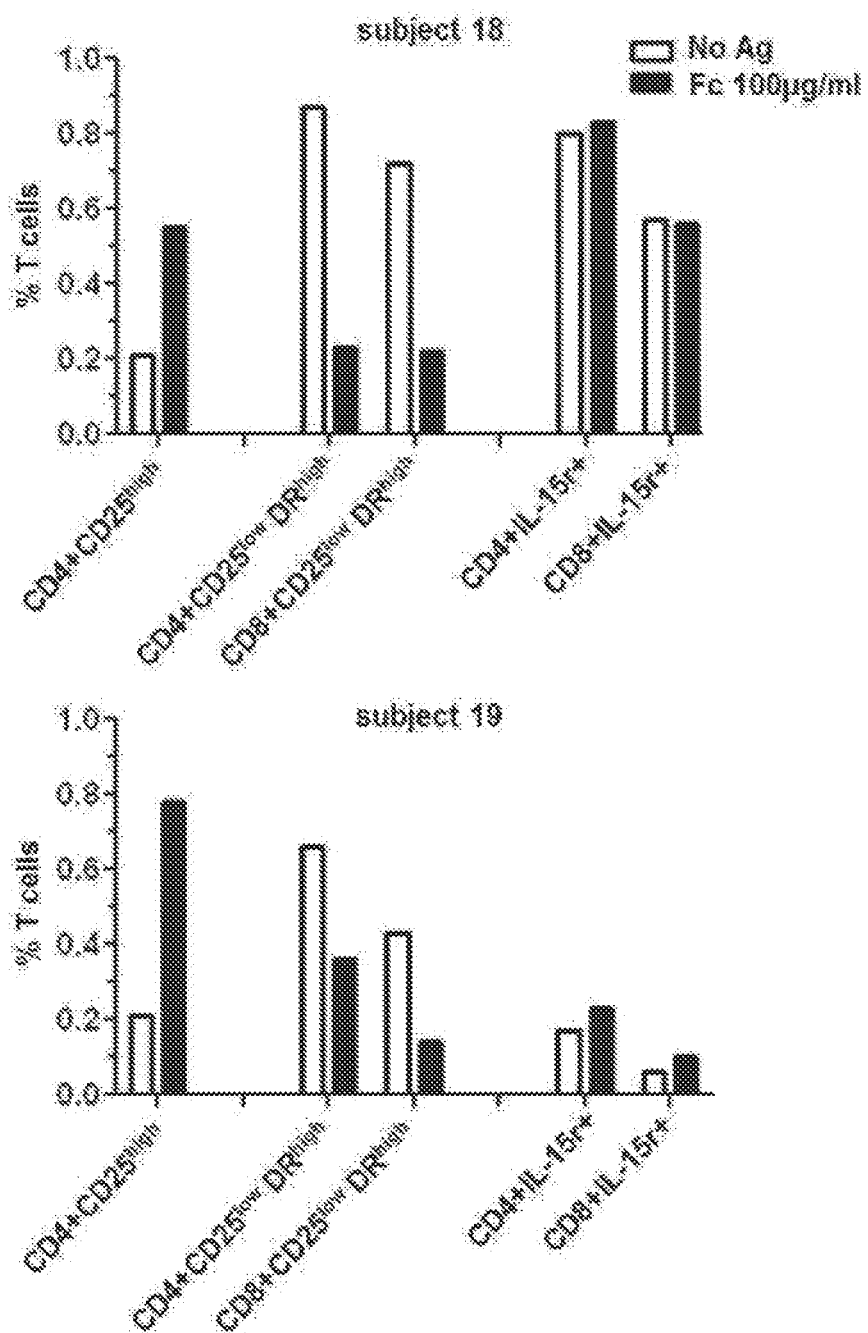
FIG. 6 graphically illustrates data showing activated CD4+ and CD8+CD25$^{low}$ DR$^{high}$ but not memory IL15r+ T cells decrease in PBMC cultured with Fc when Treg expand: PBMC from two sub-acute KD subjects with normal arteries after IVIG (Subject 18 is upper graphic illustration and Subject 19 is lower graphic illustration) were cultured with 100<g/ml purified Fc fragments or media alone as control to address the fate of activated T cells and memory T cells in Fc-stimulated cultures in which Treg expand. Treg were defined as CD4+CD25$^{high}$; activated CD4+ and CD8+ T cells as CD25$^{low}$ and DR$^{high}$; and memory T cells as IL-15r+, as described in detail in Example 2, below.
Figure 19:
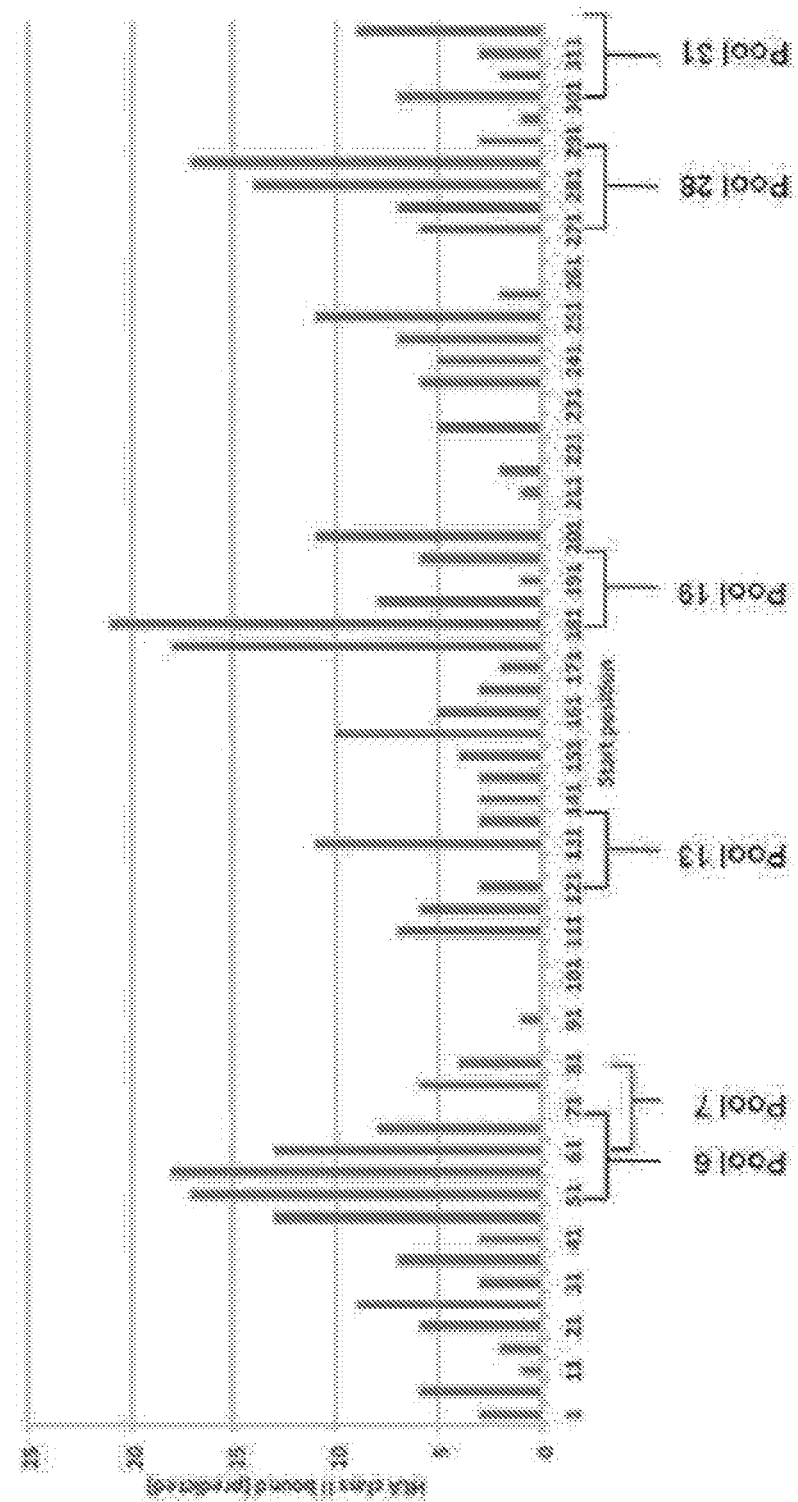

FIG. 19, or FIG. 6 of Example 3, graphically illustrates data showing HLA binding predictions of peptides derived from the Fc sequence; IEDB consensus algorithm was used to predict HLA class II binding affinity of the Fc sequences described in Table 3, see FIG. 13; and immunogenic peptide pools are indicated, as described in detail in Example 3, below.

Like reference symbols in the various drawings indicate like elements.

DETAILED DESCRIPTION

In alternative embodiments, provided are peptides and polypeptides, formulations and pharmaceutical compositions, and methods of using them, to generate immunogenic effects that help balance, or re-balance, the T cell repertoire in patients with, e.g., Kawasaki Disease and related vascular inflammations and cardiac conditions. In alternative embodiments, the immunogenic effect is to promote expansion of natural, regulatory T cells (nTregs) to establish, or re-establish, vascular homeostasis. In alternative embodiments, compositions and methods as provided herein are used as a substitute for, or as a complement to, intravenous (IV) immunoglobulin (Ig) (or WIG, or MG) therapy, particularly for Kawasaki disease (KD), but also more generally for the same or similar types of acute or chronic vascular inflammatory abnormalities. In alternative embodiments, compositions and methods as provided herein are used for treating, preventing or ameliorating: a disease or condition associated with an immune-mediated vascular disorder; a disease or condition that is currently treated with intravenous immunoglobulin (IVIG) therapy; a vascular coronary abnormality; an acute or a chronic vasculitis; an autoimmune inflammatory vasculitis; a T cell-mediated pediatric vasculitis; Kawasaki disease (KD); atherosclerosis; rheumatoid arthritis or Juvenile Idiopathic Arthritis; or, a neoplastic hematological disorder such as a lymphoma (e.g., a T cell lymphoma) or a leukemia.

The Fc protein (heavy region constant of IgG) is not recognized by nTreg in a fraction of patients, but the peptides as provided herein can rescue the nTreg response. While the invention is not limited by any particular mechanism of action, peptides and polypeptides as provided herein can overcome the problem of defective antigen processing and HLA binding that jeopardize nTreg responses to the Fc protein by directly stimulating anti-inflammatory nTregs. Thus, in alternative embodiments, compositions and methods provided herein are used as an "optimized" alternative to IVIG based on the immunodominant Fc peptides provided herein. Peptides and polypeptide provided herein can be stable, low cost and easy to administer.

In alternative embodiments, peptides and polypeptide provided herein are used (e.g., are administered) in incomplete adjuvants, e.g., analogous to the formulation of peptides that are in Phase III for the immunotherapy of a variety of tumors, as a peptide-based approach to induce immune-regulation.

In alternative embodiments, compositions as provided herein, including peptides and and polypeptide provided herein, formulations and pharmaceutical compositions, are used (e.g., are administered) as a peptide-based immunotherapy to raise immune-regulation via nTreg expansion, e.g., to treat, prevent, reverse, or ameliorate vascular diseases like, e.g., Kawasaki disease, or any disease or condition that is currently treated with IVIG or that is responsive to (e.g., is ameliorated or treated by) immune-regulation comprising suppression of pro-inflammatory T cells and/or suppression of pro-inflammatory T cell responses. In alternative embodiments, compositions as provided herein, including peptides, formulations and pharmaceutical compositions, are used (e.g., are administered) to treat, prevent, reverse or ameliorate any immune-mediated vascular disorder, e.g., atherosclerosis; rheumatoid arthritis or Juvenile Idiopathic Arthritis; or, a neoplastic hematological disorder such as a lymphoma (e.g., a T cell lymphoma) or a leukemia. While the invention is not limited by any particular mechanism of action, patients with Juvenile Idiopathic Arthritis lack Fc-specific nTreg, and including peptides, formulations and pharmaceutical compositions (e.g., immunodominant Fc peptides as provided herein) can by-pass lack of specific T cell-mediated regulation in a variety of clinical settings.

Intravenous immunoglobulin therapy (IVIG) is the treatment of choice for many immune-mediated diseases, yet its mechanisms of action are incompletely elucidated. We investigated the possibility that IVIG played a direct role in the expansion of regulatory T cells (Treg) that recognize the heavy chain constant region of immunoglobulin G (Fc) as a mechanism for the recovery of Kawasaki disease or a pediatric acute vasculitis of the coronary arteries, e.g., a T cell mediated pediatric vasculitis of the coronary arteries. We successfully generated Fe-specific Treg clones from sub-acute KD subjects that did not develop arterial complications after IVIG and defined an unusual functional phenotype: Fc-specific Treg secrete IL-10 and small amounts of IL-4 but not TGF-β. Antigen presentation studies demonstrated that these Treg clones can be activated by autologous B cells that express IgG on their cell surface in the absence of exogenous Fc. The IgG molecule has to be canonically processed and presented by autologous MHC molecules to be recognized by Treg. In support of the importance of this novel Treg population in downsizing vascular inflammation, KD patients with dilated coronary arteries or aneurysms despite IVIG treatment failed to expand Fc-specific Treg. Our results point to a specificity of a previously un-described Treg population for the clinical benefit provided by IVIG therapy in children.

Peptides and Polypeptides

In alternative embodiments, peptides or polypeptides as provided herein or peptides or polypeptides used to practice methods or uses as provided herein comprise a recombinant protein, a synthetic protein, a peptidomimetic, a non-natural peptide, or a combination thereof. Peptides and proteins used to practice compositions, methods and uses as provided herein can be recombinantly expressed in vitro or in vivo. The peptides and polypeptides as provided herein can be made and isolated using any method known in the art as well as using the methods described herein. Polypeptide and peptides provided herein or for practicing methods and uses as provided herein can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) including any automated polypeptide synthesis process known in the art.

In alternative embodiments, peptides as provided herein or peptides used to practice methods or uses as provided herein are synthetic molecules including, e.g., peptidomimetics and non-natural amino acids. In alternative aspects, peptides and polypeptide provided herein comprise amino acids joined to each other by peptide bonds or modified peptide bonds and may comprise modified amino acids other than the 20 gene-encoded amino acids.

In alternative embodiments, peptides as provided herein or peptides used to practice methods or uses as provided herein have many types of modifications, e.g., modifications including glycosylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, phosphorylation, prenylation, racemization, selenoylation, sulfation and transfer-RNA mediated addition of amino acids to protein such as arginylation. See for example, Creighton, T. E., Proteins—Structure and Molecular Properties 2nd Ed., W.H. Freeman and Company, N Y (1993); Posttranslational Covalent Modification of Proteins, B. C. Johnson, Ed., Academic Press, NY, pp. 1-12 (1983)). In another embodiment, a DRP can be glycol-pegylated as described in U.S. Pat. No. 7,405,198; or can be glycosylated as described in U.S. Pat. No. 7,276,475 or 7,399,613, or 7,338,933, the later describing O-linked glycosylation of peptides. Peptides as provided herein or peptides used to practice methods or uses as provided herein can be acylated as described e.g., in U.S. Pat. No. 7,273,921.

In alternative embodiments, peptides as provided herein or peptides used to practice methods or uses as provided herein can comprise any "mimetic" and/or "peptidomimetic" form. In alternative embodiments, peptides as provided herein or peptides used to practice methods or uses as provided herein comprise synthetic chemical compounds which have substantially the same structural and/or functional characteristics of natural or non-natural peptides. A mimetic provided herein can be either entirely composed of synthetic, non-natural analogues of amino acids, or, is a chimeric molecule of partly natural peptide amino acids and partly non-natural analogs of amino acids. A mimetic used to practice compositions, methods or uses as provided herein can also incorporate any amount of natural or non-natural amino acid conservative substitutions as long as such substitutions also do not substantially alter the mimetic's structure and/or activity.

Routine experimentation will determine whether a synthetic molecule or mimetic is effective for practicing a composition, method or use as provided herein, e.g., for effecting immune-regulation by expanding natural regulatory T cells (nTregs) or nTreg suppression of pro-inflammatory T cells and/or pro-inflammatory T cell responses. Methodologies detailed herein and others known to persons skilled in the art may be used to select or guide one to choose effective mimetic for practicing the compositions and/or methods as provided herein.

Polypeptide mimetic compositions for practicing compositions, methods or uses as provided herein can comprise any combination of non-natural structural components. In alternative aspects, mimetic compositions for practicing compositions, methods or uses as provided herein can comprise one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY). A polypeptide can also be characterized as a mimetic by containing all or some non-natural residues in place of naturally occurring amino acid residues. Nonnatural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; D- or L-p-methoxy-biphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids used to practice methods or uses as provided herein can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, e.g., under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alphahaloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics that can be used include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

Peptides used to practice methods or uses as provided herein can comprise tags or signal sequences, i.e., leader sequences, e.g., for identifying or secreting a peptide or a polypeptide provided herein from a production host cell. In one embodiment, a cleavable linker is placed between the signal sequence or tag and the peptide or a polypeptide provided herein.

Generating and Manipulating Nucleic Acids

In alternative aspects, because the peptides as provided herein or peptides used to practice methods or uses as provided herein can be used in recombinant form, also provided are nucleic acids, which themselves can be recombinant, to make them. In alternative embodiments, nucleic acids s provided herein or nucleic acids used to practice methods or uses as provided herein are made, isolated and/or manipulated by, e.g., cloning and expression of cDNA libraries, amplification of message or genomic DNA by PCR, and the like.

The nucleic acids provided herein or nucleic acids used to practice methods or uses as provided herein, whether RNA, cDNA, genomic DNA, vectors, viruses or hybrids thereof, can be isolated from a variety of sources, genetically engineered, amplified, and/or expressed/generated recombinantly. Recombinant polypeptides (e.g., a peptide used to practice a method or use as provided herein) generated from these nucleic acids can be individually isolated or cloned and tested for a desired activity. Any recombinant expression system can be used, including e.g. in vitro, bacterial, fungal, mammalian, yeast, insect or plant cell expression systems.

In one embodiment, nucleic acids s provided herein or nucleic acids used to practice methods or uses as provided herein are synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids s provided herein or nucleic acids used to practice methods or uses as provided herein, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Also provided are fusion proteins and nucleic acids encoding them, and uses thereof. Any peptide used to practice methods and uses as provided herein can be fused to a heterologous peptide or polypeptide. In alternative embodiments, a heterologous peptide or polypeptide joined or fused to a protein used to practice methods and uses as provided herein can be an N-terminal identification peptide which imparts a desired characteristic, such as fluorescent detection, increased stability and/or simplified purification.

Peptides used to practice methods and uses as provided herein can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Pharmaceutical Compositions and Formulations

Provided are pharmaceutical compositions and formulations comprising peptides and polypeptide as provided herein for treating, preventing, reversing or ameliorating: a disease or condition associated with an immune-mediated vascular disorder; a disease or condition that is currently treated with intravenous immunoglobulin (IVIG) therapy; a vascular coronary abnormality; an acute or a chronic vasculitis; an autoimmune inflammatory vasculitis; a T cell mediated pediatric vasculitis; Kawasaki disease or a pediatric acute vasculitis of the coronary arteries; atherosclerosis; rheumatoid arthritis or Juvenile Idiopathic Arthritis; an immune disease or condition; or, a neoplastic hematological disorder such as a lymphoma (e.g., a T cell lymphoma) or a leukemia.

In alternative embodiments, the compositions as provided herein are formulated with a pharmaceutically acceptable carrier. In alternative embodiments, the pharmaceutical compositions and formulations as provided herein can be administered parenterally, topically, orally or by local administration, such as by aerosol or transdermally. The pharmaceutical compositions can be formulated in any way and can be administered in a variety of unit dosage forms depending upon the condition or disease (e.g., type of acute or chronic vasculitides) and the degree of illness, the general medical condition of each patient, the resulting preferred method of administration and the like. Details on techniques for formulation and administration of pharmaceuticals and peptides are well described in the scientific and patent literature, see, e.g., the latest edition of Remington's Pharmaceutical Sciences, Maack Publishing Co, Easton Pa. ("Remington's").

Peptides as provided herein can be administered alone or as a component of a pharmaceutical formulation (composition). The compounds may be formulated for administration, e.g., as a peptide, in any convenient way for use in human or veterinary medicine. Wetting agents, incomplete adjuvants, emulsifiers and lubricants, such as sodium lauryl sulfate and magnesium stearate, as well as coloring agents, release agents, coating agents, sweetening, flavoring and perfuming agents, preservatives and antioxidants can also be present in the compositions e.g., peptide formulations.

Formulations or compositions as provided herein, e.g., peptide formulations, include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., a peptide as provided herein) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations as provided herein, e.g., peptide formulations, can be prepared according to any method known to the art for the manufacture of pharmaceuticals or peptides. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions, e.g., peptide formulations, can contain an active agent (e.g., a peptide or peptidomimetic as provided herein) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In one embodiment, oil-based pharmaceuticals are used for administration of hydrophobic peptides as provided herein. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations, e.g., peptide formulations, as provided herein can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In one embodiment, peptides as provided herein are formulated as oil-in-water emulsions as described in U.S. Pat. No. 7,371,395, describing an injectable oil-in-water emulsion, comprising an aqueous solution containing at least one peptides as provided herein, a mineral oil, a non-ionic lipophilic surfactant and/or a non-ionic hydrophilic surfactant having a high hydrophilic-lipophilic balance (HLB) value. In alternative embodiments, these injectable oil-in-water emulsions as provided herein comprise a paraffin oil, a sorbitan monooleate, an ethoxylated sorbitan monooleate and/or an ethoxylated sorbitan trioleate.

In practicing methods and uses as provided herein, the pharmaceutical compounds, e.g., peptide formulations, can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing methods and uses as provided herein, the pharmaceutical compounds, e.g., peptide formulations, can be delivered by transdermally, by a topical route, formulated as applicator sticks, solutions, suspensions, emulsions, gels, creams, ointments, pastes, jellies, paints, powders, and aerosols.

In practicing methods and uses as provided herein, the pharmaceutical compounds, e.g., peptide formulations, can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In practicing methods and uses as provided herein, the pharmaceutical compounds, e.g., peptide formulations, can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations, e.g., peptide formulations, as provided herein can be lyophilized. Provided are a stable lyophilized formulation comprising a composition as provided herein, which can be made by lyophilizing a solution comprising a pharmaceutical as provided herein and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations, e.g., peptide formulations, as provided herein can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations and pharmaceuticals as provided herein can be administered for prophylactic and/or therapeutic treatments. In alternative embodiments, for therapeutic applications, compositions are administered to a subject already suffering from a condition; this can be called a "therapeutically effective amount". For example, in alternative embodiments, pharmaceutical compositions as provided herein are administered in an amount sufficient to generate immune-regulation by expanding natural regulatory T cells (nTregs) or nTreg suppression of pro-inflammatory T cells and/or pro-inflammatory T cell responses. The amount of pharmaceutical composition adequate to accomplish this is defined as a "therapeutically effective dose." The dosage schedule and amounts effective for this use, i.e., the "dosing regimen," will depend upon a variety of factors, including the stage of the disease (e.g., a disease or condition associated with an immune-mediated vascular disorder) or condition, the severity of the disease or condition, the general state of the patient's health, the patient's physical status, age and the like. In calculating the dosage regimen (e.g., peptide administration regimen) for a patient, the mode of administration also is taken into consideration, e.g., intradermal injection of peptide formulation.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods are uses as provided herein are correct and appropriate.

Single or multiple administrations of formulations, e.g., peptide formulations, can be given depending on for example: the dosage and frequency as required and tolerated by the patient, the degree and amount of antigen specific CTLs and/or T helper cells, or antigen-specific antibodies, generated after each peptide administration, and the like. The formulations should provide a sufficient quantity of active agent to effectively treat, prevent or ameliorate a conditions, diseases or symptoms, e.g., generate immune-regulation by expanding natural regulatory T cells (nTregs) or nTreg suppression of pro-inflammatory T cells and/or pro-inflammatory T cell responses.

In alternative embodiments, pharmaceutical formulations, e.g., peptide formulations, for oral administration are in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods and uses as provided herein can further comprise co-administration with other drugs or pharmaceuticals, e.g., compositions for treating cancer, septic shock, infection, fever, pain and related symptoms or conditions. For example, the methods, uses and/or compositions and formulations as provided herein can be co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Formulations

Provided are polypeptide and peptide formulations and methods for making and using them. In alternative embodiments, peptides as provided herein are formulated as aqueous solutions and administered intradermally as peptides.

In alternative embodiments, the peptide is conjugated or linked to another peptide or administered with another protein, such as a carrier protein or immunogenic protein. Such factors are known in the art and it is well within the skill of physicians and immunologists to make such determinations.

The peptide active agent can be present in a formulation as provided herein in varying concentrations, e.g., in one embodiment the minimum concentration of peptide is an amount necessary to generate immune-regulation by expanding natural regulatory T cells (nTregs) or nTreg suppression of pro-inflammatory T cells and/or pro-inflammatory T cell responses, while the maximum concentration is the maximum amount that will remain in solution or homogeneously suspended within the initial mixture. In alternative embodiments, the minimum concentration of peptide is an amount necessary to generate immune-regulation by expanding natural regulatory T cells (nTregs) or nTreg suppression of pro-inflammatory T cells and/or pro-inflammatory T cell responses, and the maximum concentration is the point at which a homogeneous suspension cannot be maintained. In alternative embodiments, doses can comprise 1 to 100 µg of protein antigen, or 5 to 50 µg, or 5 to 25 µg. A desired amount of peptide varies from formulation to formulation, or application to application (e.g., form of vasculitis) but is easily determinable by one of skill in the art. Peptide preparation is well known in the art, see e.g., Peptide Design ("The subunit and adjuvant approach" Eds. Powell M. F. & Newman M. J. (1995) Plenum Press New York).

Methods of delivering the peptide are also well known in the art. For example, in alternative embodiments peptides as provided herein are formulated and delivered via a parenteral route comprising or consisting of a subcutaneous, an intravenous (IV), an intradermal, an intramuscular, an intraperitoneal, an intranasal, a transdermal or a buccal route.

In alternative embodiments peptides as provided herein are delivered intradermally or intra-epidermally using any needle-like structures or device, e.g., as described in U.S. Patent App. Pub. No. 20090012494, describing use of microneedle devices, e.g., with rows of hollow microneedles. In alternative embodiments peptides as provided herein are delivered using micro-cannula, e.g., as described in U.S. Pat. No. 7,473,247. When using this or another device or needle to practice methods and uses as provided herein, peptide formulations can be directly targeted into an intradermal space; or can be delivered into an intradermal space as a bolus or by infusion. In alternative embodiments, "intradermal" is administration of a peptide formulation as provided herein into the dermis in such a manner that the peptide as provided herein therein readily reaches the richly vascularized papillary dermis where it can be rapidly systemically absorbed, or the peptide can be taken up directly by cells (e.g., dendritic cells) in the skin. In alternative embodiments, "intradermal" includes every layer of the skin, including stratum corneum, epidermis and dermis.

In one embodiment, a drug-delivery patch is used to deliver a peptide formulation as provided herein, e.g., as described in U.S. Patent App. Pub. No. 20090010998. In one embodiment, provided is a drug-delivery patch having at least one dissolvable layer comprising a peptide as provided herein and an adhesive backing or cover. In one embodiment, an individual is transdermally vaccinated by ablating an area of the stratum corneum of the individual and applying the patch to that area.

Methods for determining the efficacy of a peptide formulation as provided herein, or a particular administration of a peptide formulation as provided herein, are well known in the art. For example, cell-based or humoral responses can be assessed (measured) using in vitro based assays and/or in vivo based assays, including animal based assays. Assays for measuring cell-based or humoral immune response are well known in the art, e.g., see, Coligan et al., (eds.), 1997, Current Protocols in Immunology, John Wiley and Sons, Inc. Cell-based or humoral immune responses may be detected and/or quantitated using standard methods known in the art including, e.g., an ELISA assay, chromium release assays and the like. The humoral immune response may be measured by detecting and/or quantitating the relative amount of an antibody which specifically recognizes an antigenic or immunogenic agent in the sera of a subject who has been treated with a peptide formulation as provided herein relative to the amount of the antibody in an untreated subject. ELISA assays can be used to determine total antibody titers in a sample obtained from a subject treated with an agent as provided herein.

Kits and Packages

Provided are kits, packets and packages comprising compositions and cells (e.g., dendritic cells) as provided herein and, in some aspects, instructions for practicing methods and uses as provided herein, including the peptide formulations or drug-delivery patches as provided herein. In alternative embodiments, storage devices, such as vials, and peptide delivery devices such as drug-delivery patches comprising peptide formulations as provided herein are provided herein.

These and many other variations and embodiments as provided herein will be apparent to one of skill in the art upon a review of the appended description and examples. The invention will be further described with reference to the following examples; however, it is to be understood that the invention is not limited to such examples.

EXAMPLES

Example 1: Peptides Effective for Expanding Regulatory T Cells (Treg) Populations This example presents data demonstrating that compositions as provided herein effectively expand regulatory T cells (Treg) populations for, e.g., ameliorating vascular inflammation, and Kawasaki disease or a pediatric acute vasculitis of the coronary arteries, including vascular coronary abnormalities and the same or similar types of acute or chronic vascular inflammatory abnormalities. Peptides as provided herein can be recognized by nTreg without further antigen processing.

Fc-specific nTregs can suppress pro-inflammatory T cells and pro-inflammatory T cell responses. To define the fine specificity of nTreg after IVIG for therapeutic purposes, we developed a panel of peptides 15 amino acid long, overlapping 10 amino acids, that cover the whole (entire) Fc sequences.

We successfully identified in vitro a panel of unique Fc sequences never reported before that generate nTreg not only in KD patients that do not develop arterial complications after IVIG but also in patients that develop arterial complication and do not respond to the whole Fc protein by expanding specific nTreg:

```
1. Fc sequence 21-35
                                  (SEQ ID NO: 1)
   TAALGCLVKDYFPEP 2. Fc sequence 26-40
                                  (SEQ ID NO: 2)
   CLVKDYFPEPVTVSW 3. Fc sequence 121-135
                                  (SEQ ID NO: 3)
   SVFLFPPKPKDTLMI 4. Fc sequence 126-140
                                  (SEQ ID NO: 4)
   PPKPKDTLMISRTPE
```

-continued

5. Fc sequence 291-305
(SEQ ID NO: 5)
KLTVDKSRWQQGNVF

6. Fc sequence 296-310
(SEQ ID NO: 6)
KSRWQQGNVFSCSVM

7. Fc sequence 266-280
(SEQ ID NO: 7)
NGQPENNYKTTPPVL

8. Fc sequence 271-285
(SEQ ID NO: 8)
NNYKTTPPVLDSDGS

Fc sequence 276-290
(SEQ ID NO: 15)
TPPVLDSDGSFFLYS

Fc sequence 301-315
(SEQ ID NO: 16)
QGNVFSCSVMHEALH

Fc sequence 306-320
(SEQ ID NO: 17)
SCSVMHEALHNHYTQ

Within peptides 9 to 12 some amino acids are included within the Tregitopes previously published:

9. Fc sequence 51-65
(SEQ ID NO: 9)
TFPAVLQSSGLYSLS
(sequence included in Tregitope 167)

10. Fc sequence 56-70
(SEQ ID NO: 10)
LQSSGLYSLSSVVTV
(sequence included in Tregitope 167)

11. Fc sequence 61-75
(SEQ ID NO: 11)
LYSLSSVVTVPSSSL
(sequence included in Tregitope 167)

12. Fc sequence 66-80
(SEQ ID NO: 12)
SVVTVPSSSLGTQTY
(sequence included in Tregitope 167)

13. Fc sequence 176-190
(SEQ ID NO: 13)
EQYNSTYRVVSVLTV
(sequence included in Tregitope 289)

14. Fc sequence 181-195
(SEQ ID NO: 14)
TYRVVSVLTVLHQDW
(sequence included in Tregitope 289).

These exemplary immunodominant Fc peptides as provided herein have been identified in three chohorts of subjects:

1) Kawasaki disease sub-acute patients 2 weeks after IVIG;
2) Patients that had Kawasaki disease 1-2 year earlier treated with IVIG;
3) Healthy donors that never received IVIG.

These unique sequences are recognized by nTreg in the large majority of the patients studied after IVIG, KD patients treated with WIG 1 to 2 years earlier and normal healthy controls that did not receive IVIG.

Kawasaki Disease (KD) patients with arterial complication do not respond to the whole Fc protein but they do respond to 15 mers Fc peptides as provided herein, as illustrated in FIG. 1. Notably, the immunodominant Fc peptides recognized by nTreg in KD patients after IVIG are the same as the one recognized by nTreg in normal healthy donors, suggesting that the sequences identified are universal.

Figure 1B:
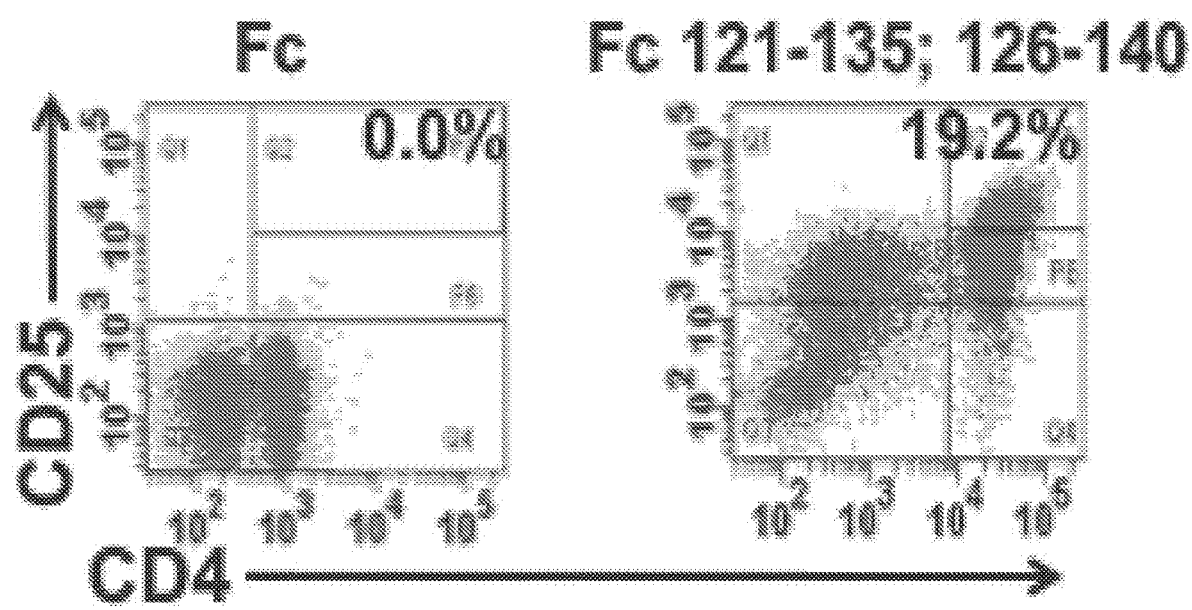

FIG. 1 of Example 1 illustrates data from Fc peptide epitope mapping in 3 healthy adult donors and 3 Kawasaki disease (KD) patients with arterial complication who do not respond to the whole Fc protein but the KD patients do respond to 15 mers Fc peptides as provided herein after IVIG. PBMC were cultured with Fc peptides (as described above) for 4 days in the absence of lymphokines. FIG. 1A graphically illustrates: IL-10 secretion by peptide-specific Treg; Treg lines from the KD patient with coronary artery aneurysm (CAA) are shown as KD 3873, right-hand-most graphic column in "KD Sub-Acute" side of the figure. FIG. 1B graphically illustrates a representative enumeration of a cell sorting scan of CD4+CD25$^{high}$ T cells in response to the whole Fc and peptide pool 121-135; 126-140 in PBMC cultures from a CAA+KD subject with aneurysms.

Example 2: Treg Populations Effective for Resolving Vascular Inflammation

This example describes a novel Treg population that specifically recognizes the Fc of IgG presented by autologous mature IgG+ B lymphocytes, that expands following IVIG infusion, and that is distinct from the previously described Treg that recognize exogenous pan-DR Fc epitopes in normal healthy donors (24). Expansion of this Fc-specific Treg population is associated with resolution of vascular inflammation, while failure to expand is associated with progressive damage to the vascular wall and coronary artery aneurysm formation in infants and young children with KD.

Materials and Methods

Study Population

KD patients and pediatric patients with acute inflammatory conditions were enrolled at Rady Children's Hospital San Diego following parental informed consent. The protocol was approved by the Institutional Review Board at UCSD. All KD patients enrolled in this study (Table 1) were evaluated by echocardiography during the acute admission and at two and six weeks following diagnosis.

TABLE 1

KD subjects enrolled in the study.

| KD subject # | Age, yrs | Sex | Race/Ethnicity | Illness day[a] | Coronary artery Z-max[b] | Fc-specific Treg response |
|---|---|---|---|---|---|---|
| 1 | 1.4 | M | Hispanic | 4 | 0.8 | + |
| 2 | 5.4 | F | Caucasian/Asian | 5 | 0.7 | + |
| 3 | 0.6 | M | Hispanic/Asian | 6 | 1.4 | + |
| 4 | 2.0 | M | Caucasian/Hispanic/Native American | 8 | 1.7 | + |
| 5 | 5.8 | F | Hispanic | 5 | 1.1 | + |

TABLE 1-continued

KD subjects enrolled in the study.

| KD subject # | Age, yrs | Sex | Race/Ethnicity | Illness day[a] | Coronary artery Z-max[b] | Fc-specific Treg response |
|---|---|---|---|---|---|---|
| 6 | 5.3 | M | Caucasian | 5 | 1.2 | + |
| 7 | 0.3 | M | Asian | 3 | 1.2 | + |
| 8 | 3.7 | M | Caucasian | 8 | 0.9 | + |
| 9 | 6.9 | M | Caucasian | 6 | 1.0 | + |
| 10 | 2.9 | M | Hispanic | 7 | 1.6 | + |
| 11 | 1.9 | M | Caucasian | 4 | 3.3 (dilated) | − |
| 12 | 7.9 | M | Hispanic | 4 | 2.8 (dilated) | − |
| 13 | 2.0 | F | Mixed | 8 | 4.7 (anearysm) | − |
| 14 | 0.9 | M | Hispanic | 6 | 5.6 (anearysm) | − |
| 15 | 5.7 | F | Asian | 10 | 2.7 (dilated) | − |
| 16 | 1.6 | M | Caucasian | 5 | 1.3 | + |
| 17 | 2.9 | F | Hispanic | 5 | −0.1 | + |
| 18 | 6.4 | F | Asian | 6 | 1.0 | + |
| 19 | 1.9 | M | Asian/Caucasian | 8 | 2.3 | + |
| 20 | 0.8 | M | Hispanic | 4 | 8.1 (anearysm) | − |
| 21 | 5.6 | M | Asian/Caucasian | 4 | 1.5 | + |

Subjects 6, 16, 20 were also treated with infliximab.
[a]Illness day 1 = onset of fever.
[b]Z-max scores = maximum internal diameter for the left anterior descending or right coronary artery expressed as standard deviation units from the mean (Z-score) normalized for body surface area.

The internal diameter of the right and left anterior descending coronary arteries was measured and expressed as Z scores (standard deviation units from the mean normalized for body surface area; normal Z score <2.5). $Z_{worst}$ was defined as the highest Z score of either coronary artery measured during the first six weeks after fever onset. All KD subjects were treated with IVIG 2 gram (g)/kilogram (kg) and aspirin 80 to 100 mg/kd/day until afebrile, then 3 to 5 mg/kg day until the platelet count had returned to normal. All subjects were taking low dose aspirin at the time of the sub-acute phlebotomy. No subject in this series had IVIG resistance defined as persistent or recrudescent fever at least 36 h after completion of the initial IVIG infusion. Subjects 6, 16, and 20 received infliximab 5 mg/kg IV prior to WIG infusion as part of a clinical trial of intensification of initial WIG therapy (clinicaltrials.gov).

Heparinized blood samples (1-4 ml) were obtained prior to IVIG treatment at the time of diagnosis (acute) and two weeks after IVIG therapy (sub-acute). Pediatric patients with acute inflammatory conditions studied as controls (acute viral infections, bacterial infections, systemic drug allergy, juvenile idiopathic arthritis, and Henoch-Schoenlein purpura) had blood sampled only once and were aged 1.6-15.4 yrs. (Table 2):

TABLE 2

Acute pediatric febrile controls.

| Control subject # | Age, yrs | Sex | Race/Ethnicity | Illness day | Final diagnosis |
|---|---|---|---|---|---|
| 1 | 2.3 | F | Hispanic | 14 | Viral stomatitis |
| 2 | 2.1 | M | Hispanic | ~3-5 | Viral syndrome |
| 3 | 1.6 | F | Hispanic | 5 | Viral syndrome |
| 4 | 6.6 | F | Hispanic/Caucasian | 6 | Viral |
| 5 | 1.7 | F | American Indian | 4 | Viral/her angina |
| 6 | 5.8 | F | Caucasian | 6 | Adenovirus |
| 7 | 9.6 | M | Hispanic | 10 | Viral syndrome |
| 8 | 3.6 | F | Caucasian | 2 | Abscess |
| 9 | 2.2 | M | Asian | 5 | Viral |
| 10 | 15.4 | F | Caucasian | 2 | Bactrim drug reaction |
| 11 | 2.3 | F | Caucasian | 16 | Juvenile idiopathic arthritis (JIA) |
| 12 | 3.8 | F | Hispanic | 10 | Juvenile idiopathic athritis (JIA) |
| 13 | 4.6 | F | Hispanic | ~21 | Henoch-Schoenlein purpura (HSP) |

Fc-Specific Treg Detection and Characterization of Treg Phenotype

To enumerate Fc-specific Treg that activate after IVIG infusion, we developed a method to avoid non-specific expansion of Treg by tolerogenic DC or the expansion of effector T cells. PBMC were plated with scalar doses of purified Fc (1, 10 and 100 μg/ml; Life Meridian Science) at a concentration of $4 \times 10^5$ cells/well in 96 flat-bottomed plates (Falcon) for 4 days. Cell cultures did not receive any exogenous IL-2 prior to the assay: withholding IL-2 feeding in Fc-stimulated PBMC prevented the expansion of non-Fc-specific Treg and/or the expansion of effector T cell stimulated via Fcγ receptors. On day 4, culture supernatants were collected to measure IL-10, IFNγ and IL-2 by ELISA and to perform FACS analysis as described below.

CD4+CD25$^{high}$ T cell surface phenotype was determined by staining with specific monoclonal antibodies: anti-CD4 PerCP-Cy5.5, mouse IgG1κ, clone RPA-T4 and anti-CD25 PE, mouse IgG1κ, clone BC96 from eBioscience. BD FACSCanto was used for data acquisition; data were analyzed with FACSDiva (BD Biosciences) or FlowJo software (Tree Star, Inc). Intracellular FOXP3+ was measured with a kit from eBioscience (anti-human FOXP3 PE, mouse IgG1κ, clone 259/D/C7, anti-CD4 FITC, mouse IgG1κ, clone RPA-T4 and anti-CD25 APC, mouse IgG1κ, clone M-A251). Surface anti-IL-7r was measured using anti-CD127 PE, mouse IgG1κ, clone HIL-7R-M21; CD45RA by using anti-CD45RA-APC, mouse IgG2bκ, clone HI100 from BD Bioscience; IL-15r with anti-IL15r FITC, mouse IgG2b, clone JM74A; CCR7 with anti-CCR7 PE, rat IgG2aκ, clone 3D12; CCR6 with anti-CCR6 PE-Cy7, mouse IgG1κ, clone R6H1; CCR4 with anti-CCR4 PE, mouse IgG1κ, clone 1G1 from eBioscience. Levels of IL-10 and IL-4 produced by PBMC, Treg lines, and Treg clones were measured by ELISA with primary and secondary antibodies from BD Bioscience. mRNA was extracted from Treg clones using TRIZOL according to manufacturer's instructions. mRNA transcript abundance levels from cDNA derived from 25 ng of total RNA were measured using TAQMAN™ 5'-nuclease gene expression assay (Applied Biosystem, Foster City, Calif.) for IL-10, IL-4, TGFβ, IL-17 and CTLA-4. Results were normalized for the housekeeping gene TAF1b.

Activated and Memory CD4+ and CD8+ T Cell Characterization

Activated T cells were detected by staining with anti-human HLA-DR, PE, clone LN3, mouse IgG2b,κ, in combination with anti-human CD4, PerCP-Cy5.5, clone RPA-T4, Mouse IgG1,κ, and anti-human CD8, APC, clone RPA-T8, Mouse IgG1,κ from eBioscience. Memory T cells were detected with anti-human IL-15Rα, FITC, clone eBioJM7A4, Mouse IgG2b, from BD Bioscience.

Treg Cloning and Expansion

Fe-specific Treg lines were generated from PBMC stimulated with purified Fc (100 μg/ml). T cell lines were established by plating $4 \times 10^5$ cells/well in 96 flat-bottomed plates (Falcon). Each well was evaluated as an individual T cell line. On day 4 after stimulation in vitro, cell cultures were fed 100 U/ml of recombinant IL-2 (Peprotech), expanded for two days, and tested for specificity at day 6 from the first Fc stimulation in vitro (25). The specificity of the T cell lines was determined by measuring IL-10 in T cell culture supernatants collected at 48 hours following stimulation with one of the following: 1) irradiated autologous PBMC (negative control); 2) irradiated autologous PBMC pulsed with 20 μg/ml Fc; 3) irradiated allogeneic PBMC pulsed with 20 μg/ml Fc (MHC-restriction control). Treg lines that responded by producing IL-10 to autologous PBMC pulsed with Fc, but not to autologous PBMC alone or allogeneic PBMC pulsed with Fc, were cloned by limiting dilution (0.3-1 c/w) in the presence of $2 \times 10^4$ irradiated autologous EBV-transformed B cells per well pulsed with 20 μg/ml Fc as APC/antigen source. EBV-transformed B cell lines were obtained by infecting PBMC with supernatant from an EBV-producing marmoset-derived cell line B95-8 purchased from American Tissue Culture Collection (ATCC). T cell clones were stimulated weekly with irradiated autologous EBV lines pre-pulsed with Fc fragments and expanded with 100 U/ml of IL-2 every other day. Cloning to obtain IgG- and IgG+ autologous and allogenic B cell lines as APC source IgG+ autologous B cells to address the recognition of endogenous Fc by Treg (in addition to exogenous Fc) were obtained from EBV-transformed B cells derived from acute KD patients cloned early after transformation by limiting dilution. 13 cell clones were screened for surface IgG expression using anti-human CD19, APC-cy7, clone SJ25c1, mouse IgG1K, and anti-human IgG, PE, clone G18-145, Mouse IgG1K, that recognizes the framework of all IgG isotypes from BD Bioscience.

Statistical Analysis

Data analysis was conducted using PRISM™ version 5.0 software (GRAPHPAD™ Software, San Diego, Calif.). Statistical significance of the observed Fe-specific Treg expansion versus no antigen control was assessed by Wilcoxon matched-pairs signed rank test. Non-parametric Mann-Whitney test was used to compare the percent increase in Treg between groups of KD children. p-values less than 0.05 were considered significant.

Results

IL-10 Increases in Culture Supernatants of PBMC from Sub-Acute KD Patients Stimulated with Fc Fragments To address a possible role of the Fc in stimulating Treg in an antigen-specific, MHC-restricted manner, we developed an assay, starting with a small number of specific precursors, to measure IL-10 secretion and CD4+CD25$^{high}$ T cell expansion in response to scalar doses of purified Fc fragments (1, 10, 100 μg/ml) in bulk PBMC cultures.

After Ficoll-hypaque separation, PBMC from 15 sub-acute KD subjects who had received IVIG 2 weeks earlier (Table 1), were plated with scalar doses of purified Fc fragments for 4 days. Culture supernatants were collected to measure IL-10, IFNγ and IL-2. The measurement of IFNγ and IL-2 was included in these experiments to address a possible expansion of pro-inflammatory effector T cells by Fc stimulation.

IL-10 secretion by PBMC was documented in the culture supernatants of all 15 sub-acute KD subjects studied after IVIG therapy (subjects 1-14 and 20) (FIG. 1), regardless of their coronary artery status. The highest concentration of Fc tested (100n/ml) was the most effective (FIG. 1 of Example 2). The Fc fragments did not stimulate pro-inflammatory T cells with these experimental condition of Example 2).

Fc-Specific Treg Expand Only in KD Patients with Normal Coronary Arteries after IVIG but not in Patients with Arterial Abnormalities Despite the Presence of IL-10

To address the importance of the Treg specificity for the Fc in influencing clinical outcome, we measured the Treg response to purified Fc fragments in the same cultures in which IL-10 was detected (FIG. 1 of Example 2). Under these experimental conditions, only 4 days in culture in the absence of IL-2 in vitro, only Treg responding to the Fc via TcR recognition can survive and proliferate. 10 KD patients who did not develop arterial abnormalities after WIG therapy (subjects 1-10, FIG. 2) showed a brisk expansion of CD4+CD25$^{high}$ T cells after 4 days in response to scalar doses of Fc. Notably, Treg from the five patients who developed coronary artery abnormalities failed to respond to Fc stimulation in vitro (subjects 11-14 and 20, FIG. 2 of Example 2). Presumably, the source of the IL-10 in the subjects that developed arterial abnormalities was tolerogenic DC that we found abundant during the acute phase of KD and increase in numbers after WIG in the sub-acute phase regardless from the clinical outcome (4).

When we compared the magnitude of the Fe-specific Treg response in PBMC from the acute and sub-acute KD subjects, marked Fe-specific Treg expansion after IVIG treatment was observed only in patients with normal arteries but not in patients who developed arterial abnormalities (FIG. 3 of Example 2).

As shown in FIG. 4, FOXP3 analysis by intracellular staining confirmed the lack of Treg expansion in Fc-stimulated cultures from a sub-acute KD patient who developed coronary arterial dilation, subject 15, in contrast to a sub-acute KD patient with normal coronary arteries after IVIG therapy, subject 16, Table 1. These results further support the concept that the expansion of Fe-specific Treg plays an important role in resolution of the acute vasculitis in KD patients.

In five Treg responders, 10 μg/ml Fc was more immunogenic than 100 μg/ml (subjects 1,2,3,4, 9; FIG. 2 of Example 2), in sharp contrast to the higher dose required to stimulate IL-10 secretion in the same patients (FIG. 1 of Example 2). These results may reflect different MHC haplotypes that bind relevant Fc peptides recognized by Treg with different TcR affinities. The FACS images summarized in FIG. 2 are provided in supplemental FIG. 1A. As a control for antigenic specificity, we tested Treg expansion in response to increasing concentrations of F(ab)$_2$ fragments and documented no expansion (supplemental FIG. 1B).

Although we were unable to perform classic suppression assays due to the limited number of cells and the very young age of the patients that did not complete yet vaccination protocols, we observed that T cells with a pro-inflammatory phenotype decreased as the Fc-specific Treg increased. Specifically, activated CD4+ and CD8+DR+ T cells, but not IL-15 (receptor)r+ T cells, decreased in Fc-stimulated PBMC cultures in which the Treg expanded (subjects 18 and 19, FIG. 5).

Characterization of Fe-Specific Treg Clones Derived after IVIG from Sub-Acute KD Subjects with Normal Coronary Arteries Treg clones were generated from Fe-specific Treg lines derived from IVIG-treated, sub-acute KD subjects with normal coronary artery internal diameters and were screened for specificity. B-cell lines derived from 4 KD subjects were cloned by limiting dilution and screened for IgG expression. We measured IL-10 production by Treg clones in response to irradiated, autologous, IgG-negative B cell lines alone (control) or the same B cell lines incubated with Fc fragments. We expanded and further characterized the phenotype and lymphokine profile of Treg clones that made IL-10 in response to Fc-pulsed autologous IgG-negative B cells but not to the same B cells without Fc. Treg clones that secreted IL-10 in response to autologous B cells in the absence of Fc stimulation were considered to be auto-reactive for self-antigens other than Fc and were not studied further.

Fe-specific Treg clones produced high amounts of IL-10 and lower amounts of IL-4 but not TGFβ (FIG. 6A). The production of IL-10 and IL-4, but not TGFβ were confirmed by qRT-PCR analysis of RNA extracted from individual clones, which also demonstrated high transcript abundance for CTLA-4, a canonical marker for all Treg lineages, and no expression of IL-17 (FIG. 6A). T cells were further defined by surface and intracellular markers: CD4+CD25$^{high}$, IL-7r (CD127)$^{low}$, CD45RA$^{low}$ FOXP3$^{high}$ (FIG. 6B). The memory marker IL-15r and CCR6, the homing receptor for vessels, were not expressed by Fc-specific Treg clones, which did express high levels of CCR7, an important homing receptor for lymphoid organs (FIG. 6B). The low expression level of CD127 coupled with absent expression of CCR4 excluded the possibility of contamination by T helper (h) 2 cells in this T cell clonal effort (26).

Figure 7A:
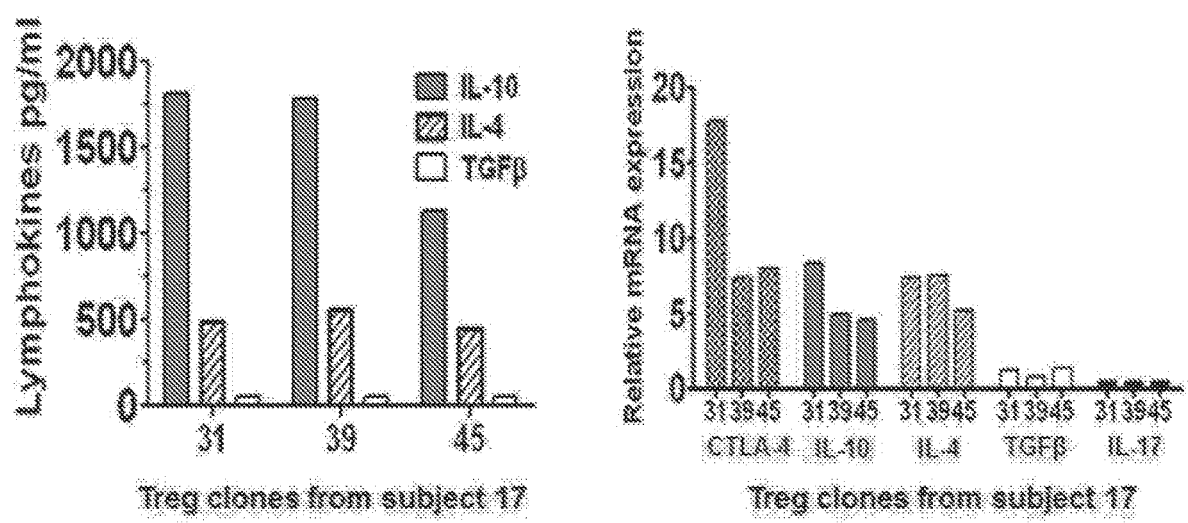
FIG. 7A and FIG. 7B graphically illustrate data showing characterization of Fc-specific Treg clones: 3 representative Treg clones were generated from a KD subject 17 two weeks following IVIG treatment.
Figure 7B:
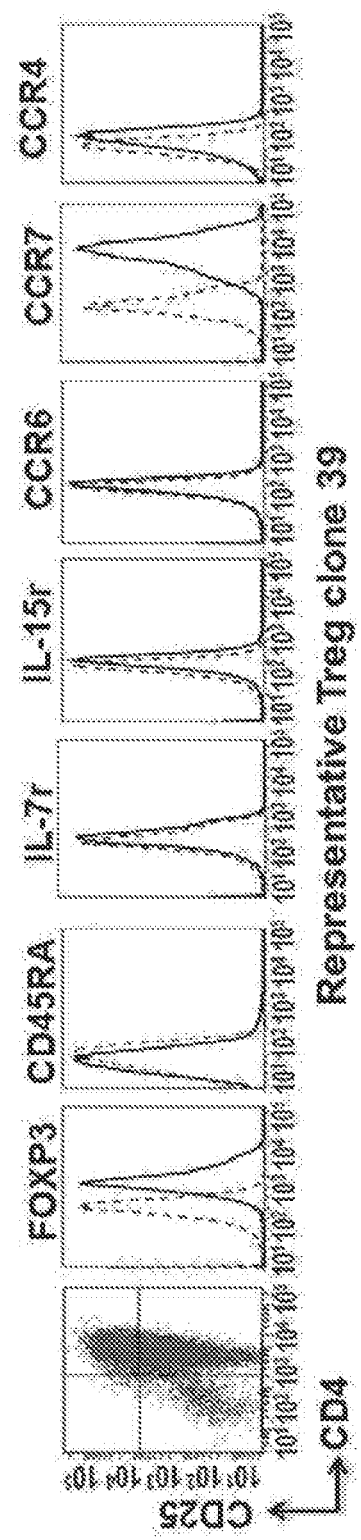

Fe-Specific Treg Clones Respond to Autologous IgG+ B Cells in the Absence of Exogenous Fc We next addressed whether Fc-specific Treg clones respond to both: 1) exogenous Fc fragments presented by autologous IgG negative B cells and 2) endogenous Fc derived from membrane IgG on the cell surface of autologous IgG+ B cells. When autologous, live, irradiated IgG+ B cells were used as antigen presenting cells, Fe-specific Treg clones responded by secreting IL-10 and IL-4 in the absence of exogenous Fc (FIG. 7A). To determine if conventional antigen processing of IgG molecules by B cells is required to stimulate Fc-specific Treg, we tested in parallel the antigen presenting capacity of live versus paraformaldehyde-fixed autologous IgG+ B cell lines (FIG. 7A). MHC restriction was required for Fc presentation and Treg response because only autologous, but not allogeneic, IgG+ B-cells induced IL-10 and IL-4 secretion (FIG. 7B). The requirement for TcR signaling rather than Fcγ receptor stimulation on T cells was further confirmed by the dose-dependent IL-10 production by Treg clones in response to an anti-CD3 agonistic antibody (supplemental FIG. 2).

Figure 8A:
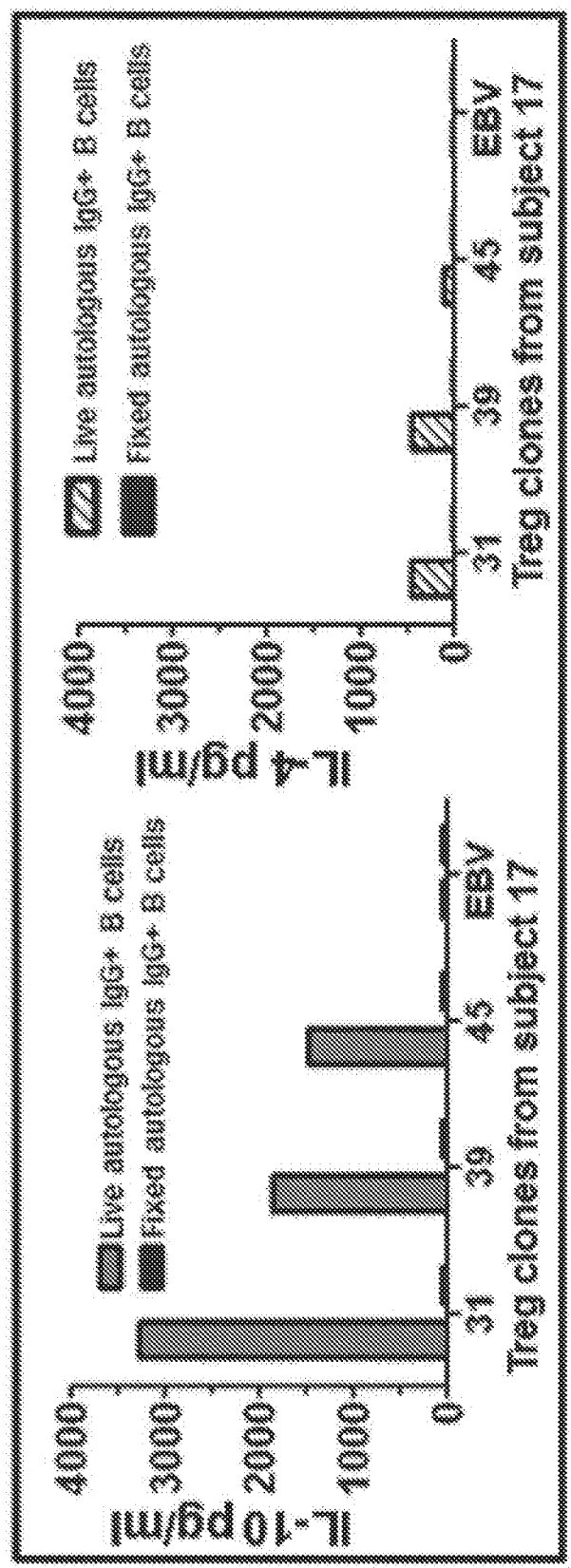
FIG. 8A and FIG. 8B illustrates data showing that Fc-specific Treg clones recognize endogenous processed IgG presented by autologous B cells in an MHC-restricted, TcR-mediated manner.
Figure 8B:
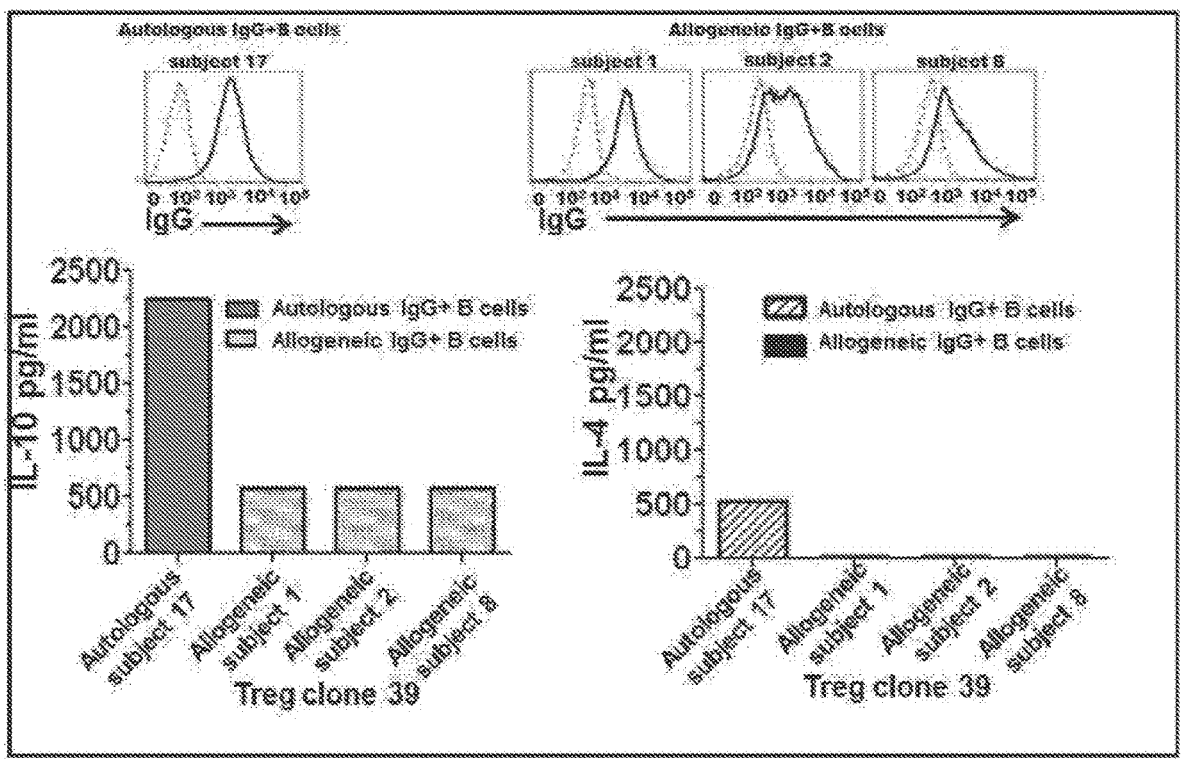

Treg Expand when Stimulated In Vitro by Fc in Children with Acute Infections and Drug Reactions, but not in Untreated Children with Autoimmune Diseases To address if this Fc-specific Treg population physiologically expand during other acute pediatric inflammatory conditions, we tested the magnitude of Treg expansion in Fc-stimulated PBMC in a variety of controls that included children with self-limited viral infections (n=7), bacterial infections (n=2), systemic drug reaction (n=1), and three newly diagnosed, untreated autoimmune diseases (juvenile idiopathic arthritis, n=2, Henoch Schoenlein purpura, n=1). In 10 of 13 pediatric subjects with acute viral or bacterial infection or systemic drug reactions, but not autoimmunity, Fc-induced Treg responses were detected (median Treg %=0.28%, 95% CI 0.20-0.37 at 10 μg/ml of purified Fc) (FIG. 8).

DISCUSSION

There is a growing list of the immune modulatory functions of IVIG that includes expansion of IL-10-secreting DC stimulated by Fc fragments and the non-specific, IL-10 mediated expansion of Treg observed in humans and mice (3, 4, 6, 27, 28). To this list, we can now add a newly discovered action of IVIG: expansion of a population of Treg that recognize the Fc region of IgG presented in a conventional MHC-restricted, TcR-mediated fashion by mature B cells. Following IVIG therapy, this Fc-specific Treg population expands in KD patients with normal coronary arteries but fails to expand in patients who develop dilated or aneurysmal coronary arteries despite IVIG treatment. Although IL-10 secretion in response to Fc stimulation of PBMC in sub-acute KD patients after IVIG is important, it is not sufficient to resolve the vasculitis, since in the absence of Fe-specific Treg expansion following in vivo boost by IVIG therapy it did not prevent coronary arterial abnormalities. Our results demonstrate that the specificity of the Treg, as for any other adaptive immune response, is critical for the suppression in vivo of pathogenic T cells. This Treg population expands during acute inflammation in patients suffering from a variety of different infections, but not in children with new-onset, untreated autoimmune disease.

The recognition of endogenous IgG presented by mature B cells appears to maintain Fe-specific Treg that have been activated by IVIG in vivo. These Treg are fully functional in very young infants and children. B cell antigen presentation of endogenous Fc by mature B cells and circulating IgG presented by conventional APC (i.e. DC) keep stimulating Fc-specific Treg: the antigen (Fc) is always present under physiological conditions and IgG-expressing mature B cells reside in normal lymph nodes, tonsils, Peyer patches, bone marrow and other secondary lymphoid organs.

The phenotype of Fc-specific Treg clones that expand after WIG in KD patients suggests that they down-regulate acute vasculitis by suppressing pro-inflammatory T cells not in the inflamed coronary arteries but in the lymph nodes and other secondary lymphoid organs as evidenced by the expression of CCR7 (19). In fact, CCR6, which is a critical chemokine receptor for T cell homing to the vessels (29), was not expressed on any of the Treg clones studied. Lack of CCR6 expression on Fc-specific Treg clones further supports the idea that this T cell subset is different from auto-reactive, peripherally induced Treg previously reported in humans (19) or pathogen-induced human Th17 T cells that produce IL-10 regulated by IL-1 (30). The Treg population described herein is also different from the Treg that respond to optimized, pan-DR-binding exogenous Fc peptides (Tregitopes), which have been previously described in adult healthy donors (24). Those T cells were CCR7 negative and did not express high levels of CTLA-4, which we detected in all the Fc-specific Treg clones studied. Moreover, the Treg described here secrete low amounts of IL-4 that may be functionally important to sustain B cell survival and expansion. The results suggest in fact a new model of T-B cooperation.

An important role for Fc-specific Treg and mature B cell-Treg interactions in immune-regulation is further supported by the blunted expansion of this Treg specificity in children with newly diagnosed, untreated autoimmune diseases. Collectively, it appears as if a defect in the Treg-mediated suppression of the pro-inflammatory T cell response in KD patients with coronary artery abnormalities and in children with autoimmune disorders is associated with disease progression.

In summary, we demonstrate the role of exogenous IgG and mature B cells in the control of an acute pediatric vasculitis of the coronary arteries via the expansion of Treg that recognize the Fc portion of IgG. Our results suggest a novel mechanism for the anti-inflammatory action and clinical benefit provided by IVIG therapy in patients with KD and, potentially, other vasculitides (34). Measuring the expansion of Fc-specific Treg may be helpful for clinical risk assessment in the case of KD and potentially for monitoring other immune-mediated pathological conditions and response to IVIG therapy.

Figure Legends—Example 2

FIG. 1 of Example 2 (or FIG. 2). PBMC derived from sub-acute KD subjects secrete IL-10, but not IFN-gamma or IL-2 in response to scalar doses of Fc. PBMC from 15 KD subjects, 10 with normal arteries after IVIG therapy (subjects 1-10) and 5 with dilated arteries or aneurysm after IVIG therapy
(subjects 11-14 and 20) were cultured with scalar doses of purified Fc fragments (Meridian Life Science, purity >97%) for 4 days in the absence of exogenous lymphokines. Supernatants were harvested and tested for IL-10, IFN-gamma and IL-2 secretion by ELISA.

FIG. 2 of Example 2 (or FIG. 3). Enumeration of Fc-induced Treg in sub-acute KD patients with normal arteries after IVIG. FIG. 2A: CD4+CD25$^{high}$ Treg expansion to scalar doses of Fc was analyzed by flow cytometry in PBMC cultures derived from 15 sub-acute KD subjects, with normal arteries (subjects 1-10) and 5 with dilated arteries or aneurysm (subjects 11-14 and 20) previously studied for lymphokine production. PBMC were cultured for 4 days with 0 (no antigen), 1, 10, or 100<g/ml of purified Fc fragments (Meridian Life Science, purity ≥97%). FIG. 2B: Summary of the Treg response in 15 sub-acute KD subjects described in panel A. The median % increase in Treg expansion for the subjects with normal coronary arteries was calculated with an Fc dose of 10 µg/ml.

FIG. 3 of Example 2 (or FIG. 4). Differential expansion of Fc-specific Treg from the acute to the sub-acute phase of KD depending upon clinical outcome. We studied the fold-increase of the Fc-specific Treg repertoire from the acute to sub-acute phase in 6 KD subjects: three subjects with normal coronary arteries after IVIG therapy (subjects 2, 7, 10), three subjects with dilated arteries or aneurysm despite IVIG therapy (subjects 12, 13, 14).

FIG. 4 of Example 2 (or FIG. 5). FOXP3+ T cells expansion in response to Fc. Intracellular staining for FOXP3$^{high}$ expression in CD4+ T cells was assessed in Fc-stimulated PBMC cultures from two subacute patients after WIG therapy. Subject 15 had dilated coronary arteries by echocardiogram, and there was no expansion of the Fc-specific Treg population. Subject 16 had normal coronary arteries and showed expansion of the Treg population in response to 100<g/ml Fc.

FIG. 5 of Example 2 (or FIG. 6). Activated CD4+ and CD8+CD25$^{low}$ DR$^{high}$ but not memory IL15r+ T cells decrease in PBMC cultured with Fc when Treg expand. PBMC from two sub-acute KD subjects with normal arteries after IVIG (Subjects 18 and 19) were cultured with 100<g/ml purified Fc fragments or media alone as control to address the fate of activated T cells and memory T cells in Fc-stimulated cultures in which Treg expand. Treg were defined as CD4+CD25$^{high}$; activated CD4+ and CD8+ T cells as CD25$^{low}$ and DR$^{high}$; and memory T cells as IL-15r+. After 4 days in culture with Fc, Treg expanded but activated CD4+ and CD8+ T cell numbers decreased. IL-15r+ memory T cells remained unchanged.

FIG. 6 of Example 2 (or FIG. 7). Characterization of Fc-specific Treg clones. Three representative Treg clones generated from KD subject 17 two weeks following IVIG treatment. Panel A: Left: Production of IL-10, IL-4 and TGFβ measured by ELISA 48 hours after stimulation with autologous, irradiated B cells pulsed with 20 µg/ml Fc fragments; Right: qRT-PCR analysis of cell lysates from the same three Treg clones. Panel B: Phenotype of a representative Treg clone characterized as CD4+CD25$^{high}$, intracellular FOXP3$^{high}$, CD45RA$^{low}$, IL15r−, CCR6−, CCR7$^{high}$ and CCR4−.

FIG. 7 of Example 2 (or FIG. 8). Fc-specific Treg clones recognize endogenous processed IgG presented by autologous B cells in an MHC-restricted, TcR-mediated manner. Panel A: Live, but not paraformaldehyde-fixed, autologous EBV-transformed IgG+ B cells stimulate Treg clones to secrete IL-10 and IL-4 in the absence of exogenous Fc demonstrating that a) IgG needs to be conventionally processed for Treg recognition; b) the Treg response is not directed to self MHC molecules. Panel B: Only autologous, but not allogeneic IgG+ B cells activate a Fc-specific Treg clone, demonstrating that the Fc-specific Treg response is MHC-restricted.

Figure 9:
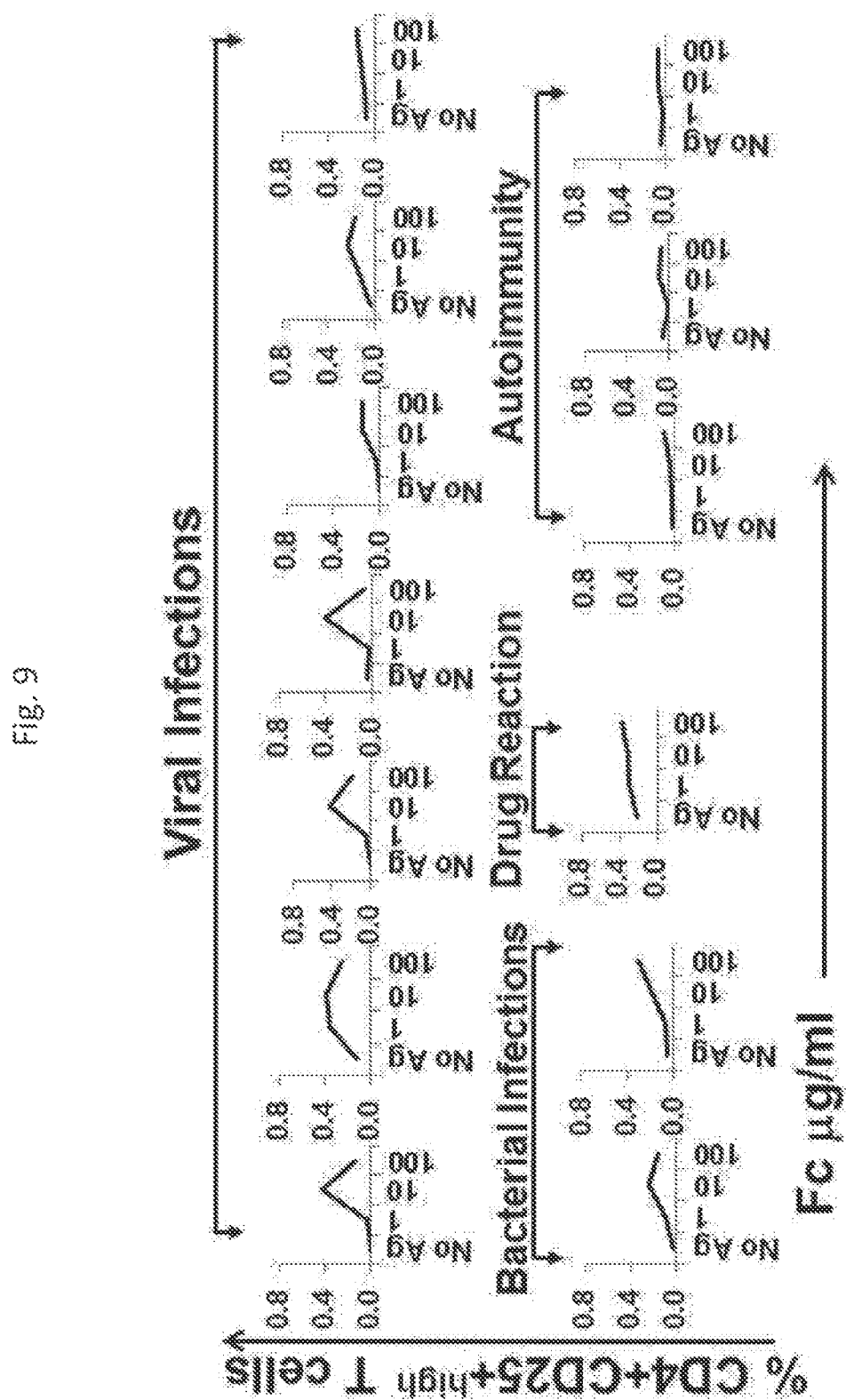
FIG. 9 graphically illustrates data showing that Treg (the characterized as CD4+CD25$^{high}$ T cells) expand in response to Fc in acute pediatric inflammatory conditions but not in subjects with acute autoimmune conditions, where Fc-induced Treg expansion in cultured PBMC was detected after Fc stimulation in 7 subjects with acute viral infections, 2 subjects with bacterial infections and 1 subject with a systemic drug reaction, as described in detail in Example 2, below.

FIG. 8 of Example 2 (or FIG. 9). Treg expand in response to Fc in acute pediatric inflammatory conditions but not in subjects with acute autoimmune conditions. Fc-induced Treg expansion in cultured PBMC was detected after Fc stimulation in 7 subjects with acute viral infections, 2 subjects with bacterial infections and 1 subject with a systemic drug reaction. Three patients with new-onset, untreated autoimmune conditions failed to show Treg expansion in response to Fc.

Figure 10B:
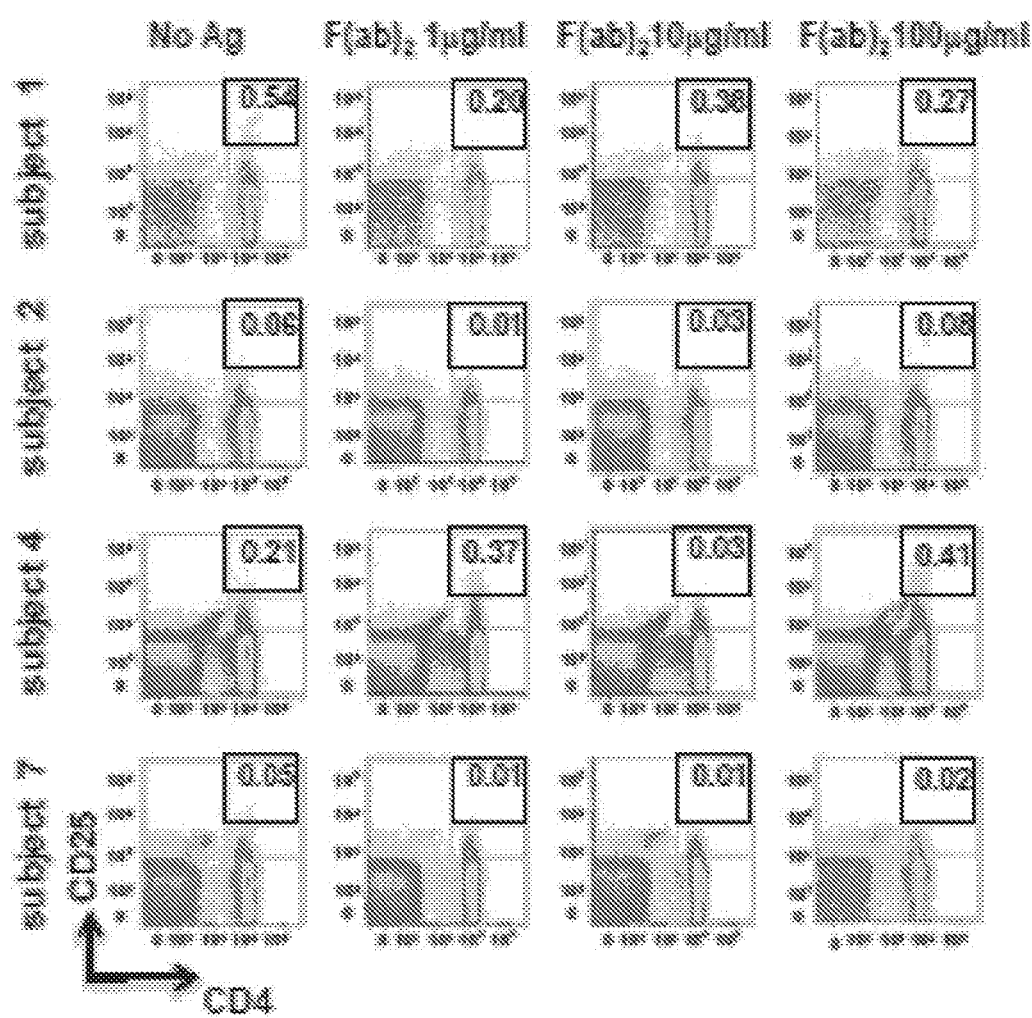

Supplemental FIG. 1 of Example 2 (or FIG. 10). Treg response to purified Fc and F(ab)2 fragments in sub-acute KD subjects. Panel A: CD4+CD25$^{high}$ Treg expansion in PBMC cultures from sub-acute KD subjects (subjects 1-10) with normal arteries after IVIG therapy in response to scalar doses of Fc. Panel B: Lack of CD4+CD25$^{high}$ Treg expansion in response to F(ab)2 fragments in 4 patients within the same cohort (subjects 1, 2, 4, 7).

Figure 11:
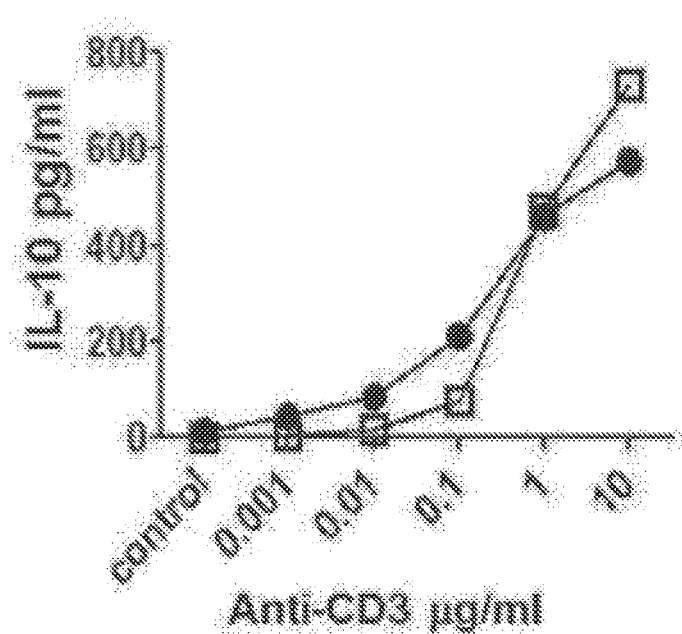
FIG. 11 graphically illustrates the Fc-specific clonal Treg response is TcR mediated: two representative Fc-specific Treg clones secrete IL-10 when stimulated 24 hours in vitro with an anti-CD3 agonistic antibody, as described in detail in Example 2, below.

Supplemental FIG. 2 of Example 2 (or FIG. 11). The Fc-specific clonal Treg response is TcR mediated. Two representative Fc-specific Treg clones secrete IL-10 when stimulated 24 hours in vitro with an anti-CD3 agonistic

Example 3: Peptides Effective for Expanding Regulatory T Cells (Treg) Populations—Fine Specificities of Natural Regulatory T Cells after IVIG Therapy in Patients with Kawasaki Disease—Epitope Mapping of Human Fc-Specific Natural Treg This example presents data demonstrating that compositions as provided herein effectively expand regulatory T cells (Treg) populations for, e.g., ameliorating vascular inflammation, and Kawasaki disease or a pediatric acute vasculitis of the coronary arteries, including vascular coronary abnormalities and the same or similar types of acute or chronic vascular inflammatory abnormalities.

Here we characterize the fine specificity of nTreg in sub-acute KD subjects (2-8 weeks post-IVIG) and convalescent KD subjects (1-10 years post-IVIG) by testing the immunogenicity of 64 peptides, 15 amino acids in length with a 10 amino acid-overlap spanning the entire Fc protein. Overall, 12 Fc peptides (6 pools of 2 consecutive peptides) were recognized by nTreg in the cohorts studied, including two patients with CAA.

To test whether IVIG stimulates the expansion of the same nTreg populations that maintain vascular homeostasis under physiological conditions in healthy subjects, we compared these results with results obtained in healthy adult controls. Similar nTreg fine specificities were observed in KD patients after IVIG and in healthy donors. Overall, these results suggest that T cell fitness rather than T cell clonal deletion or anergy is responsible for the lack of Fc-specific nTreg expansion in KD patients who develop CAA.

Furthermore, we found that adolescents and adults who had KD during childhood without developing CAA did not respond to the Fc protein in vitro, suggesting that the nTreg response induced by IVIG in KD patients is short-lived. Our results support the concept that synthetic, Fc-derived peptide epitopes as provided herein are a viable therapeutic approach to expand Fc-specific nTreg and more effectively prevent CAA in KD patients.

In this study, we describe the fine specificity of Fc-specific nTreg by testing their response to overlapping peptides covering the entire Fc molecule. We also tested the nTreg response to the whole Fc protein of adolescents and adults with a history of KD in childhood to assess the durability of the nTreg response years after IVIG and we compared it with sex-matched healthy donors. These studies showed that Fc-specific nTreg fine specificity is similar in KD and healthy donors, but these responses are short lived in KD patients. Since this defect can be overcome by administration of large doses of IVIG in most KD patients, our results demonstrate that the administration of Fc-derived peptide epitopes as provided herein are a viable therapeutic approach to expand Fc-specific nTreg and prevent CAA.

Material and Methods

Study population: Sub-acute and convalescent pediatric KD patients were enrolled at Rady Children's Hospital San Diego following parental informed consent and patient assent as appropriate. All KD subjects were treated with IVIG 2 g/kg and aspirin 80-100 mg/kg/day until afebrile, then 3-5 mg/kg/day until the platelet count had returned to normal. All sub-acute subjects were taking low dose aspirin at the time of phlebotomy. KD subjects (10 sub-acute subjects: 5 males, 5 females aged 2.0-15.5 years at time of study) and six convalescent subjects: 5 males, 1 female, aged 2.4-15.7 years at time of study) were evaluated by echocardiography during the acute admission and at 2 and 6 weeks and 1 year following diagnosis. The internal diameter of the right and left anterior descending coronary arteries was measured and expressed as a Z score (standard deviation units from the mean normalized for body surface area; normal Z score <2.5). $Z_{worst}$ was defined as the highest Z score of either coronary artery measured during the first 6 weeks after fever onset. Two of the subacute patients developed CAA despite IVIG treatment, as illustrated in Table 1, or FIG. 12, which illustrates the demographic and clinical status of pediatric KD study subjects. Heparinized blood samples (1-4 ml) were obtained 10-54 days post-IVIG (sub-acute cohort, subjects #1-10) and 1-2 years post-IVIG for five subjects (#11-14, 16) and 10 years post-IVIG for one subject (#15) (convalescent cohort).

As a comparison group for the Fc epitope mapping, six normal healthy donors (4 males, 2 females aged 25-59 years) were recruited at the Scripps Research Institute, La Jolla Calif. following written informed consent (IRB #101213X).

To test the durability of the Fc-specific nTreg response, 8 subjects who had KD during childhood without developing CAA (4 males and 4 females aged 12-42 years, Table 2, below) were tested for Fc-specific nTreg responses to the whole Fc protein in vitro and compared to 8 additional sex-matched healthy donors.

TABLE 2

Demographic characteristics of adolescent and adult subjects with a history of KD in childhood.

| KD subject # | Sex | Age at KD onset (years) | Age at testing (years) | Race/ethnicity | IVIG treatment |
|---|---|---|---|---|---|
| A1 | M | 7 | 19 | White | Yes |
| A2 | M | 3 | 19 | Hispanic | Yes |
| A3 | F | 1 | 12 | African-American | Yes |
| A4 | M | 4 | 16 | White | Yes |
| A5 | F | 5 | 28 | White | Yes |
| A6 | M | 2 | 19 | Mixed | No |
| A7 | F | 4 | 21 | Asian | Unknown |
| A8 | F | 1 | 42 | Asian | No |

Peptides: Peptides were synthesized by Fmoc chemistry using a multiplex peptide synthesizer (Symphony X, Protein Technologies Inc., Tucson, Ariz.). Peptides were cleaved automatically on the synthesizer using trifluoroacetic acid. Peptides were ≥97% pure as assessed by C18 reverse phase HPLC, and the identity of the peptides was verified by mass spectrometry. A total of 64 peptides, each 15 amino acids in length with a 10 amino acid-overlap for each peptide, spanning the whole Fc molecule were used to define the fine specificity of Fc-specific nTreg. The amino acid sequences of the 15-mer overlapping peptides are shown in Table 3, see FIG. 13; and also summarized (** indicates an exemplary peptide sequence of the invention):

```
Fc position 1-15
                                   (SEQ ID NO: 18)
STKGPSVFPLAPSSK Fc position 6-20
                                   (SEQ ID NO: 19)
SVFPLAPSSKSTSGG
```

-continued

Fc position 11-25
(SEQ ID NO: 20)
APSSKSTSGGTAALG

Fc position 16-30
(SEQ ID NO: 21)
STSGGTAALGCLVKD

** Fc position 21-35
(SEQ ID NO: 1)
TAALGCLVKDYFPEP

** Fc position 26-40
(SEQ ID NO: 2)
CLVKDYFPEPVTVSW

Fc position 31-45
(SEQ ID NO: 22)
YFPEPVTVSWNSGAL

Fc position 36-50
(SEQ ID NO: 23)
VTVSWNSGALTSGVH

Fc position 41-55
(SEQ ID NO: 24)
NSGALTSGVHTFPAV

Fc position 46-60
(SEQ ID NO: 25)
TSGVHTFPAVLQSSG

** Fc position 51-65
(SEQ ID NO: 9)
TFPAVLQSSGLYSLS

** Fc position 56-70
(SEQ ID NO: 10)
LQSSGLYSLSSVVTV

** Fc position 61-75
(SEQ ID NO: 11)
LYSLSSVVTVPSSSL

** Fc position 66-80
(SEQ ID NO: 12)
SVVTVPSSSLGTQTY

Fc position 71-85
(SEQ ID NO: 26)
PSSSLGTQTYICNVN

Fc position 76-90
(SEQ ID NO: 27)
GTQTYICNVNHKPSN

Fc position 81-95
(SEQ ID NO: 28)
ICNVNHKPSNTKVDK

Fc position 86-100
(SEQ ID NO: 29)
HKPSNTKVDKKVEPK

Fc position 91-105
(SEQ ID NO: 30)
TKVDKKVEPKSCDKT

Fc position 96-110
(SEQ ID NO: 31)
KVEPKSCDKTHTCPP

Fc position 101-115
(SEQ ID NO: 32)
SCDKTHTCPPCPAPE

Fc position 106-120
(SEQ ID NO: 33)
HTCPPCPAPELLGGP

Fc position 111-125
(SEQ ID NO: 34)
CPAPELLGGPSVFLF

Fc position 116-130
(SEQ ID NO: 35)
LLGGPSVFLFPPKPK

** Fc position 126-140
(SEQ ID NO: 4)
PPKPKDTLMISRTPE

Fc position 131-145
(SEQ ID NO: 36)
DTLMISRTPEVTCVV

Fc position 136-150
(SEQ ID NO: 37)
SRTPEVTCVVVDVSH

Fc position 141-155
(SEQ ID NO: 38)
VTCVVVDVSHEDPEV

Fc position 146-160
(SEQ ID NO: 39)
VDVSHEDPEVKFNWY

Fc position 151-165
(SEQ ID NO: 40)
EDPEVKFNWYVDGVE

Fc position 156-170
(SEQ ID NO: 41)
KFNWYVDGVEVHNAK

Fc position 161-175
(SEQ ID NO: 42)
VDGVEVHNAKTKPRE

Fc position 166-180
(SEQ ID NO: 43)
VHNAKTKPREEQYNS

Fc position 171-185
(SEQ ID NO: 44)
TKPREEQYNSTYRVV

** Fc position 176-190
(SEQ ID NO: 13)
EQYNSTYRVVSVLTV

** Fc position 181-195
(SEQ ID NO: 14)
TYRVVSVLTVLHQDW

Fc position 186-200
(SEQ ID NO: 45)
SVLTVLHQDWLNGKE

Fc position 191-205
(SEQ ID NO: 46)
LHQDWLNGKEYKCKV

Fc position 196-210
(SEQ ID NO: 47)
LNGKEYKCKVSNKAL

Fc position 206-220
(SEQ ID NO: 48)
SNKALPAPIEKTISK

Fc position 211-225
(SEQ ID NO: 49)
PAPIEKTISKAKGQP

Fc position 216-230
(SEQ ID NO: 50)
KTISKAKGQPREPQV

-continued

Fc position 221-235 (SEQ ID NO: 51)
AKGQPREPQVYTLPP

Fc position 226-240 (SEQ ID NO: 52)
REPQVYTLPPSRDEL

Fc position 231-245 (SEQ ID NO: 53)
YTLPPSRDELTKNQV

Fc position 236-250 (SEQ ID NO: 54)
SRDELTKNQVSLTCL

Fc position 241-255 (SEQ ID NO: 55)
TKNQVSLTCLVKGFY

Fc position 246-260 (SEQ ID NO: 56)
SLTCLVKGFYPSDIA

Fc position 251-265 (SEQ ID NO: 57)
VKGFYPSDIAVEWES

Fc position 256-270 (SEQ ID NO: 58)
PSDIAVEWESNGQPE

Fc position 261-275 (SEQ ID NO: 59)
VEWESNGQPENNYKT

** Fc position 266-280 (SEQ ID NO: 7)
NGQPENNYKTTPPVL

** Fc position 271-285 (SEQ ID NO: 8)
NNYKTTPPVLDSDGS

** Fc position 276-290 (SEQ ID NO: 15)
TPPVLDSDGSFFLYS

Fc position 281-295 (SEQ ID NO: 60)
DSDGSFFLYSKLTVD

Fc position 286-300 (SEQ ID NO: 61)
FFLYSKLTVDKSRWQ

** Fc position 291-305 (SEQ ID NO: 5)
KLTVDKSRWQQGNVF

** Fc position 296-310 (SEQ ID NO: 6)
KSRWQQGNVFSCSVM

** Fc position 301-315 (SEQ ID NO: 16)
QGNVFSCSVMHEALH

** Fc position 306-320 (SEQ ID NO: 17)
SCSVMHEALHNHYTQ

Fc position 311-325 (SEQ ID NO: 62)
HEALHNHYTQKSLSL

Fc position 316-329 (SEQ ID NO: 63)
NHYTQKSLSLSPGK

Characterization of peptide-specific nTreg responses: Heparinized blood samples were collected in sodium heparin green top tubes for isolation of peripheral blood mononuclear cells (PBMC) from healthy adult donors and KD subjects. To enumerate Fc-specific nTreg that expand after WIG infusion, we previously developed a method to avoid non-specific expansion of peripherally-induced (p)Treg by tolerogenic dendritic cells (DC) or the expansion of effector T cells (3). PBMC were plated with scalar doses of purified Fc (1, 10 and 100 µg/ml; Life Meridian Science) or pools containing two peptides each (20 µg/ml/peptide, Table 3, see FIG. 13) at a concentration of $2 \times 10^5$ cells/well in 96-well flat-bottomed plates (Falcon) for 4 days. Cell cultures did not receive any exogenous IL-2 prior to the assays to prevent the expansion of non-Fe-specific nTreg and/or the expansion of effector T cells stimulated via Fc-gamma receptors.

On culture day 4, supernatants were collected to measure IL-10 secretion by ELISA with primary and secondary antibodies from BD Bioscience on all subjects as previously described (3). A positive nTreg response was defined as IL-10 secretion that exceeded 20 µg/ml. For four KD subjects and all eight of the normal adult donors, cells from these cultures were harvested on day 4 for FACS analysis. CD4+CD25$^{high}$ T cell surface phenotype was determined by staining with specific monoclonal antibodies: anti-CD4 PerCP-Cy5.5, mouse IgG1 κ, clone RPA-T4 and anti-CD25 PE, mouse IgG1κ, clone BC96 from eBioscience. BD FACSCanto was used for data acquisition; data were analyzed with FACSDiva (BD Biosciences) or FlowJo software (Tree Star, Inc).

HLA Class II Binding Prediction for Fc-Derived Peptides

As a preliminary analysis to determine the potential HLA class II binding capacity of Fe-derived peptides, we scanned the sequences using the suite of class II algorithms available through the NIH-funded and La Jolla Institute for Allergy and Immunology-administered website, Immune Epitope Database (IEDB). For HLA class II binding predictions, the entire IgG Fc sequence was parsed into the set of 15-mer peptides, overlapping by 10 residues (Table 3, FIG. 13, and see summary, above) that we functionally tested for immunogenicity in KD subjects after IVIG and healthy donors. The capacity of each peptide to bind a panel of 27 common HLA class II DR, DQ and DP molecules was predicted using the IEDB consensus algorithm, see e.g., Vita et al., The immune epitope database (IEDB) 3.0. Nucleic Acids Res. 2014 Oct. 9. (8). A peptide was considered a binder to any class II if its corresponding consensus score was $\leq 20^{th}$ percentile (8). Binding to any specific allele was defined as a corresponding consensus prediction score ≤20th percentile. The number of alleles bound was tabulated for each peptide. A promiscuous binding peptide was operationally defined as a peptide binding or predicted to bind to 50% or more of the 26 alleles. The total number of class II molecules predicted to be bound was tabulated and plotted.

Results

Fine Specificity of Fc-Specific nTreg Determined with 15-Mer Overlapping Peptides in KD Subjects after IVIG Discrete regions within the Fc sequence were immunogenic for nTreg in subacute KD subjects after IVIG stimulating IL-10 secretion in 9 of the 10 subjects and including CD4+CD25$^{high}$ T cell expansion in all four subjects assessed (subject 1 recognized a unique set of epitopes, data not shown). Peptides were ranked based on IL-10 secretion and peptides 121-135 and 126-140 (pool 13) were the most immunogenic being recognized by nTreg in 8 of 16 (50%) KD subjects (FIG. 1 of Example 3, or FIG. 14). Other sequences also resulted in expansion of the nTreg populations: 7 of 16 (44%) KD subjects responded to amino acid residues 276-290 and 281-295 (pool 28); three different peptide pools corresponding amino acid residues 51-65 and 56-70 (pool 6), amino acid residues 181-195 and 186-200 (pool 19), amino acid residues 301-315 and 306-320 (pool 31) were recognized in 6 of 16 (37%) KD subjects. Finally, 5 out of 16 (31%) KD subjects recognized amino acid residues 61-75 and 66-80 (pool 7). Of interest, the two KD subjects with CAA (subjects #5 and 6) showed a measurable nTreg response to pool 28 and pool 6, respectively (FIG. 1 of Example 3, or FIG. 14), suggesting that the fine specificity of this KD subgroup was similar to the remainder of the KD subjects tested.

The strength of the response varied among subjects possibly reflecting their HLA type and the precursor frequency of peptide-specific nTreg after IVIG. We observed a rapid expansion of the CD4+CD25$^{high}$ T cell population in some KD patients in response to peptide epitopes after IVIG, suggesting a very high precursor frequency (FIG. 2 of Example 3, or FIG. 15).

Fine Specificity of Fc-Specific nTreg Determined with 15-Mer Overlapping Peptides in Healthy Adult Donors To compare Fc-specific nTreg responses that arise in KD patients after IVIG to the specificities of nTreg in healthy donors, we performed Fc epitope mapping in six healthy adult subjects. As observed in KD patients after IVIG, discrete regions within the Fc sequence were found to be immunogenic for nTreg and stimulated the secretion of IL-10 and CD4+CD25$^{high}$ T cell expansion. The epitope ranking indicated that the immunodominant responses were similar in healthy controls compared to KD patients after IVIG. Peptides 121-135 and 126-140 (pool 13) were the most immunogenic and were recognized by nTreg in 6 of 7 (86%) donors (FIG. 3 of Example 3, or FIG. 16). Several other pools defined as immunogenic in KD subjects also stimulated nTreg in healthy donors: 5 of 7 (71%) healthy donors responded to amino acid residues 276-290 and 281-295 (pool 28), 301-315 and 306-320 (pool 31); 4 of 7 (57%) donors responded to amino acid residues 181-195 and 186-200 (pool 19); 3 of 7 (43%) donors responded to amino acid residues 51-65 and 56-70 (pool 6), 61-75 and 66-80 (pool 7) ((FIG. 3 of Example 3, or FIG. 16). Responses to amino acid residues 21-35 and 26-40 (pool 3) and 31-45 and 36-50 (pool 4) were unique, as these pools were not immunogenic for the KD subjects (FIG. 4 of Example 3, or FIG. 17).

nTreg from Healthy Adults Who had KD in Childhood without Developing CAA Fail to Respond In Vitro to Whole Fc Protein We previously showed that acute KD subjects lack Fc-specific nTreg prior to IVIG (3). IVIG therapy activates this nTreg repertoire in KD patients who do not develop CAA but it was unknown if the Fe-specific nTreg response to the whole Fc protein was long lasting or if it waned over time. Therefore, we tested CD4+CD25$^{high}$ nTreg expansion in response to Fc fragments in eight healthy adults who had KD during childhood without developing arterial complications (Table 2, see above) and compared their response with eight healthy adult donors. nTreg derived from adolescents and adults years after IVIG treatment for KD did not expand in response to Fc fragments in sharp contrast to healthy adult controls (FIG. 5 of Example 3, or FIG. 18).

HLA/Fc-Derived Peptide Binding Prediction Analysis

It was previously shown that peptides predicted to bind 50% or more of the HLA alleles assessed at the 20% or better consensus prediction level correspond to the most dominant epitopes, and encompass a large fraction of the T cell responses to EPO (9), allergens such as timothy grass and mycobacteria tuberculosis antigens (10-12). Since peptide: HLA binding is required, but not sufficient, to elicit an HLA class II restricted response, peptide:HLA binding predictions do not necessarily predict which peptides will be immunogenic as dominant epitopes tend to be promiscuous binders (10, 13, 14).

Accordingly, the capacity of Fc peptides to bind a panel of 26 HLA class II alleles that are commonly expressed in representative ethnicities worldwide and in the US and for which epitope prediction tools are well established and publically available (8, 15), were predicted using tools available through IEDB (www.iedb.org). Three major promiscuous binding regions were identified, corresponding to residues 181-185 51-56 and 56-70 (pool 6), 181-195 and 186-200 (pool 19), 271-285 and 276-290 (pool 28) (FIG. 6 of Example 3, or FIG. 19).

These epitopes were compared with the HLA binding peptide patterns identified by the predicted binding analysis. Of the top 4 immunogenic pools, 3 corresponded to promiscuous binders (i.e. with predicted binding to ≥13 HLA alleles). Interestingly, pool 13 (peptides starting in positions 121 and 126), which was the most immunogenic, was not associated with predicted promiscuous binding. In fact, peptide 121 was predicted to bind only 3 alleles (HLA DRB1*0301, DRB1*1101 and DRB5*0101), and peptide 126 was not predicted to bind any. It is possible that this region might be associated with restriction by specific HLA alleles (monogamous restriction) that are present with high frequency in the donor cohort, and/or that were not present in the allele panel utilized for predictions.

DISCUSSION

In the present study we mapped the Fc peptide regions recognized by nTreg from sub-acute and convalescent KD subjects after IVIG therapy, from adults with a history of KD in childhood, and from healthy adult subjects. Using IL-10 secretion and CD4+CD25$^{high}$ T cell proliferation as a readout, we defined discrete Fc regions that are immunogenic. Our previous work suggested that immune-regulation via Fc-specific nTreg influences the clinical fate of KD patients and identified this as one mechanism by which IVIG leads to clinical improvement in these patients (3). However, 20-30% of KD patients go on to develop CAA with transient dilation or aneurysms despite timely treatment with IVIG and their nTreg do not respond to Fc stimulation in vitro (3, 4, 16).

By using Fc peptide epitopes as immunogens rather than the whole Fc protein, we demonstrated that nTreg from patients with CAA can expand in vitro (FIG. 1). These results suggest that T cell fitness, rather than T cell anergy or T cell clonal deletion causes the lack of Fe-specific response in KD patients with CAA who do not appear to respond to the whole Fc protein (3). Thus, the immunodominant Fc sequences recognized in the cohorts, i.e., the exemplary peptides as provided herein, can be used therapeutic agents. These exemplary peptides as provided herein can have significant advantages over whole IVIG in terms of safety, product reproducibility, and ease of definition and characterization. The predicted HLA binding analysis reported here supports the idea that most of the immunodominant Fc sequences, including exemplary peptides as provided herein, and recognized in the cohorts studied, will bind multiple HLA alleles and can be used as therapeutic peptides.

Among the Fc peptides identified as relevant for nTreg expansion after IVIG in KD patients, some include portions of the two long Fc sequences previously described as Tregitopes, pan-DR epitopes that were immunogenic in normal donors (17). Our results confirm the relevance of these Fc peptides in expanding regulatory T cells and their pan-DR potential binding capacity, but also suggest that the Tregitopes are not the most immunogenic sequences of the Fc protein for nTreg generation (FIGS. 1 and 3 of Example 3). Moreover, our data suggest that the Tregitopes are further trimmed for optimal HLA binding and TcR recognition since positions 51-65 and 56-60 (pool 6) contained within Tregitope 167 and positions 181-195 and 186-200 (pool 19) contained within Tregitope 289 were more immunogenic than other amino acid sequences within the two Tregitopes.

These studies suggest that Fe-specific nTreg responses in KD can be elicited by administration of large doses of IVIG in most patients. However, this regulatory T cell response is not long lasting and was undetectable in adult years after IVIG administration (FIG. 5). We therefore postulate a focal immune regulatory defect in patients who develop KD that can be overcome in the majority of patients by administration of a large dose of IVIG.

Figure Legends Example 3

FIG. 1 of Example 3 (or FIG. 14): nTreg fine specificities in sub-acute and convalescent KD subjects. $2 \times 10^5$ PBMC/well derived from 10 sub-acute and 6 convalescent KD subjects were cultured with pools of two Fc peptides (Table 3, see FIG. 13) for 4 days in the absence of exogenous lymphokines. IL-10 secretion in response to peptide stimulation was measured in culture supernatants by ELISA on day 4. Subjects 5 and 6 both developed CAA and IL-10 secretion was noted in their PBMC cultures incubated with peptides from Pools 28 and 6, respectively.

FIG. 2 of Example 3 (or FIG. 15): Response of nTreg to peptide pool 13. Enumeration of CD4+CD25$^{high}$ T cells from KD subject #10 in response to Fc 121-135 and 126-140 (pool 13), the most immunogenic sequences in this cohort of patients (P7, upper right).

FIG. 3 of Example 3 (or FIG. 16): IL-10 secretion in PBMC cultures from healthy adult donors in response to peptide pools. $2 \times 10^5$ PBMC/well derived from six healthy adult donors were cultured with pools of two Fc peptides (Table 3, see FIG. 13) for 4 days in the absence of exogenous lymphokines. IL-10 secretion by nTreg in response to peptide stimulation served as a read out in these experiments and was measured in culture supernatants by ELISA on day 4.

FIG. 4 of Example 3 (or FIG. 17): Pools 3 and 4 are more immunogenic in healthy donors than in KD patients. Panel A: IL-10 secretion in response to amino acid residues 21-35 and 26-40 (pool 3) and 31-45 and 36-50 (pool 4) in healthy donors. Panel B: nTreg responses to pools 3 and 4 in KD patients: only 2 of 12 KD subjects responded to these peptide pools.

FIG. 5 of Example 3 (or FIG. 18): CD4+CD25$^{high}$ nTreg expansion in response to scalar doses of Fc. PBMC were cultured for 4 days with 0, 1, 10, or 100 µg/ml purified Fc fragments. Panel A: Fc-specific nTreg response in adult subjects who had KD in childhood. Panel B: Fc-specific nTreg response in healthy adult controls.

FIG. 6 of Example 3 (or FIG. 19): HLA binding predictions of peptides derived from the Fc sequence. IEDB consensus algorithm was used to predict HLA class II binding affinity of the Fc sequences described in Table 3, see FIG. 13. Immunogenic peptide pools are indicated.

REFERENCES—EXAMPLE 2

1. Burns, et al. 2004. Kawasaki syndrome. Lancet 364:533-544.
2. Franco, et al. 2010. Memory T cells and characterization of peripheral T cell clones in acute Kawasaki disease. Autoimmunity 43:317-324.
3. Maddur, et al. 2010. Immunomodulation by intravenous immunoglobulin: role of regulatory T cells. J Clin Immunol. 1:S4-8.
4. Burns, et al. 2013. Immune-monitoring in Kawasaki disease patients treated with infliximab and intravenous immunoglobulin. Clinical and Experimental Immunol in press.
5. Campos Ramos, et al. 2012. The autoimmune nature of post-infarct myocardial healing: oral tolerance to cardiac antigens as a novel strategy to improve cardiac healing. Autoimmunity 45:233-244.
6. Trinath, et al. 2013. Intravenous immunoglobulin expands regulatory T cells via induction of cyclooxygenase-2-dependent prostaglandin E2 in human dendritic cells. Blood in press.
7. Roncarolo, et al. 2007. Regulatory T cell immunotherapy for tolerance to self antigens and to alloantigens in humans. Nature Reviews 7:585-598.
8. Wing, et al. 2010. Regulatory T cells exert checks and balances on self tolerance and autoimmunity. Nature Immunology 11:7-13.
9. von Boehmer, et al. 2010. Checkpoints in lymphocytes development and autoimmune disease. Nature Immunology 11:14-20.
10. Kassiotis, et al. 2008. Immunology. Immunity benefits from a little suppression. Science 320:1168-1169.
11. O'Garra, et al. 2004. IL-10-producing and naturally occurring CD4+ Tregs: limiting collateral damage. J Clin Invest. 2004 114:1372-1378.
12. Feuerer, et al. 2010. Foxp3+ regulatory T cells: differentiation, specification, subphenotypes. Nature Immunology 10:698-695.
13. Jordan, et al. 2001. Thymic selection of CD4+CD25+ regulatory T cells induced by an agonist self-peptide. Nat. Immunol. 2:301-306.
14. Miyara, et al. 2009. Functional delineation and differentiation dinamics of human CD4+ T cells expressing the FoxP3 transcription factor. Immunity 30:899-911.
15. Chen, et al. 2003. Conversion of Peripheral CD4+ CD25− Naive T Cells to CD4+CD25+ Regulatory T Cells by TGF-ß Induction of Transcription Factor Foxp3. J. Exp. Med. 198:1875-1886.
16. Kretschmer, et al. 2005. Inducing and expanding regulatory T cell populations by foreign antigen. Nature Immunol. 6:1-9.
17. Apostolou, et al. 2002. Origin of regulatory T cells with known specificity for antigen. Nat. Immunol. 3:756-763.
18. Apostolou, et al. 2004. In vivo instruction od suppressor commitment in naive T cells. Journal of Experimental Medicine 199:1401-1408.
19. Rivino, et al. 2010. CCR6 is expressed on IL-10 producing, autoreactive memory T cell population with context-dependent regulatory function. J. Exp. Med. 207:565-577.
20. Ohkura, et al. 2013. Development and maintenance of regulatory T cells. Immunity 38:414-423.
21. Chaudry, et al. 2013. Control of inflammation by integration of environmental cues by regulatory T cells. J. Clin. Invest. 123:939-944.
22. Sakaguchi, et al. 2013. The plasticity and stability of regulatory T cells. Nature Review in Immunology 13:461-467.

23. Povoleri, et al. 2013. Thymic versus induced regulatory T cells—who regulates the regulators? Front Immunol. 2013 Jun. 27; 4:169. doi: 10.3389/fimmu.2013.00169. Print 2013. 4:169
24. De Groot, et al. 2008. Activation of natural regulatory T cells by IG Fc-derived peptide "Tregitopes". Blood 112: 3303-3311
25. Franco, et al. 1992. Transferrin receptor mediates uptake and presentation of hepatitis B envelope antigen by T lymphocytes J. Exp. Med. 175:1195-1205.
26. Zlotnik, et al. 2012. The chemokine superfamily revisited. Immunity 36:705-716.
27. Maddur, et al. 2011. Comparison of different IVIG preparations on IL-17 production by human Th17 cells. Autoimmun. Rev. 12:809-810.
28. Ephrem, et al. 2008. Expansion of CD4+CD25+ regulatory T cells by intravenous immunoglobulin: a critical factor in controlling experimental autoimmune encephalitis. Blood 111:715-722.
29. Reboldi, A et al. 2009. C—C chemokine receptor 6-regulated entry of TH-17 cells into the CNS through the choroid plexus is required for the initiation of EAE. Nature immunol. 10:514-523.
30. Zielinski, et al. 2012. Pathogen-induced human TH17 cells produce IFN-γ or IL-10 and are regulated by IL-113. Nature 484:514-518.
31. Ward, E. S. 2004. Acquiring maternal immunoglobulin; different receptors, similar functions. Immunity 20:507-508.
32. He, et al. 2008. FcRn-mediated antibody transport across epithelial cells revealed by electron tomography. Nature 455:542-546.
33. Rizzi, et al. 2005. In utero DNA immunisation. Immunity over tolerance in fetal life. Vaccine 23:4273-4283.
34. Bayry, et al. 2011. Intravenous immunoglobulin therapy in rheumatic diseases. Nat Rev Rheumatol. 7:349-359.

REFERENCES—EXAMPLE 3

1. Jordan, et al. 2001. Thymic selection of CD4+CD25+ regulatory T cells induced by an agonist self-peptide. Nat. Immunol. 2:301-306.
2. Miyara, et al. 2009. Functional delineation and differentiation dinamic of human CD4+ T cells expressing the FoxP3 transcription factor. Immunity 30:899-911.
3. Franco, et al. 2014. Specificity of regulatory T cells that modulate vascular inflammation. Autoimmunity 47:95-104.
4. Ogata, et al. 2013. Treatment response in Kawasaki disease is associated with sialylation levels of endogenous but not therapeutic intravenous immunoglobulin G. PLoS one 8:e81448.
5. Franco, A., Shimizu, C., Tremoulet, A. H., Burns, J. C. 2010. Memory T cells and characterization of peripheral T cell clones in acute Kawasaki disease. Autoimmunity 43:317-324.
6. Franco, et al. 2010. Endoplasmic reticulum stress drives a regulatory phenotype in human T cell clones. Cell. Immunol. 266:1-6.
7. Burns, et al. 2013. Immune-monitoring in Kawasaki disease patients treated with infliximab and intravenous immunoglobulin. Clinical and Experimental Immunology 174:337-344.
8. Wang, et al. 2010. Peptide binding predictions for HLA DR, DP and DQ molecules. BMC Bioinformatics 11:568.
9. Tangri, et al. 2005. Rationally engineered therapeutic proteins with reduced immunogenicity. J Immunol. 174: 3187-3196.
10. Oseroff, et al. 2010. Molecular determinants of T cell epitope recognition to the common Timothy grass allergen. Journal of Immunology 185:943-955.
11. Oseroff, et al. 2012. T Cell Responses to Known Allergen Proteins Are Differently Polarized and Account for a Variable Fraction of Total Response to Allergen Extracts. J. Immunol. 189:1800-1811.
12. Lindestam Arlehamn, et al. 2013. Memory T cells in latent *Mycobacterium tuberculosis* infection are directed against three antigenic islands and largely contained in a CXCR3+CCR6+Th1 subset. PLoS Pathog. 9(1): e1003130. doi: 1003110.1001371/journal.ppat.1003130.
13. Alexander, et al. 1994. Development of high potency universal DR-restricted helper epitopes by modification of high affinity DR-blocking peptides. Immunity 1:751-761.
14. Paul, et al. 2013. Evaluating the immunogenicity of protein drugs by applying in vitro MHC binding data and the immune epitope database and analysis resource. 2013: 467852. doi: 467810.461155/462013/467852.
15. Arens, et al. 2008. Cutting edge: murine cytomegalovirus induces a polyfunctional CD4 T cell response. J Immunol 180.
16. Burns, J. C., Glode, M. P. 2004. Kawasaki syndrome. Lancet 364:533-544.
17. De Groot, et al. 2008. Activation of natural regulatory T cells by IG Fc-derived peptide "Tregitopes". Blood 112: 3303-3311.

A number of aspects of embodiments as provided herein have been described. Nevertheless, it will be understood that various modifications may be made without departing from the spirit and scope of the invention. Accordingly, other aspects are within the scope of the following claims.

What is claimed is:

1. A pharmaceutical composition or a formulation comprising a plurality of isolated, synthetic or recombinant peptides or polypeptides comprising:

TAALGCLVKDYFPEP, (SEQ ID NO: 1)
CLVKDYFPEPVTVSW, (SEQ ID NO: 2)
SVFLFPPKPKDTLMI, (SEQ ID NO: 3)
TFPAVLQSSGLYSLS, (SEQ ID NO: 9)
TYRVVSVLTVLHQDW, (SEQ ID NO: 14)
QGNVFSCSVMHEALH, (SEQ ID NO: 16)
YFPEPVTVSWNSGAL, (SEQ ID NO: 22)
VTVSWNSGALTSGVH, (SEQ ID NO: 23)
LQSSGLYSLSSVVTV, (SEQ ID NO: 10)
LYSLSSVVTVPSSSL, (SEQ ID NO: 11)
SCSVMHEALHNHYTQ, (SEQ ID NO: 17)
and
SVLTVLHQDWLNGKE, (SEQ ID NO: 45)

and a pharmaceutically acceptable excipient.

2. The pharmaceutical composition or formulation of claim 1, comprising a plurality of isolated, synthetic or recombinant peptides consisting essentially of:

TAALGCLVKDYFPEP, (SEQ ID NO: 1)
CLVKDYFPEPVTVSW, (SEQ ID NO: 2)
SVFLFPPKPKDTLMI, (SEQ ID NO: 3)
TFPAVLQSSGLYSLS, (SEQ ID NO: 9)
TYRVVSVLTVLHQDW, (SEQ ID NO: 14)
QGNVFSCSVMHEALH, (SEQ ID NO: 16)
YFPEPVTVSWNSGAL, (SEQ ID NO: 22)
VTVSWNSGALTSGVH, (SEQ ID NO: 23)
LQSSGLYSLSSVVTV, (SEQ ID NO: 10)
LYSLSSVVTVPSSSL, (SEQ ID NO: 11)
SCSVMHEALHNHYTQ, (SEQ ID NO: 17)
and
SVLTVLHQDWLNGKE, (SEQ ID NO: 45)

and a pharmaceutically acceptable excipient.

3. The pharmaceutical composition or formulation of claim 2, comprising a plurality of isolated, synthetic or recombinant peptides consisting of:

TAALGCLVKDYFPEP, (SEQ ID NO: 1)
CLVKDYFPEPVTVSW, (SEQ ID NO: 2)
SVFLFPPKPKDTLMI, (SEQ ID NO: 3)

-continued

TFPAVLQSSGLYSLS, (SEQ ID NO: 9)

TYRVVSVLTVLHQDW, (SEQ ID NO: 14)

QGNVFSCSVMHEALH, (SEQ ID NO: 16)

YFPEPVTVSWNSGAL, (SEQ ID NO: 22)

VTVSWNSGALTSGVH, (SEQ ID NO: 23)

LQSSGLYSLSSVVTV, (SEQ ID NO: 10)

LYSLSSVVTVPSSSL, (SEQ ID NO: 11)

SCSVMHEALHNHYTQ, (SEQ ID NO: 17)
and

SVLTVLHQDWLNGKE, (SEQ ID NO: 45)

and a pharmaceutically acceptable excipient.

4. The pharmaceutical composition or formulation of claim 1, wherein the pharmaceutical composition or formulation is a parenteral formulation; or the pharmaceutical composition or formulation is an oral or topical formulation.

5. The pharmaceutical composition or formulation of claim 1, formulated as a sterile solution for injection.

6. The pharmaceutical composition or formulation of claim 1, formulated as a liquid, an emulsion, a lyophilized powder, a spray, a cream, a lotion, a controlled release formulation, a tablet, a pill, a gel, a patch, in an implant or in a spray.

7. The pharmaceutical composition or formulation of claim 1, wherein the pharmaceutical composition or formulation is a subcutaneous, an intravenous (IV), an intradermal, an intramuscular, an intraperitoneal, an intranasal, a transdermal or a buccal route formulation.

8. The pharmaceutical composition or formulation of claim 1, wherein the pharmaceutical composition or formulation is an inhaled powder.

9. The pharmaceutical composition or formulation of claim 1, wherein the pharmaceutical composition or formulation is a controlled release formulation.

10. The pharmaceutical composition or formulation of claim 1, wherein the pharmaceutical composition or formulation is a tablet, a pill, a gel, a patch, in an implant or a spray formulation.

11. The pharmaceutical composition or formulation of claim 1, formulated as a sterile solution for injection.

12. The pharmaceutical composition or formulation of claim 1, formulated as a powder.

13. The pharmaceutical composition or formulation of claim 1, formulated as a lyophilized or freeze-dried composition.

14. The pharmaceutical composition or formulation of claim 1, formulated as an aqueous or a non-aqueous isotonic sterile injection solution or formulated an aqueous or a non-aqueous sterile suspension.

15. The pharmaceutical composition or formulation of claim 1, wherein the plurality of peptides or polypeptides are synthetic peptides or polypeptides.

16. The pharmaceutical composition or formulation of claim 1, wherein the plurality of peptides or polypeptides are recombinant peptides or polypeptides.

17. A liposome comprising: a pharmaceutical or formulation of claim 1.

18. A nanoparticle comprising: a pharmaceutical or formulation of claim 1.

19. A vaccine comprising a pharmaceutical or formulation of claim 1.

20. The vaccine of claim 19, further comprises an adjuvant.

21. The vaccine of claim 20, wherein the adjuvant comprises an incomplete adjuvant.

* * * * *

SEQUENCE LISTING

<160> NUMBER OF SEQ ID NOS: 63

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Thr Ala Ala Leu Gly Cys Leu Val Lys Asp Tyr Phe Pro Glu Pro
1               5                   10                  15

```
<210> SEQ ID NO 2
<211> LENGTH: 15
<212> TYPE: PRT
<213> ORGANISM: Artificial Sequence
<220> FEATURE:
<223> OTHER INFORMATION: synthetic peptide

<400> SEQUENCE: 2

Cys Leu Val Lys Asp Tyr Phe Pro Glu Pro Val Thr Val Ser Trp
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: synthetic peptide

<400> SEQUENCE: 3

Ser Val Phe Leu Phe Pro Pro Lys Pro Lys Asp Thr Leu Met Ile
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: synthetic peptide

<400> SEQUENCE: 4

Pro Pro Lys Pro Lys Asp Thr Leu Met Ile Ser Arg Thr Pro Glu
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: synthetic peptide

<400> SEQUENCE: 5

Lys Leu Thr Val Asp Lys Ser Arg Trp Gln Gln Gly Asn Val Phe
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic peptide

<400> SEQUENCE: 6

Lys Ser Arg Trp Gln Gln Gly Asn Val Phe Ser Cys Ser Val Met
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: synthetic peptide

<400> SEQUENCE: 7

Asn Gly Gln Pro Glu Asn Asn Tyr Lys Thr Thr Pro Pro Val Leu
1               5                   10                  15
```

-continued

```
<210> SEQ ID NO 8
<211> LENGTH: 15
<212> TYPE: PRT
<213> ORGANISM: Artificial Sequence
<220> FEATURE:
<223> OTHER INFORMATION: synthetic peptide

<400> SEQUENCE: 8

Asn Asn Tyr Lys Thr Thr Pro Pro Val Leu Asp Ser Asp Gly Ser
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: synthetic peptide

<400> SEQUENCE: 9

Thr Phe Pro Ala Val Leu Gln Ser Ser Gly Leu Tyr Ser Leu Ser
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: synthetic peptide

<400> SEQUENCE: 10

Leu Gln Ser Ser Gly Leu Tyr Ser Leu Ser Ser Val Val Thr Val
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: synthetic peptide

<400> SEQUENCE: 11

Leu Tyr Ser Leu Ser Ser Val Val Thr Val Pro Ser Ser Ser Leu
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: synthetic peptide

<400> SEQUENCE: 12

Ser Val Val Thr Val Pro Ser Ser Ser Leu Gly Thr Gln Thr Tyr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: synthetic peptide

<400> SEQUENCE: 13

Glu Gln Tyr Asn Ser Thr Tyr Arg Val Val Ser Val Leu Thr Val
1               5                   10                  15
```

```
<210> SEQ ID NO 14
<211> LENGTH: 15
<212> TYPE: PRT
<213> ORGANISM: Artificial Sequence
<220> FEATURE:
<223> OTHER INFORMATION: synthetic peptide

<400> SEQUENCE: 14

Thr Tyr Arg Val Val Ser Val Leu Thr Val Leu His Gln Asp Trp
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: synthetic peptide

<400> SEQUENCE: 15

Thr Pro Pro Val Leu Asp Ser Asp Gly Ser Phe Phe Leu Tyr Ser
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: synthetic peptide

<400> SEQUENCE: 16

Gln Gly Asn Val Phe Ser Cys Ser Val Met His Glu Ala Leu His
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: synthetic peptide

<400> SEQUENCE: 17

Ser Cys Ser Val Met His Glu Ala Leu His Asn His Tyr Thr Gln
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: synthetic peptide

<400> SEQUENCE: 18

Ser Thr Lys Gly Pro Ser Val Phe Pro Leu Ala Pro Ser Ser Lys
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: synthetic peptide

<400> SEQUENCE: 19

Ser Val Phe Pro Leu Ala Pro Ser Ser Lys Ser Thr Ser Gly Gly
1               5                   10                  15
```

```
<210> SEQ ID NO 20
<211> LENGTH: 15
<212> TYPE: PRT
<213> ORGANISM: Artificial Sequence
<220> FEATURE:
<223> OTHER INFORMATION: synthetic peptide

<400> SEQUENCE: 20

Ala Pro Ser Ser Lys Ser Thr Ser Gly Gly Thr Ala Ala Leu Gly
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: synthetic peptide

<400> SEQUENCE: 21

Ser Thr Ser Gly Gly Thr Ala Ala Leu Gly Cys Leu Val Lys Asp
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: synthetic peptide

<400> SEQUENCE: 22

Tyr Phe Pro Glu Pro Val Thr Val Ser Trp Asn Ser Gly Ala Leu
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: synthetic peptide

<400> SEQUENCE: 23

Val Thr Val Ser Trp Asn Ser Gly Ala Leu Thr Ser Gly Val His
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: synthetic peptide

<400> SEQUENCE: 24

Asn Ser Gly Ala Leu Thr Ser Gly Val His Thr Phe Pro Ala Val
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: synthetic peptide

<400> SEQUENCE: 25

Thr Ser Gly Val His Thr Phe Pro Ala Val Leu Gln Ser Ser Gly
1               5                   10                  15
```

```
<210> SEQ ID NO 26
<211> LENGTH: 15
<212> TYPE: PRT
<213> ORGANISM: Artificial Sequence
<220> FEATURE:
<223> OTHER INFORMATION: synthetic peptide

<400> SEQUENCE: 26

Pro Ser Ser Ser Leu Gly Thr Gln Thr Tyr Ile Cys Asn Val Asn
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: synthetic peptide

<400> SEQUENCE: 27

Gly Thr Gln Thr Tyr Ile Cys Asn Val Asn His Lys Pro Ser Asn
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: synthetic peptide

<400> SEQUENCE: 28

Ile Cys Asn Val Asn His Lys Pro Ser Asn Thr Lys Val Asp Lys
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: synthetic peptide

<400> SEQUENCE: 29

His Lys Pro Ser Asn Thr Lys Val Asp Lys Lys Val Glu Pro Lys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: synthetic peptide

<400> SEQUENCE: 30

Thr Lys Val Asp Lys Lys Val Glu Pro Lys Ser Cys Asp Lys Thr
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: synthetic peptide

<400> SEQUENCE: 31

Lys Val Glu Pro Lys Ser Cys Asp Lys Thr His Thr Cys Pro Pro
1               5                   10                  15
```

```
<210> SEQ ID NO 32
<211> LENGTH: 15
<212> TYPE: PRT
<213> ORGANISM: Artificial Sequence
<220> FEATURE:
<223> OTHER INFORMATION: synthetic peptide

<400> SEQUENCE: 32

Ser Cys Asp Lys Thr His Thr Cys Pro Pro Cys Pro Ala Pro Glu
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: synthetic peptide

<400> SEQUENCE: 33

His Thr Cys Pro Pro Cys Pro Ala Pro Glu Leu Leu Gly Gly Pro
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: synthetic peptide

<400> SEQUENCE: 34

Cys Pro Ala Pro Glu Leu Leu Gly Gly Pro Ser Val Phe Leu Phe
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: synthetic peptide

<400> SEQUENCE: 35

Cys Pro Ala Pro Glu Leu Leu Gly Gly Pro Ser Val Phe Leu Phe
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: synthetic peptide

<400> SEQUENCE: 36

Asp Thr Leu Met Ile Ser Arg Thr Pro Glu Val Thr Cys Val Val
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: synthetic peptide

<400> SEQUENCE: 37

Ser Arg Thr Pro Glu Val Thr Cys Val Val Val Asp Val Ser His
1               5                   10                  15
```

```
<210> SEQ ID NO 38
<211> LENGTH: 15
<212> TYPE: PRT
<213> ORGANISM: Artificial Sequence
<220> FEATURE:
<223> OTHER INFORMATION: synthetic peptide

<400> SEQUENCE: 38

Val Thr Cys Val Val Val Asp Val Ser His Glu Asp Pro Glu Val
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: synthetic peptide

<400> SEQUENCE: 39

Val Asp Val Ser His Glu Asp Pro Glu Val Lys Phe Asn Trp Tyr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: synthetic peptide

<400> SEQUENCE: 40

Glu Asp Pro Glu Val Lys Phe Asn Trp Tyr Val Asp Gly Val Glu
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: synthetic peptide

<400> SEQUENCE: 41

Lys Phe Asn Trp Tyr Val Asp Gly Val Glu Val His Asn Ala Lys
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: synthetic peptide

<400> SEQUENCE: 42

Val Asp Gly Val Glu Val His Asn Ala Lys Thr Lys Pro Arg Glu
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: synthetic peptide

<400> SEQUENCE: 43

Val His Asn Ala Lys Thr Lys Pro Arg Glu Glu Gln Tyr Asn Ser
1               5                   10                  15
```

```
<210> SEQ ID NO 44
<211> LENGTH: 15
<212> TYPE: PRT
<213> ORGANISM: Artificial Sequence
<220> FEATURE:
<223> OTHER INFORMATION: synthetic peptide

<400> SEQUENCE: 44

Thr Lys Pro Arg Glu Glu Gln Tyr Asn Ser Thr Tyr Arg Val Val
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: synthetic peptide

<400> SEQUENCE: 45

Ser Val Leu Thr Val Leu His Gln Asp Trp Leu Asn Gly Lys Glu
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: synthetic peptide

<400> SEQUENCE: 46

Leu His Gln Asp Trp Leu Asn Gly Lys Glu Tyr Lys Cys Lys Val
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: synthetic peptide

<400> SEQUENCE: 47

Leu Asn Gly Lys Glu Tyr Lys Cys Lys Val Ser Asn Lys Ala Leu
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: synthetic peptide

<400> SEQUENCE: 48

Ser Asn Lys Ala Leu Pro Ala Pro Ile Glu Lys Thr Ile Ser Lys
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: synthetic peptide

<400> SEQUENCE: 49

Pro Ala Pro Ile Glu Lys Thr Ile Ser Lys Ala Lys Gly Gln Pro
1               5                   10                  15
```

```
<210> SEQ ID NO 50
<211> LENGTH: 15
<212> TYPE: PRT
<213> ORGANISM: Artificial Sequence
<220> FEATURE:
<223> OTHER INFORMATION: synthetic peptide

<400> SEQUENCE: 50

Lys Thr Ile Ser Lys Ala Lys Gly Gln Pro Arg Glu Pro Gln Val
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: synthetic peptide

<400> SEQUENCE: 51

Ala Lys Gly Gln Pro Arg Glu Pro Gln Val Tyr Thr Leu Pro Pro
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: synthetic peptide

<400> SEQUENCE: 52

Arg Glu Pro Gln Val Tyr Thr Leu Pro Pro Ser Arg Asp Glu Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: synthetic peptide

<400> SEQUENCE: 53

Tyr Thr Leu Pro Pro Ser Arg Asp Glu Leu Thr Lys Asn Gln Val
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: synthetic peptide

<400> SEQUENCE: 54

Ser Arg Asp Glu Leu Thr Lys Asn Gln Val Ser Leu Thr Cys Leu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: synthetic peptide

<400> SEQUENCE: 55

Thr Lys Asn Gln Val Ser Leu Thr Cys Leu Val Lys Gly Phe Tyr
1               5                   10                  15
```

<210> SEQ ID NO 56
<211> LENGTH: 15
<212> TYPE: PRT
<213> ORGANISM: Artificial Sequence
<220> FEATURE:
<223> OTHER INFORMATION: synthetic peptide

<400> SEQUENCE: 56

Ser Leu Thr Cys Leu Val Lys Gly Phe Tyr Pro Ser Asp Ile Ala
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: synthetic peptide

<400> SEQUENCE: 57

Val Lys Gly Phe Tyr Pro Ser Asp Ile Ala Val Glu Trp Glu Ser
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: synthetic peptide

<400> SEQUENCE: 58

Pro Ser Asp Ile Ala Val Glu Trp Glu Ser Asn Gly Gln Pro Glu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: synthetic peptide

<400> SEQUENCE: 59

Val Glu Trp Glu Ser Asn Gly Gln Pro Glu Asn Asn Tyr Lys Thr
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: synthetic peptide

<400> SEQUENCE: 60

Asp Ser Asp Gly Ser Phe Phe Leu Tyr Ser Lys Leu Thr Val Asp
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: synthetic peptide

<400> SEQUENCE: 61

Phe Phe Leu Tyr Ser Lys Leu Thr Val Asp Lys Ser Arg Trp Gln
1               5                   10                  15

```
<210> SEQ ID NO 62
<211> LENGTH: 15
<212> TYPE: PRT
<213> ORGANISM: Artificial Sequence
<220> FEATURE:
<223> OTHER INFORMATION: synthetic peptide

<400> SEQUENCE: 62

His Glu Ala Leu His Asn His Tyr Thr Gln Lys Ser Leu Ser Leu
1               5                   10                  15

<210> SEQ ID NO 63
<211> LENGTH: 14
<212> TYPE: PRT
<213> ORGANISM: Artificial Sequence
<220> FEATURE:
<223> OTHER INFORMATION: synthetic peptide

<400> SEQUENCE: 63

Asn His Tyr Thr Gln Lys Ser Leu Ser Leu Ser Pro Gly Lys
1               5                   10
```